United States Patent
Sun et al.

(10) Patent No.: US 12,193,738 B2
(45) Date of Patent: Jan. 14, 2025

(54) INTRAVASCULAR LITHOTRIPSY

(71) Applicant: FastWave Medical Inc., Dover, DE (US)

(72) Inventors: JiChao Sun, Santa Rosa, CA (US); Parker Hagen, Maple Grove, MN (US); Dannah Dean, Minnetonka, MN (US); Lauren Eno, Prior Lake, MN (US); Brady Hatcher, Rogers, MN (US); Curtis Goreham-Voss, Maple Grove, MN (US); Tristan Tieso, Minneapolis, MN (US); Edward Anderson, Maple Grove, MN (US); Scott Nelson, Reno, NV (US); Dean Irwin, Carlsbad, CA (US); Bryan Goh, Maple Grove, MN (US); Charles Anthony Plowe, Blaine, MN (US); Randy Beyreis, Andover, MN (US)

(73) Assignee: FastWave Medical Inc., Dover, DE (US)

( * ) Notice: Subject to any disclaimer, the term of this patent is extended or adjusted under 35 U.S.C. 154(b) by 0 days.

(21) Appl. No.: 18/595,031

(22) Filed: Mar. 4, 2024

(65) Prior Publication Data
US 2024/0206972 A1 Jun. 27, 2024

Related U.S. Application Data

(63) Continuation-in-part of application No. 18/322,562, filed on May 23, 2023, now Pat. No. 11,918,285.
(Continued)

(51) Int. Cl.
*A61B 18/20* (2006.01)
*A61B 18/26* (2006.01)
(Continued)

(52) U.S. Cl.
CPC .... *A61B 18/26* (2013.01); *A61B 2017/22038* (2013.01); *A61B 2018/0022* (2013.01);
(Continued)

(58) Field of Classification Search
CPC ......... A61B 18/20; A61B 18/24; A61B 18/26; A61N 5/06
See application file for complete search history.

(56) References Cited

U.S. PATENT DOCUMENTS

| 4,587,975 A | 5/1986 | Salo et al. |
| 5,116,227 A | 5/1992 | Levy |

(Continued)

FOREIGN PATENT DOCUMENTS

| DE | 3038445 C2 | 6/1990 |
| EP | 0571306 A1 | 11/1993 |

(Continued)

OTHER PUBLICATIONS

Shockwave Medical—"Intravascular Lithotripsy (IVL)"—shockwavemedical.com [online]—Available at least as of Apr. 2022—Available from Internet <URL: https://shockwavemedical.com/technology/intravascular-lithotripsy-ivl/>.
(Continued)

*Primary Examiner* — Lynsey C Eiseman
(74) *Attorney, Agent, or Firm* — Gallium Law; Jacob Panangat; Justin Schwechter

(57) ABSTRACT

A medical device may include an elongated body having a distal elongated body portion and a central longitudinal axis. The medical device may include a balloon positioned along the distal elongated body portion. The balloon may be configured to receive a fluid to inflate the balloon such that an exterior balloon surface contacts a calcified lesion within a patient's vasculature. The medical device may include one or more pressure wave emitters positioned along the central
(Continued)

longitudinal axis of the elongated body. The one or more pressure wave emitters may be configured to propagate at least one pressure wave through the fluid to fragment the calcified lesion. At least one pressure wave emitter may include an optical fiber configured to transmit laser energy into the balloon. The laser energy may be configured to create a cavitation bubble in the fluid.

20 Claims, 60 Drawing Sheets

Related U.S. Application Data

(60) Provisional application No. 63/482,547, filed on Jan. 31, 2023, provisional application No. 63/381,487, filed on Oct. 28, 2022, provisional application No. 63/347,981, filed on Jun. 1, 2022.

(51) Int. Cl.
  *A61B 17/22* (2006.01)
  *A61B 18/00* (2006.01)
  *A61B 18/22* (2006.01)

(52) U.S. Cl.
  CPC . *A61B 2018/2261* (2013.01); *A61B 2018/263* (2013.01); *A61B 2018/266* (2013.01)

(56) References Cited

U.S. PATENT DOCUMENTS

| | | | |
|---|---|---|---|
| 5,536,252 | A | 7/1996 | Imran et al. |
| 6,004,269 | A | 12/1999 | Crowley et al. |
| 6,514,249 | B1 | 2/2003 | Maguire et al. |
| 6,652,547 | B2 | 11/2003 | Rabiner et al. |
| 6,755,821 | B1 | 6/2004 | Fry |
| 7,144,408 | B2 | 12/2006 | Keegan et al. |
| 8,409,172 | B2 | 4/2013 | Moll et al. |
| 8,419,613 | B2 | 4/2013 | Saadat et al. |
| 8,439,890 | B2 | 5/2013 | Beyar et al. |
| 8,657,814 | B2 | 2/2014 | Werneth et al. |
| 8,728,091 | B2 | 5/2014 | Hakala et al. |
| 8,747,416 | B2 | 6/2014 | Hakala et al. |
| 8,888,788 | B2 | 11/2014 | Hakala et al. |
| 8,956,371 | B2 | 2/2015 | Hawkins et al. |
| 8,956,374 | B2 | 2/2015 | Hawkins et al. |
| 9,005,216 | B2 | 4/2015 | Hakala et al. |
| 9,011,462 | B2 | 4/2015 | Adams et al. |
| 9,011,463 | B2 | 4/2015 | Adams et al. |
| 9,072,534 | B2 | 7/2015 | Adams et al. |
| 9,138,249 | B2 | 9/2015 | Adams et al. |
| 9,333,000 | B2 | 5/2016 | Hakala et al. |
| 9,370,644 | B2 | 6/2016 | Rocha-Singh |
| 9,433,428 | B2 | 9/2016 | Hakala et al. |
| 9,522,012 | B2 | 12/2016 | Adams |
| 9,642,673 | B2 | 5/2017 | Adams et al. |
| 9,867,629 | B2 | 1/2018 | Hawkins |
| 10,039,561 | B2 | 8/2018 | Adams et al. |
| 10,143,577 | B2 | 12/2018 | Simpson |
| 10,159,505 | B2 | 12/2018 | Hakala et al. |
| 10,201,387 | B2 | 2/2019 | Grace et al. |
| 10,206,698 | B2 | 2/2019 | Hakala et al. |
| 10,226,265 | B2 | 3/2019 | Ku et al. |
| 10,357,264 | B2 | 7/2019 | Kat-Kuoy et al. |
| 10,517,620 | B2 | 12/2019 | Adams |
| 10,517,621 | B1 | 12/2019 | Hakala et al. |
| 10,682,178 | B2 | 6/2020 | Adams et al. |
| 10,702,293 | B2 | 7/2020 | Adams et al. |
| 10,709,462 | B2 | 7/2020 | Nguyen et al. |
| 10,786,267 | B2 | 9/2020 | Wasdyke et al. |
| 10,786,661 | B2 | 9/2020 | Grace |
| 10,842,567 | B2 | 11/2020 | Grace et al. |
| 10,850,078 | B2 | 12/2020 | Grace et al. |
| 10,898,213 | B2 | 1/2021 | Grace et al. |
| 10,959,743 | B2 | 3/2021 | Adams et al. |
| 10,966,737 | B2 | 4/2021 | Nguyen |
| 10,973,538 | B2 | 4/2021 | Hakala et al. |
| 11,058,492 | B2 | 7/2021 | Grace et al. |
| 11,076,874 | B2 | 8/2021 | Hakala et al. |
| 11,246,659 | B2 | 2/2022 | Grace et al. |
| 11,266,817 | B2 | 3/2022 | Cope et al. |
| 11,376,071 | B2 | 7/2022 | Brown et al. |
| 11,432,834 | B2 | 9/2022 | Adams |
| 11,517,713 | B2 | 12/2022 | Massimini et al. |
| 11,534,187 | B2 | 12/2022 | Bonutti |
| 11,622,779 | B2 | 4/2023 | McGowan et al. |
| 11,918,285 | B2 | 3/2024 | Sun et al. |
| 2002/0052621 | A1 | 5/2002 | Fried |
| 2004/0015184 | A1 | 1/2004 | Boyle |
| 2005/0251116 | A1 | 11/2005 | Steinke et al. |
| 2006/0064082 | A1 | 3/2006 | Bonutti |
| 2006/0190022 | A1 | 8/2006 | Beyer et al. |
| 2007/0078500 | A1* | 4/2007 | Ryan .................... A61B 5/6853 600/473 |
| 2007/0179496 | A1 | 8/2007 | Swoyer et al. |
| 2008/0109029 | A1 | 5/2008 | Gurm |
| 2009/0137952 | A1* | 5/2009 | Ramamurthy ..... A61B 1/00004 604/95.01 |
| 2009/0227992 | A1 | 9/2009 | Nir et al. |
| 2010/0036294 | A1 | 2/2010 | Mantell et al. |
| 2011/0257641 | A1 | 10/2011 | Hastings et al. |
| 2016/0135828 | A1 | 5/2016 | Hawkins |
| 2016/0183819 | A1 | 6/2016 | Burnett et al. |
| 2016/0287323 | A1 | 10/2016 | Yagi |
| 2016/0324571 | A1 | 11/2016 | Beeckler |
| 2017/0265942 | A1 | 9/2017 | Grace et al. |
| 2018/0042661 | A1 | 2/2018 | Long et al. |
| 2019/0104933 | A1 | 4/2019 | Stern et al. |
| 2019/0247680 | A1 | 8/2019 | Mayer et al. |
| 2019/0388110 | A1 | 12/2019 | Nguyen et al. |
| 2020/0000484 | A1 | 1/2020 | Hawkins |
| 2020/0008856 | A1 | 1/2020 | Harmouche et al. |
| 2020/0060704 | A1 | 2/2020 | Ein-Gal |
| 2020/0085458 | A1 | 3/2020 | Nguyen |
| 2020/0155818 | A1 | 5/2020 | Yang |
| 2020/0237388 | A1 | 7/2020 | Eisenfrats et al. |
| 2020/0297366 | A1 | 9/2020 | Nguyen et al. |
| 2020/0383724 | A1 | 12/2020 | Adams et al. |
| 2020/0397230 | A1 | 12/2020 | Massimini et al. |
| 2020/0397453 | A1 | 12/2020 | McGowan et al. |
| 2020/0398033 | A1 | 12/2020 | McGowan et al. |
| 2020/0406009 | A1 | 12/2020 | Massimini et al. |
| 2021/0085347 | A1 | 3/2021 | Phan et al. |
| 2021/0085348 | A1 | 3/2021 | Nguyen |
| 2021/0128241 | A1 | 5/2021 | Schultheis |
| 2021/0137598 | A1 | 5/2021 | Cook et al. |
| 2021/0153939 | A1 | 5/2021 | Cook et al. |
| 2021/0196379 | A1 | 7/2021 | Brown et al. |
| 2021/0220053 | A1 | 7/2021 | Cook |
| 2021/0244473 | A1 | 8/2021 | Cook et al. |
| 2021/0267685 | A1 | 9/2021 | Schultheis et al. |
| 2021/0275247 | A1 | 9/2021 | Schultheis et al. |
| 2021/0275249 | A1 | 9/2021 | Massimini et al. |
| 2021/0282792 | A1 | 9/2021 | Adams et al. |
| 2021/0290259 | A1 | 9/2021 | Hakala et al. |
| 2021/0290286 | A1 | 9/2021 | Cook et al. |
| 2021/0290305 | A1 | 9/2021 | Cook et al. |
| 2021/0307828 | A1 | 10/2021 | Schultheis et al. |
| 2021/0330384 | A1 | 10/2021 | Cook et al. |
| 2021/0353359 | A1 | 11/2021 | Cook et al. |
| 2021/0369348 | A1 | 12/2021 | Cook et al. |
| 2021/0378743 | A1 | 12/2021 | Massimini et al. |
| 2021/0386479 | A1 | 12/2021 | Massimini et al. |
| 2022/0008130 | A1 | 1/2022 | Massimini et al. |
| 2022/0054194 | A1 | 2/2022 | Bacher et al. |
| 2022/0071704 | A1 | 3/2022 | Le |
| 2022/0183708 | A1 | 6/2022 | Phan |
| 2022/0183738 | A1 | 6/2022 | Flores et al. |
| 2022/0183756 | A1 | 6/2022 | Milner |
| 2022/0240958 | A1 | 8/2022 | Nguyen |
| 2022/0249165 | A1 | 8/2022 | Cook et al. |
| 2022/0249166 | A1 | 8/2022 | Cook |
| 2022/0265295 | A1 | 8/2022 | McCaffrey |

(56) References Cited

U.S. PATENT DOCUMENTS

| | | |
|---|---|---|
| 2022/0273324 A1 | 9/2022 | Schultheis |
| 2022/0287730 A1 | 9/2022 | Chisena |
| 2022/0287732 A1 | 9/2022 | Anderson et al. |
| 2022/0313359 A1 | 10/2022 | Schultheis |
| 2022/0354578 A1 | 11/2022 | Cook et al. |
| 2022/0387106 A1 | 12/2022 | Cook |
| 2023/0037716 A1 | 2/2023 | Batchelder |
| 2023/0038308 A1 | 2/2023 | Batchelder |
| 2023/0038388 A1 | 2/2023 | Batchelder |
| 2023/0038663 A1 | 2/2023 | Batchelder |
| 2023/0040190 A1 | 2/2023 | Batchelder |
| 2023/0040420 A1 | 2/2023 | Batchelder |
| 2023/0041407 A1 | 2/2023 | Batchelder |
| 2023/0044926 A1 | 2/2023 | Batchelder |
| 2023/0064371 A1 | 3/2023 | Cook et al. |
| 2023/0389987 A1 | 12/2023 | Sun et al. |

FOREIGN PATENT DOCUMENTS

| | | |
|---|---|---|
| JP | S62-275446 A | 11/1987 |
| JP | 2004121859 A | 4/2004 |
| WO | 2020141068 A1 | 7/2020 |
| WO | 2020168213 A1 | 8/2020 |
| WO | 2021162855 A1 | 8/2021 |
| WO | 2021247685 A1 | 12/2021 |
| WO | 2022055784 A1 | 3/2022 |

OTHER PUBLICATIONS

Shockwave Medical—"Shockwave M5 IVL Catheter"—shockwavemedical.com [online]—Available at least as of Apr. 2022—Available from Internet <URL: https://shockwavemedical.com/clinicians/usa/peripheral/product-specs-resources/shockwave-m5/>.

Shockwave Medical—"Shockwave M5+"—shockwavemedical.com [online]—Available at least as of Apr. 2022—Available from Internet <URL: https://shockwavemedical.com/clinicians/usa/peripheral/product-specs-resources/shockwave-m5plus/>.

Shockwave Medical—"Shockwave S4 IVL Catheter"—shockwavemedical.com [online]—Available at least as of Apr. 2022—Available from Internet <URL: https://shockwavemedical.com/clinicians/usa/peripheral/shockwave-s4/>.

Marmur, Jonathan D.—"Carotid Artery Stenting"—marmur.com [online]—Available at least as of 2016—Available from Internet <URL: http://www.marmur.com/carotid-artery-stenting.html>.

Finol E.A., Siewiorek G.M., Scotti C.M., Wholey M.H., Wholey M.H.—"Wall Apposition Assessment and Performance Comparison of Distal Protection Filters"—Journal of Endovascular Therapy—May 2008—vol. 15, No. 2, p. 177-185—Available from Internet <URL: https://www.researchgate.net/publication/5427102_Wall_Apposition_Assessment_and_Performance_Comparison_of_Distal_Protection_Filters>.

Boston Scientific—"Peripheral Cutting Balloon™"—bostonscientific.com [online]—Available at least as of 2021—Available from Internet <URL: https://www.bostonscientific.com/en-us/products/catheters--balloon/peripheral-cutting-balloon.html>.

Philips—"AngioSculpt RX PTCA"—usa.philips.com [online]—Available at least as of 2021—Available from Internet <URL: https://www.usa.philips.com/healthcare/product/HCIGTDPTCARXSB/angiosculpt-rx-ptca-scoring-balloon-catheter>.

Cagent Vascular—"The Serration Balloon"—cagentvascular.com [online]—Available at least as of 2021—Available from Internet <URL: https://cagentvascular.com/information>.

Trireme Medical—"Chocolate® PTCA Balloon Catheter"—qtvascular.com [online]—Available at least as of 2021—Available from Internet <URL: https://qtvascular.com/us/products/chocolate-ptca/>.

BD (Becton, Dickinson and Company)—"Vascutrak™ PTA Dilatation Catheters"—bd.com [online]—Available at least as of 2021—Available from Internet <URL: https://www.bd.com/en-us/products-and-solutions/products/product-families/vascutrak-pta-dilatation-catheters>.

Boston Scientific—"FilterWire EZ™"—bostonscientific.com [online]—Available at least as of 2021—Available from Internet <URL: https://www.bostonscientific.com/en-US/products/embolic-protection/filterwire-ez-embolic-protection-system.html>.

Carefusion—"Introducing the AVAmax® vertebral balloon"—carefusion.com [online]—Available at least as of Apr. 1, 2010—Retrieved from Internet Archive Wayback Machine <URL: https://web.archive.org/web/20100401182423/http:/avamaxchoice.carefusion.com/>.

Abbott Laboratories—"Abbott Accunet—Model RX—Embolic Protection System"—medical-xprt.com [online]—Available at least as of 2021—Available from Internet <URL: https://www.medical-xprt.com/products/abbott-accunet-model-rx-embolic-protection-system-748573>.

Medtronic—"SpiderFX Embolic Protection Device"—medtronic.com [online]—Available at least as of 2021—Available from Internet <URL: https://www.medtronic.com/us-en/healthcare-professionals/products/cardiovascular/embolic-protection-devices/spiderfx.html>.

Contego Medical—"Corguard® Coronary Balloon Angioplasty System with Integrated Embolic Protection"—contegomedical.com [online]—Available at least as of 2021—Available from Internet <URL: https://contegomedical.com/coronary/>.

Contego Medical—"Paladin® Carotid PTA Balloon System with Integrated Embolic Protection"—contegomedical.com [online]—Available at least as of 2021—Available from Internet <URL: https://contegomedical.com/paladin-carotid-pta-balloon-system-us/>.

\* cited by examiner

INTRAVASCULAR LITHOTRIPSY

CROSS-REFERENCE TO RELATED APPLICATIONS

The entire contents of the following application are incorporated by reference herein: U.S. Provisional Patent Application No. 63/347,981; filed Jun. 1, 2022; and entitled INTRAVASCULAR LITHOTRIPSY.

The entire contents of the following application are incorporated by reference herein: U.S. Provisional Patent Application No. 63/381,487; filed Oct. 28, 2022; and entitled INTRAVASCULAR LITHOTRIPSY.

The entire contents of the following application are incorporated by reference herein: U.S. Provisional Patent Application No. 63/482,547; filed Jan. 31, 2023; and entitled INTRAVASCULAR LITHOTRIPSY.

The entire contents of the following application are incorporated by reference herein: U.S. patent application Ser. No. 18/322,562; filed May 23, 2023; and entitled INTRAVASCULAR LITHOTRIPSY.

BACKGROUND

Technical Field

The present disclosure relates to treatments for a calcified-plaque lesion in a patient's vasculature.

Description of Related Art

During an intravascular lithotripsy (IVL) procedure, a clinician uses a catheter configured to break apart calcified-plaque lesions within a patient's vasculature. Some such methods include the creation and rapid collapse of cavitation bubbles to create a shock wave which causes this calcification break-up.

SUMMARY

The present disclosure describes systems and techniques for producing and directing energy to create cavitation bubbles for fragmentation and/or disintegration of calcified lesions within a patient's vasculature. For purposes of illustration, the techniques herein are described primarily with respect to laser-based systems and respective applications thereof, such as coronary-vessel applications. However, it is to be understood that the techniques described herein may be assumed to be likewise applicable to similar systems based on other forms of energy, such as electrical-based systems and respective applications, such as peripheral-treatment applications, except where explicitly noted below.

In some examples, a medical device (e.g., see the medical device 12 as shown in FIG. 1) includes an elongated body (e.g., see the elongated body 302 as shown in FIG. 3) having a distal elongated body portion (e.g., see the distal elongated body portion 306 as shown in FIG. 3) and a central longitudinal axis (e.g., see the central longitudinal axis 308 as shown in FIG. 3). According to some examples, the medical device includes a balloon (e.g., see the balloon 204 as shown in FIG. 2) positioned along the distal elongated body portion, the balloon having an interior balloon surface (e.g., see the interior balloon surface 702 as shown in FIG. 7A) and an exterior balloon surface (e.g., see the exterior balloon surface 704 as shown in FIG. 7B) and configured to receive a fluid (e.g., see the fluid 212 as shown in FIG. 2) to inflate the balloon such that the exterior balloon surface contacts a calcified lesion (e.g., see the calcified lesion 50 as shown in FIG. 1) within a vasculature of a patient (e.g., see the patient 20 as shown in FIG. 1). The medical device may include one or more pressure wave emitters (e.g., see the pressure wave emitters 206 as shown in FIG. 2) positioned along the central longitudinal axis of the elongated body within the balloon, the one or more pressure wave emitters configured to propagate at least one pressure wave through the fluid to fragment the calcified lesion. In some examples, at least one of the pressure wave emitters includes an optical fiber (e.g., see the optical fiber 802 as shown in FIG. 8) configured to transmit laser energy into the balloon. According to some examples, the laser energy is configured to create a cavitation bubble in the fluid upon contact with the fluid to generate the at least one pressure wave.

The foregoing, and other features and advantages of the invention, will be apparent from the following, more particular description of the preferred embodiments of the invention, the accompanying drawings, and the claims.

BRIEF DESCRIPTION OF THE DRAWINGS

These and other features, aspects, and advantages are described below with reference to the drawings, which are intended to illustrate, but not to limit, the invention. In the drawings, like characters denote corresponding features consistently throughout similar embodiments.

DETAILED DESCRIPTION

Figure 1:
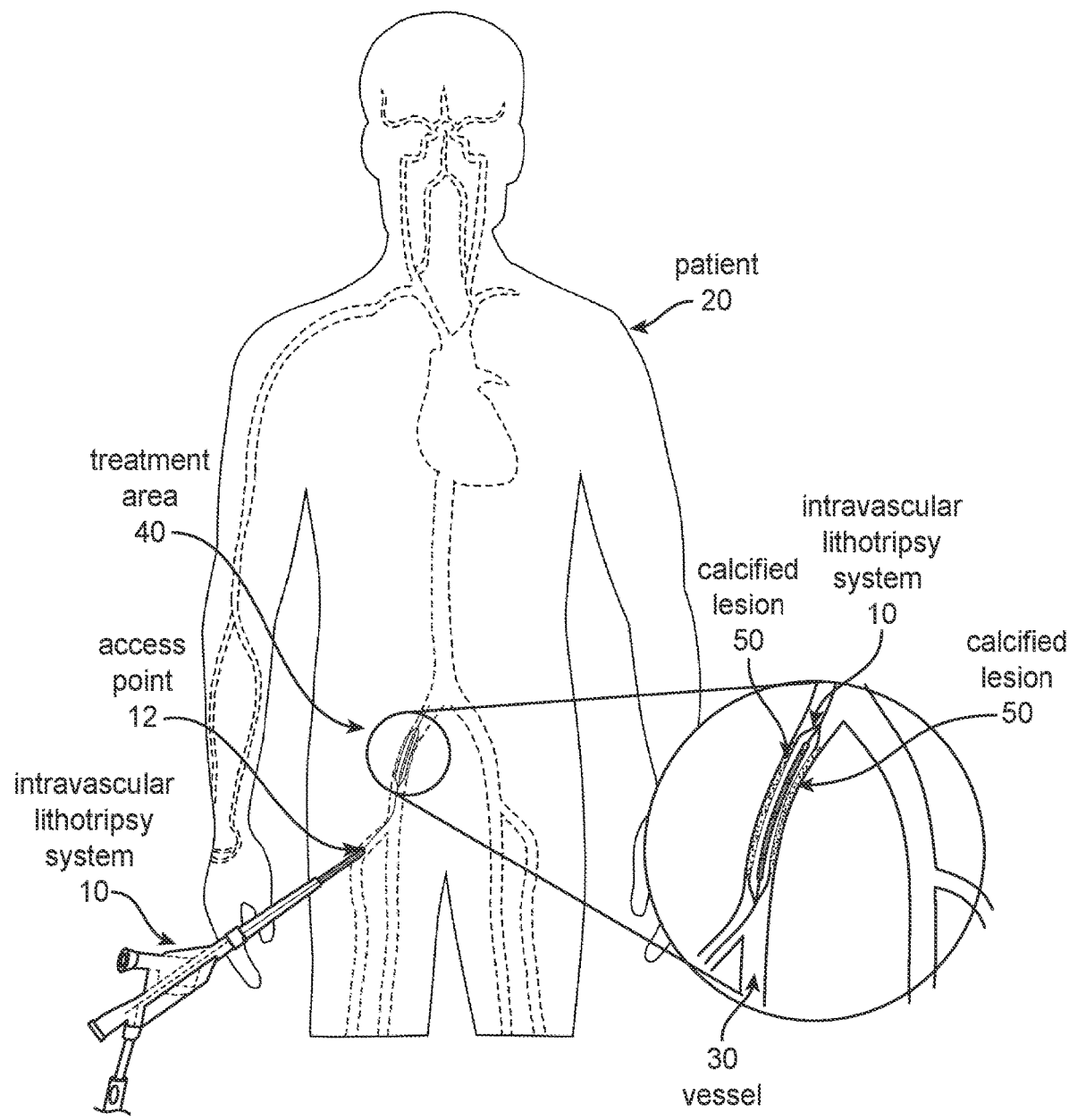
FIG. 1 illustrates a diagrammatic view of an intravascular lithotripsy (IVL) system as it may appear inserted into a patient's vasculature.

Although specific examples are disclosed below, inventive subject matter extends beyond the specifically disclosed examples to alternative examples and/or uses and modifications and equivalents thereof. Thus, the scope of the claims appended hereto is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations, in turn, in a manner that may be helpful in understanding specific examples; however, the order of description should not be construed to imply that these operations are order-dependent. Additionally, the structures, systems, and/or devices described herein may be embodied as integrated or separate components.

For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

During an intravascular lithotripsy (IVL) procedure, a clinician uses the formation and subsequent collapse of cavitation bubbles to generate high-energy pressure waves to disrupt calcified-plaque lesions within a patient's vasculature. Typical IVL procedures include the generation of shock waves through electrode emitters or electrode pairs. Such systems may have larger crossing profiles and increased manufacturing complexity.

Traditional IVL catheters also lack the capacity to finely control the directionality of the delivered energy. The use of fiber optics to create cavitation bubbles can help to rectify these detriments of prior art devices, as well as increase the delivered power, which can enhance the efficacy of the treatment, improve consistency of energy delivery, increase the durability of the IVL catheter as a whole, and decrease the manufacturing cost due to its lower complexity.

The present disclosure describes systems and techniques for producing and directing high-energy intravascular pressure waves for fragmentation and/or disintegration of calcified lesions within a patient's vasculature. For illustration purposes, the techniques herein are described primarily with respect to optical (e.g., laser) based systems and respective applications thereof, such as coronary-vessel applications. However, it is understood that the techniques described herein may be assumed to be likewise applicable to similar systems based on other forms of energy, such as electrical-based systems, and respective applications, such as peripheral-treatment applications, except where explicitly noted below. Additionally, while the treatment site is described as including calcified lesions throughout this specification, it is understood that the present disclosure also enables the treatment of restenotic lesions.

The systems described herein generally include an energy source, an IVL catheter having a distal IVL device, and an optical fiber. In some examples, the systems include an interventional balloon. During a lesion-disintegration procedure, a clinician may advance the interventional balloon to a target treatment site within a patient's vasculature and inflate the balloon with an inflation fluid, such as a saline/contrast-fluid mixture, until the balloon contacts at least a portion of the local vessel wall. The saline/contrast-fluid mixture is understood to include a viscosity suitable for the perpetration of cavitation bubbles through the introduction of electrical or optical energy. Because the saline/contrast-fluid mixture will often be mixed at the time of treatment, the ratio between saline and contrast-fluid may fluctuate. Still, laser-based energy delivery may be relatively insensitive to these changes. The clinician may then actuate the energy generator, causing the catheter to generate a cavitation bubble within the fluid-filled balloon, propagating a high-energy pressure wave through the balloon and the calcified lesion. A second pressure wave can also result from the subsequent collapse of the fluid cavitation, further destabilizing the internal structure of the lesion.

In examples that do not include an interventional balloon, the saline/contrast-fluid mixture is discharged into the patient's vasculature near the treatment site to displace the blood in the local area. Once this saline/contrast-fluid mixture has at least partially displaced the blood in this area, the clinician may actuate the energy generator, causing the catheter to generate a cavitation bubble in the region of the saline/contrast-fluid mixture, propagating a high-energy pressure wave through this region and into the calcified lesion.

Additional examples, both with and without an interventional balloon, include the introduction of a photosensitive agent into the saline/contrast-fluid mixture. This photosensitive agent may provide a target for the energy source to aim toward, permitting greater control of where the cavitation bubble is formed within the interventional balloon and/or the saline/contrast-fluid mixture that has displaced blood in the local area.

"Superheating" as used herein means to heat a liquid, under pressure, above its boiling point without vaporization. In some examples, the device as disclosed in this application does not superheat the fluid within the balloon in order to form cavitation bubbles. In alternative examples, the device of this disclosure does superheat the fluid within the balloon in order to form these cavitation bubbles.

Figure 2A:
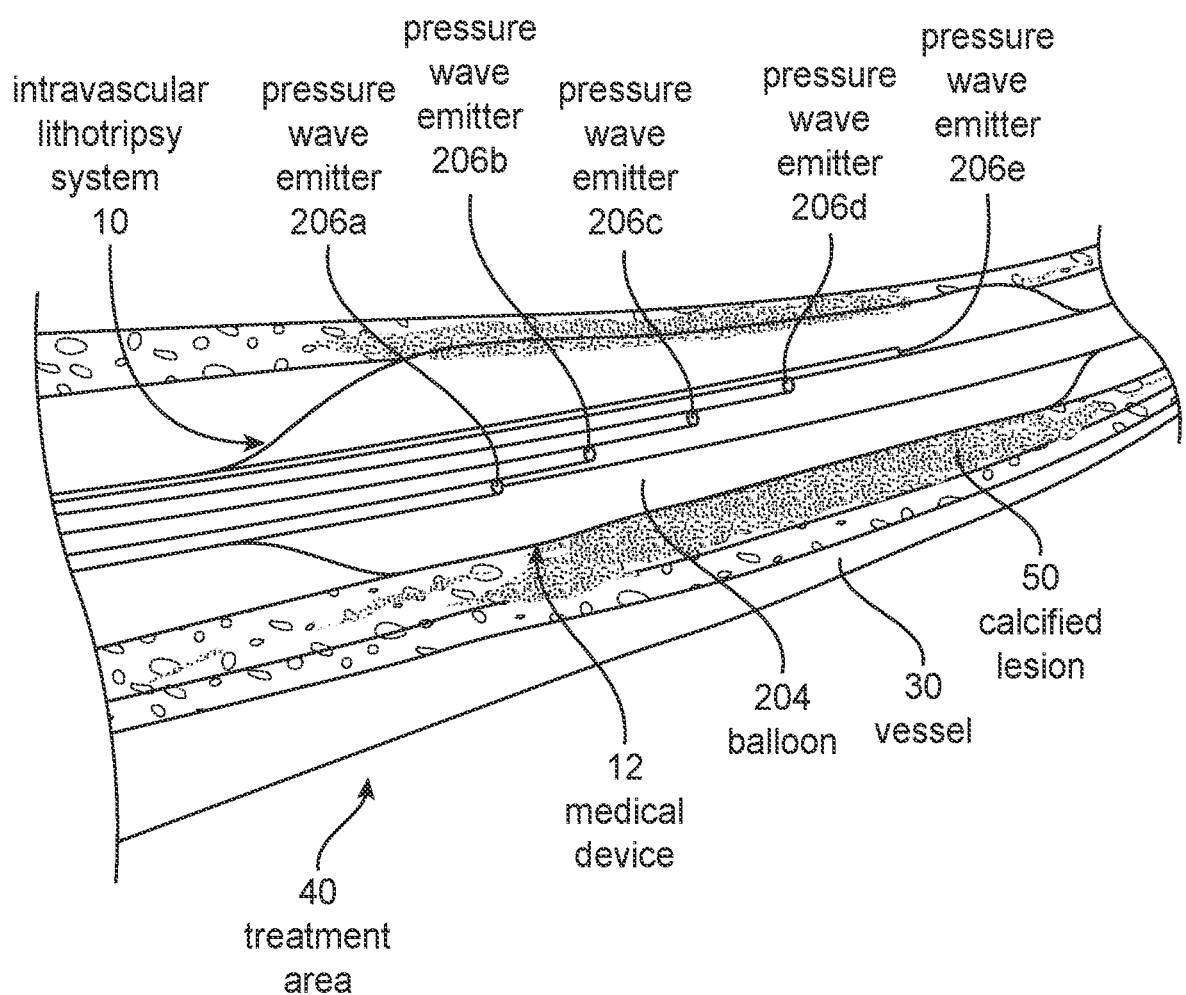
FIGS. 2A and 2B illustrate two diagrammatic views of a medical device in or near a calcified lesion in a vessel.
Figure 2B:
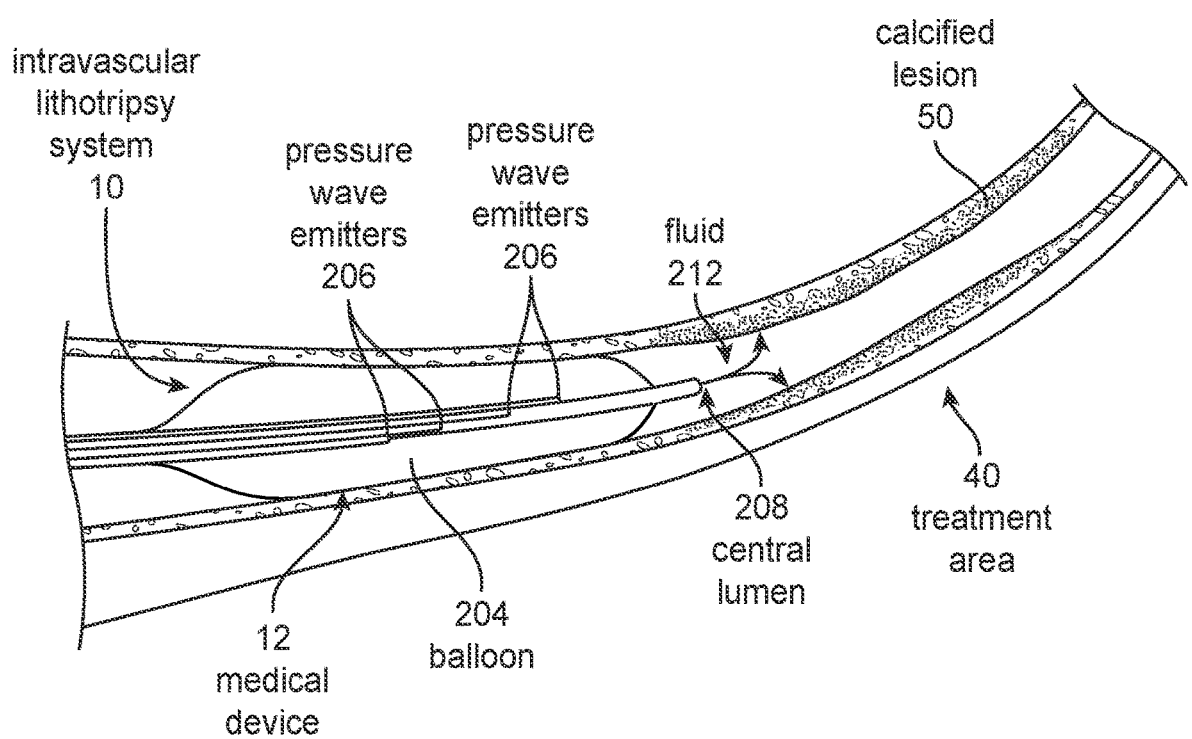

FIG. 1 illustrates a diagrammatic view of an intravascular lithotripsy (IVL) system 10 as it may appear inserted into a patient's vasculature. The IVL system 10 may include a medical device 12, perhaps including an interventional balloon, as depicted in later figures. During a lesion-disintegration procedure, a clinician may advance the medical device through an access point 14 in the patient 20, such as the femoral or common femoral arteries, as depicted in FIG. 1. Other access points may include the radial artery, tibial artery, pedal artery, axial artery, peroneal artery, etc. The medical device 12 may then be advanced through the vasculature of the patient 20 until it reaches the vessel 30 containing the treatment area 40. For IVL, the treatment area may include a calcified lesion 50. FIGS. 2A and 2B show a close-up view of two examples of IVL systems located in or adjacent to the treatment area 40 including a calcified lesion 50.

Figure 10A:
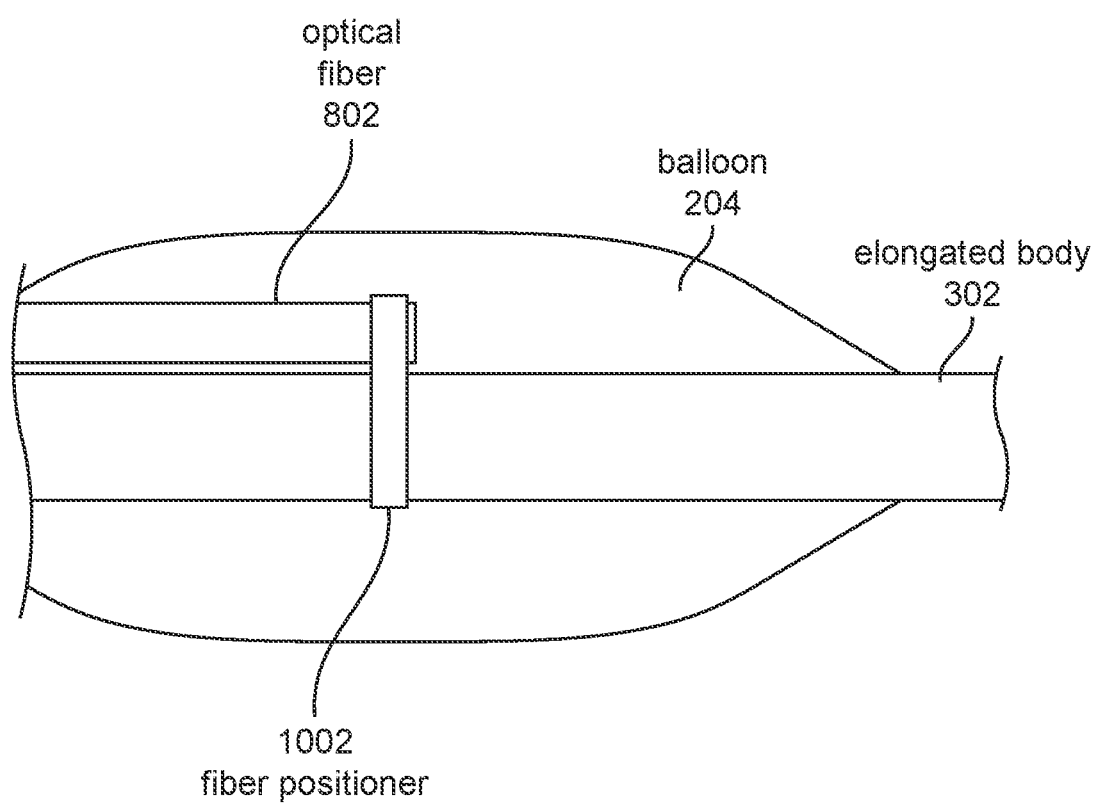
FIGS. 10A, 10B, 10C, and 10D illustrate diagrams of an IVL device with the distal fiber end of an optical fiber held in place with or without targets of various-shaped profiles.

FIG. 2A illustrates a diagrammatic view of a medical device 12 within a treatment area 40 including a calcified lesion 50 in a vessel 30. In this example, the medical device 12 includes a balloon 204. During an IVL procedure, the clinician may inflate the balloon 204 so that it physically contacts at least a portion of the calcified lesion 50 and the wall of the vessel 30 in the treatment area 40. This inflation of the balloon 204 may include using a saline/contrast-fluid mixture for propagating pressure waves or "shock waves" when superheated by a laser. This saline/contrast-fluid solution may be any percentage ratio, as no discernable difference has been observed during testing. While any saline/contrast-fluid solution may be used, it may be desirable to include at least a small percentage of contrast-fluid in said solution, as saline does not show up under fluoroscopic guidance, and thus would not indicate the inflation, or issues with the inflation, to an operator. As will be discussed in FIGS. 10A-10B, specific wavelengths of laser energy may be capable of superheating the saline/contrast-fluid mixture without assistance (FIG. 10A). Still, other wavelengths are less absorptive in saline/contrast-fluid mixtures and may necessitate a target block that will superheat and cause the deployment of the pressure waves.

Also shown in FIG. 2A is a central lumen 208 located within an elongated body (302 below). Along the elongated body 302 are pressure wave emitters 206. As shown in FIGS. 2A and 2B, five pressure wave emitters (206a, 206b, 206c, 206d, and 206e) are present in the medical device 12. While five pressure wave emitters 206 are illustrated in FIGS. 2A and 2B, the emitter 206 array of the medical device 12 may include as few as one individual emitter unit 206 and up to as many emitter units 206 as could reasonably fit within the balloon 204. It is also to be noted that individual emitter units 206 are also referred to throughout this disclosure as "emitters" 206 (e.g., in reference to an emitter unit 206 as a whole).

FIG. 2B illustrates a diagrammatic view of a medical device 12 adjacent to a treatment area 40 including a calcified lesion 50 in a vessel 30. The medical device 12, balloon 204, and the pressure wave emitters 206 may be similar to those described in FIG. 2A. However, the central lumen 208 of the elongated body 302 in FIG. 2B is shown as deploying or injecting a fluid 212 into the treatment area 40. This fluid 212 may displace blood in the treatment area 40 prior to inserting the medical device 12 into the treatment area 40, facilitating the expansion of the balloon 204 and increasing the efficacy of the IVL procedure.

Figure 3:
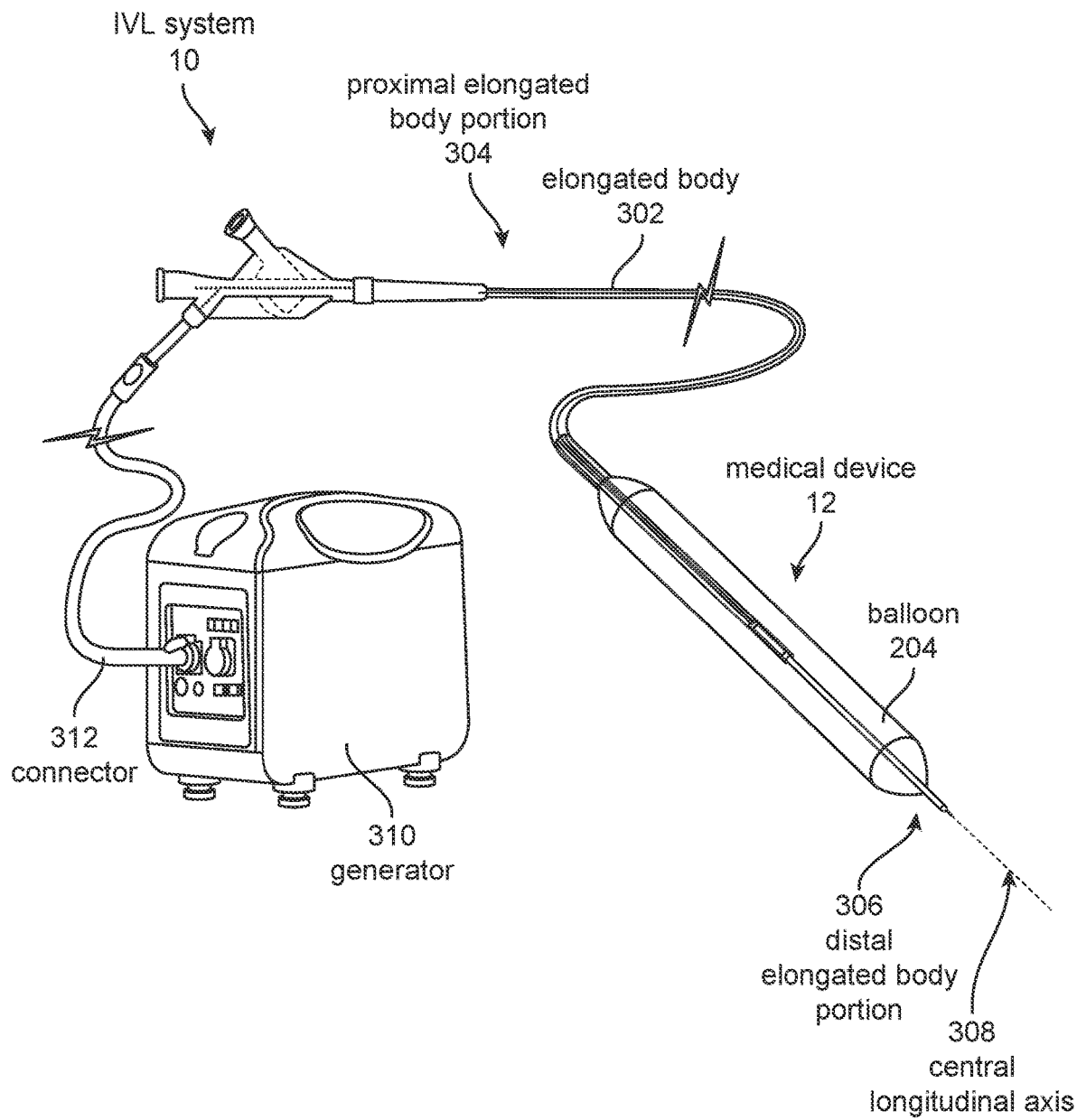
FIG. 3 is a diagram illustrating an IVL system.

FIG. 3 is a diagram illustrating an IVL system 10. As shown in FIG. 3, IVL system 10 may include at least an energy generator 310 and an elongated body 302 removably coupled to the energy generator 310, such as via an electrical connector 312. The elongated body 302 may include a medical device 12 positioned at a distal elongated body portion 306. In some examples, the elongated body 302 is configured to navigate a tortuous vasculature of a patient 20 toward a target treatment site 40, e.g., a calcified-plaque lesion 50 within a vessel 30.

While the term "elongated body" is used throughout the present specification, it is understood that an elongated body may refer to a catheter, such as an IVL catheter. Additionally, while the connector 312 is described as an electrical connector 312 in the description of FIG. 3, it is understood that the connector 312 may also be an optical connector 312. In fact, in some examples, the IVL system 10 may not necessitate an electrical connector 312. In these examples, a therapy button may be present on the console, and there may be no electrical interrogation of the catheter itself. While an electrical connector 312 may not be necessary in all examples, an optical connector 312 is necessary in order to provide the laser energy to the catheter.

As shown in FIG. 3, the medical device 12 may include a fluid-inflatable interventional balloon 204 and a pressure wave emitter 206 array, shown but not labeled due to size constraints, positioned within the balloon 204. The emitter 206 array may include one or more individual emitter units 206. For instance, the interventional balloon 204, or a distal elongated body portion 306 passing therethrough, may define a central longitudinal axis 308, and emitter units 206 may be distributed longitudinally along the central longitudinal axis 308.

Each emitter unit 206 is configured to receive energy from the energy generator 310 and use the received energy to generate and transmit high-energy pressure waves through the balloon 204 and across a treatment site. As detailed further below, the energy generator 310 may generate and transmit energy in the form of electrical energy, optical energy, or a combination thereof. For instance, the emitter unit(s) 206 may use the received energy to generate a cavitation bubble 1404 within the fluid inside the balloon 204, propagating one or more high-energy pressure waves radially outward through the balloon and the calcified lesion.

Figure 8:
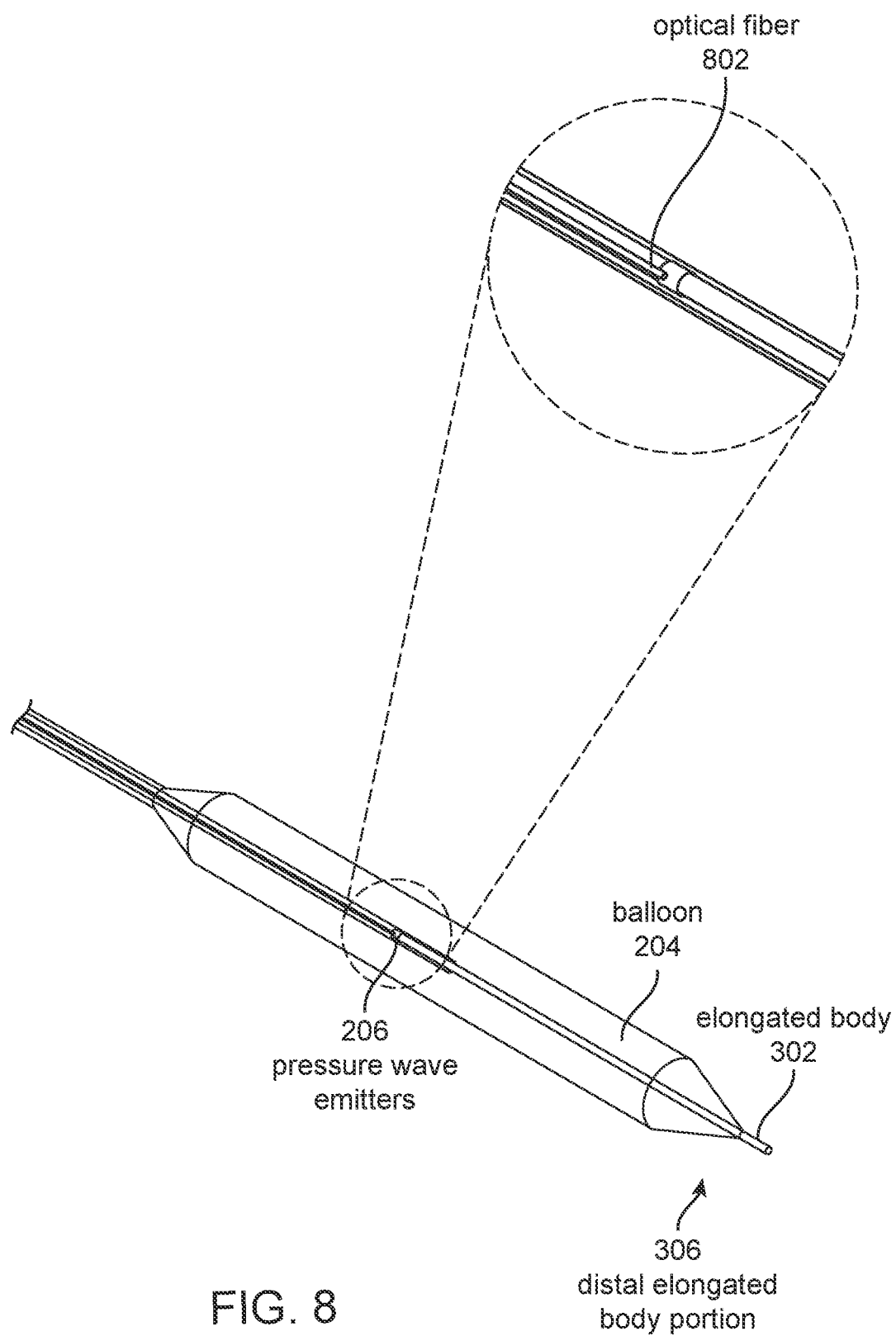
FIG. 8 illustrates a perspective view of the IVL balloon, along with an inset view illustrating a position for the distal fiber end of an optical fiber according to the IVL catheter of FIG. 6.

In some cases, but not all cases, a secondary set of high-energy pressure waves can subsequently result from the collapse of the fluid cavitation bubble 1404 (as shown in FIG. 14), further destabilizing the internal structure of the calcified-plaque lesion. In some examples, one or more emitters 206 can include an optical-based emitter 206 configured to receive a high-energy optical (e.g., light) signal from the generator 310, such as via one or more optical fibers 802 (as shown in FIG. 8), and direct the optical signal to trigger the initial cavitation. Additionally, one or more emitters 206 can include an electrical-based emitter 206 configured to receive electrical energy from the generator 310, such as via one or more conductive wires, and generate a spark between a pair of electrodes, thereby triggering the initial cavitation.

According to some examples, a cooling mechanism functions in tandem with the energy generator 310. However, flashlamp systems may provide energy to the optical fibers 802 without necessitating said cooling mechanism. Additionally, diode systems may be used as an alternative to flashlamp systems, which may also not require a cooling mechanism.

Figure 4:
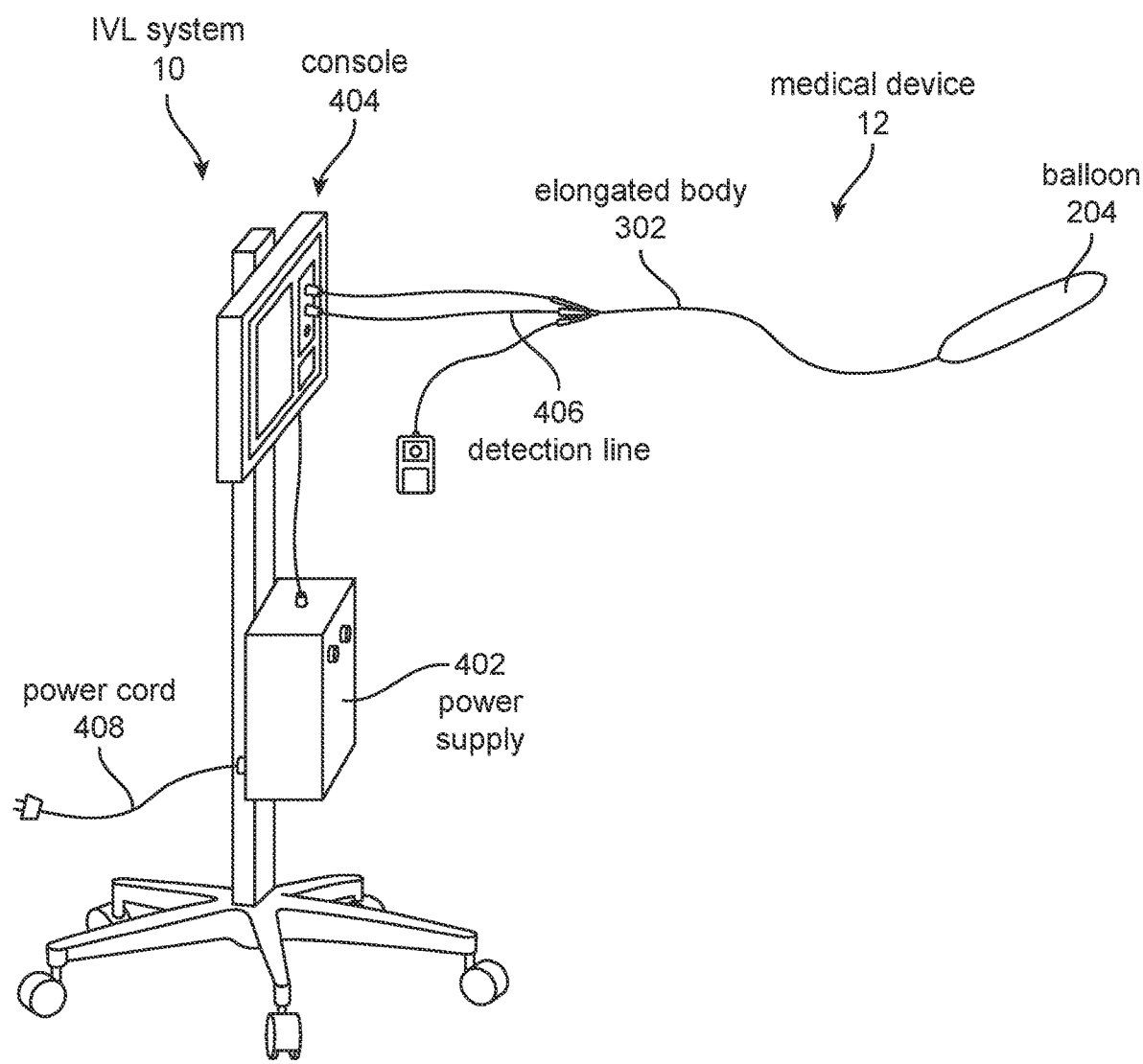
FIG. 4 illustrates an embodiment of the IVL system of FIG. 3 as it may appear in a use-case scenario.

FIG. 4 illustrates an embodiment of the IVL system 10 of FIG. 3 as it may appear in use. A medical post may be provided to facilitate movement of the IVL system 10 between rooms as necessary. A power supply 402 may be situated near the base of the medical post, coupled to a power cord 408 for receiving wall power or power from a generator 310, as well as an umbilicus for electrically coupling to a console 404. As shown in FIG. 4, the console 404 allows a user, such as a clinician, to operate the IVL system 10. The elongated body 302 may be coupled to the console 404 via a power cable for receiving energy from the power supply 402 to transmit energy to the emitters 206 within the IVL balloon 204. A separate line dedicated to the inflation of the IVL balloon 204 may also be present.

According to some examples, a detection line 406 is present. The detection line 406 may offer a few methods of providing feedback about the integrity of the individual components within the IVL balloon 204. For instance, a safety pressure sensor may be provided. If a sudden pressure drop is detected, a failure may have occurred, such as a rupture of the IVL balloon 204. This suggests to the clinician that the procedure should be halted, and the IVL balloon 204 should be retrieved immediately and safely from the patient's vasculature. According to some examples, once a pressure sensor in the IVL balloon 204 detects a balloon 204 rupture, energy emission through the elongated body 302 may be halted immediately. It is understood that the term "halted" may be used to issue an error code to the operator for a manual shutdown or an auto-system shut-off.

Additionally, the pressure sensor may be present anywhere within the pressure pathway, wherein the pressure pathway defines a path beginning at the generator and ending at the balloon 204. In some examples, the pressure sensor may be within the generator 310. According to some examples, the pressure sensor may be within a hub, which is the intermediary component connecting the elongated body 302 to the generator 310 (in examples including a separate generator 310). The pressure sensor may be present within the elongated body 302. In some examples, as described in the preceding paragraph, the IVL balloon 204. The pressure sensor may be present outside of these distinct components (generator 310, hub, elongated body 302) but within the pressure pathway.

Furthermore, in some examples, the pressure sensor may be present anywhere within the IVL system 10, including outside of the previously described pressure pathway. This could include a separate device outside of the medical device 12, such as an inflation device which is either a part of, or attached to, a hub connector. This inflation device may be adjacent, but outside of, the guidewire lumen 208. The pressure sensor may be a part of or attached to, such an inflation device.

Additionally, a fiber interrogation mechanism may be present. According to some examples, the purpose of the fiber interrogation mechanism is to sense or detect if the optical fiber, or at least one of the optical fibers 802 (see FIG. 8), has broken, or in other ways become disconnected. This may be achieved by reflecting at least a portion of the energy back down the optical fiber 802 once a pulse has been emitted, and any obstruction of this return pulse would indicate to the clinician that something has gone awry, and the IVL balloon 204 should be retrieved, and the issue fixed.

Figure 5:
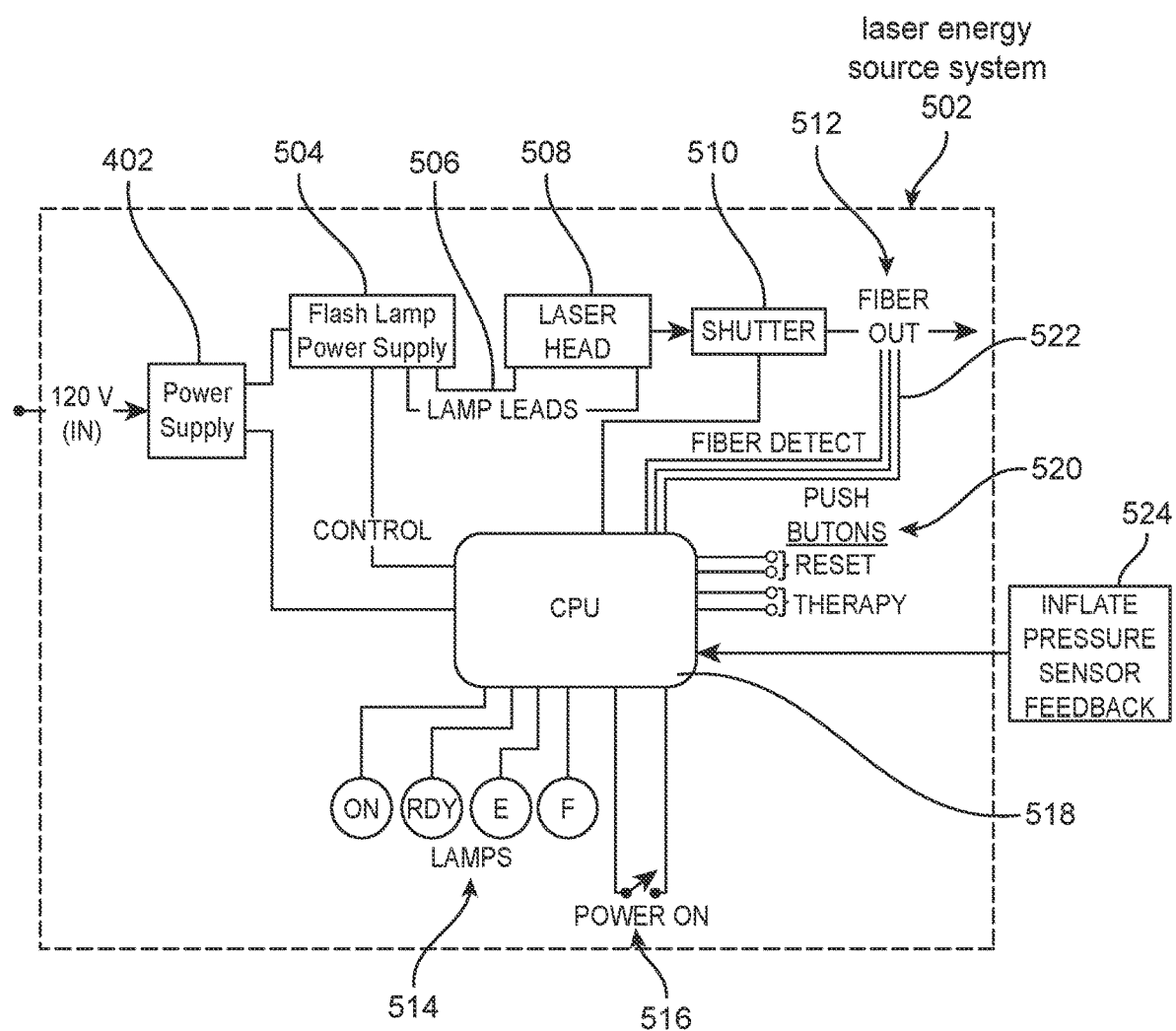
FIG. 5 illustrates a block diagram of the laser energy source system, such as the generator of FIG. 1, according to some examples.

FIG. 5 illustrates a block diagram of the laser energy source system 502, according to some examples. As can be seen by the dotted line surrounding a majority of the components, the laser energy source system 502 includes an energy source. Power, such as power from a wall, as shown by the arrow leading through the 120 V (IN), may be provided to the power supply 402 within the energy source. The power supply 402 provides power to a flashlamp power supply 504 and a central processing unit (CPU) 518. The flashlamp power supply 504 may be controlled by the CPU 518.

The CPU 518 includes a user interface, which may involve tactile buttons and switches or other means of user communication, such as a touch screen. A power on switch 516 is shown in electronic communication with the CPU 518, as well as push buttons 520 for resetting the CPU 518 (reset) and initiating the treatment once the elongated body 302 is in place (therapy). The CPU 518 also controls the lamps 514 (On, RDY (Ready), E (Emission), and F (Fault)). The on lamp 514 indicates that the system 502 is turned on. The RDY lamp 514 indicates that the system 502 is connected and ready to actuate the laser energy. The E lamp 514 indicates that the laser energy is currently active. The F lamp 514 indicates that a fault has occurred, and the system 502 needs to be reset. In IVL systems 10, including safety features such as a safety pressure sensor as described above, the CPU 518 receives this feedback from the pressure sensor 522, which, as it is located in the IVL balloon 204, exists outside of the energy source.

The flashlamp power supply 504 includes lamp leads 506 that electrically couple the flashlamp power supply 504 to a laser head 508. The laser head 508 is aimed at a shutter 510, which is in electronic communication with and controlled by the CPU 518. The shutter 510 is an additional safety to prevent premature emission of the laser through the elongated body 302. The shutter 510 is commanded by the CPU 518 just prior to triggering the flashlamp, which initiates the laser energy. In the case of a laser source such as an excimer laser, the trigger for the shutter 510 may be a high-voltage switch and not a flashlamp. The shutter 510 separates the laser head 508 from the optical fibers 802, as indicated by the fiber out 512. The optical fibers 802 then travel the length of the elongated body 302 to the treatment site. In IVL systems 10, including safety features such as a fiber interrogation mechanism described above, the CPU 518 receives feedback from the optical fiber 802 through the fiber interrogation mechanism 524, as shown. Because the fiber interrogation mechanism may operate from anywhere along the fiber line (a break anywhere in the line can be detected anywhere else along the line, as long as the detection is occurring prior to the break), the fiber interrogation mechanism 524 is shown as being conveniently located within the energy source.

Figure 6:
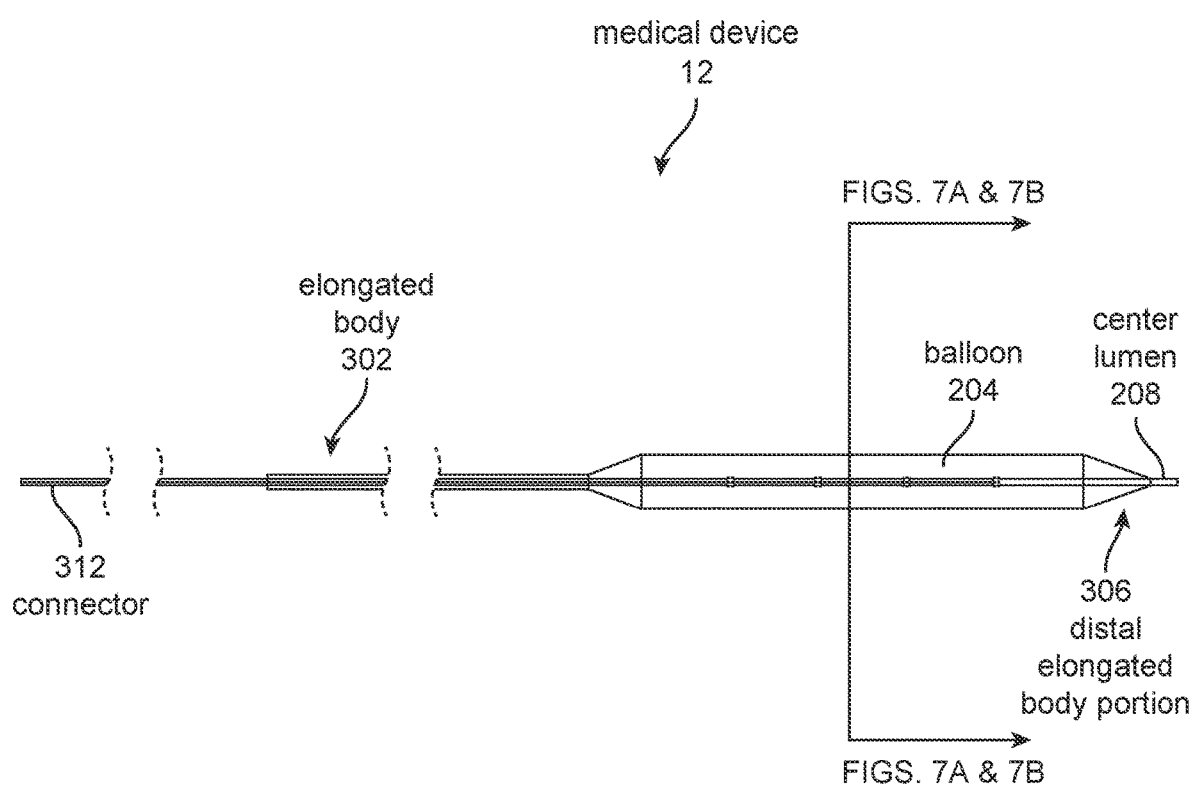
FIG. 6 illustrates a side view of an example IVL catheter, including the IVL balloon at the distal end and the connector for coupling the IVL catheter to a generator.

FIG. 6 illustrates a side view of an example elongated body 302, including the IVL balloon 204 at the distal elongated body portion 306 and the connector 312 for coupling the elongated body 302 to a generator 310. In some examples, the elongated body 302 includes an inner shaft and an outer shaft surrounding the inner shaft. The inner shaft may include a guidewire lumen 208, or another type of lumen 208, depending on the clinician's needs.

According to FIG. 6, an IVL balloon 204 may be present. The IVL balloon 204 may be inflated with a saline/contrast-fluid mixture when the elongated body 302 has been advanced to the treatment site. Within the IVL balloon 204 is at least one emitter. As described previously, as few as a single emitter 206 may be present (as described in FIGS. 14A, 14B, 16A, and 16B), or a multitude of emitters 206 may be present (as shown in greater detail in FIGS. 18A, 18B, and 18C).

According to some examples, a single emitter, such as an optical fiber, may be scored to create multiple locations of light or signal emission for the laser, causing a single optical fiber 802 to act functionally as a multitude of emitters 206. Such an embodiment is explored in greater detail in FIGS. 14A and 14B.

At the proximal elongated body portion 304, the connection point between the elongated body 302 and generator 310 can be seen. This connection point may occur through direct coupling of the elongated body 302 to the generator 310 or an adaptor suited to couple one end to the elongated body 302 and the opposing end to the generator 310. At this proximal elongated body portion 304, a fiber bundle may also be present in examples where multiple fibers 802 are utilized as emitters 206. This fiber bundle is in optical communication, or optically coupled, to the generator 310 to provide laser energy to the optical fibers 802 that will be emitted into the fluid-filled IVL balloon 204.

As disclosed previously, in some examples, the IVL balloon 204 may not be present nor necessitated for the elongated body 302. In these embodiments, the inner shaft may include a lumen 208 configured to deliver the saline/contrast-fluid mixture to the treatment area of the vasculature. Introducing this saline/contrast-fluid mixture may displace the local blood of this vasculature, thus permitting the energy emitted by the optical fibers 802 to create cavitation bubbles 1404 without the need for an external structure like the IVL balloon 204.

Figure 7A:
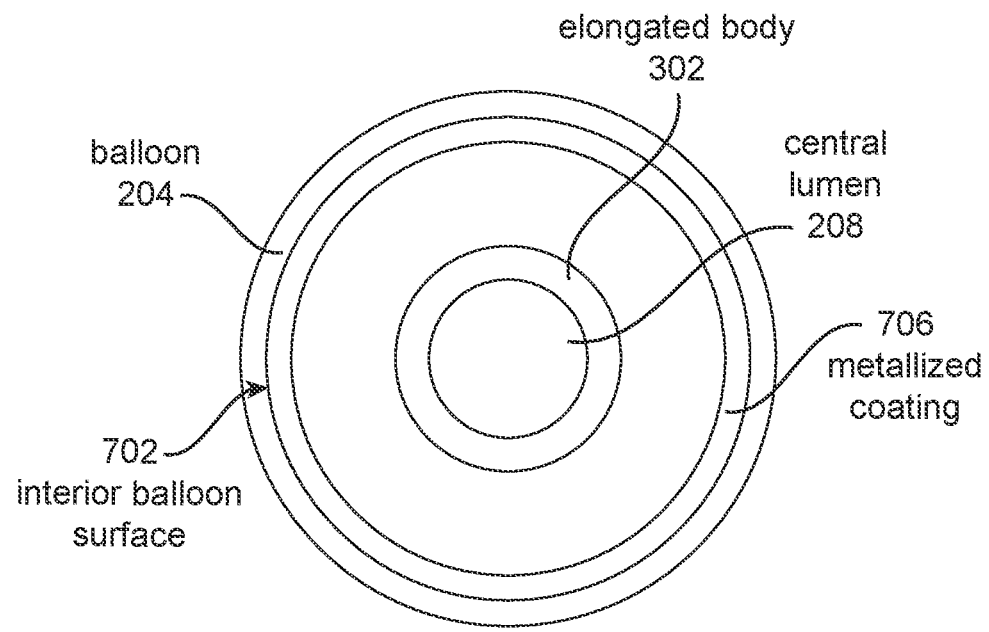
FIGS. 7A and 7B illustrate two cross-sectional views of the medical device in FIG. 6.
Figure 7B:
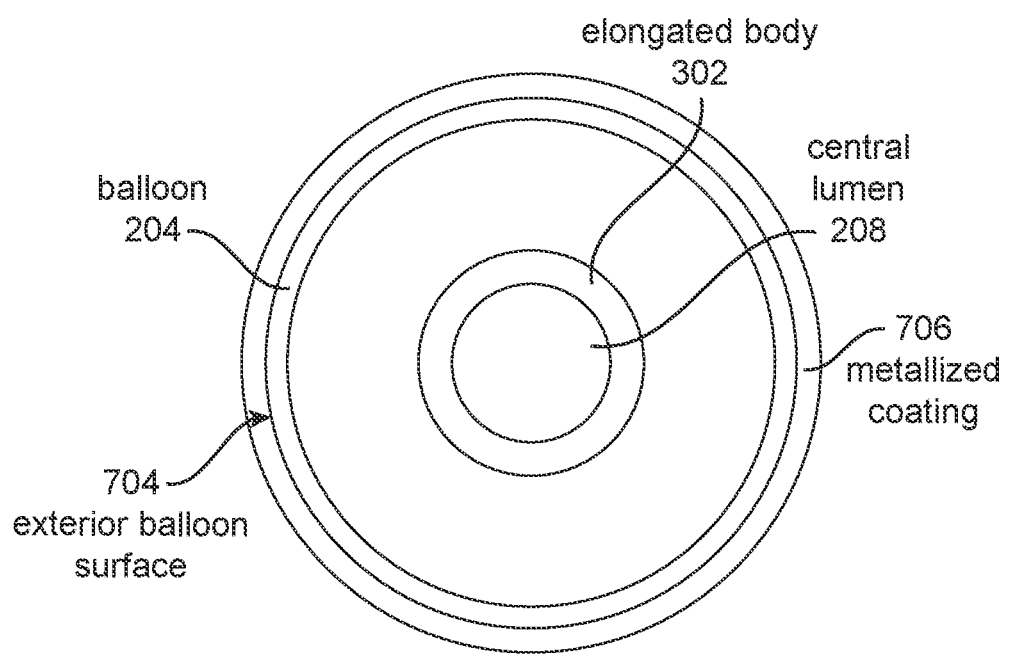

FIGS. 7A and 7B illustrate two cross-sectional views of the medical device 12 of FIG. 6. Specifically, FIG. 7A illustrates a balloon 204 having a metalized coating 706 on the interior balloon surface 702 and FIG. 7B illustrates a balloon 204 having a metalized coating 706 on the exterior balloon surface 704. Both FIGS. 7A and 7B also show the elongated body 302 and the central lumen 208. The radii and proportions of each feature are exaggerated to simplify the expression of each independent structure in the drawing.

The metalized coating 706 may be configured to increase the damage threshold of the balloon 204 from laser energy. That is to say, the resistance of the balloon 204 from perforating and collapsing due to too much laser energy may increase because of a present metalized coating 706 on either the interior balloon surface 702 or the exterior balloon surface 704. The metalized coating 706 may also offer additional safety, in case of balloon 204 failure or deflation. This metalized coating 706 may prevent the optical fiber (802 below) from contacting or penetrating the balloon 204. Without additional safety measures, should the balloon be perforated during a procedure, there is the potential for pieces of the balloon to be unintentionally left in situ, which might then migrate through the patient's vessels. Furthermore, this additional measure may facilitate the prevention of unwanted balloon deflation.

This metalized coating 706 may be created from aluminum, nickel, chromium, gold, alloys, a dielectric reflective coating, and the like. It is understood that this list of metalized coatings 706 is not comprehensive, and equivalent metalized coatings 706, while not named herein, may be used. The metalized coating 706 may be deposited in extremely thin layers. These layers may be only a few microns thin, making the metalized coating 706 almost transparent, and permitting the slimmest change possible to the thickness of the balloon 204 while also garnering the benefits listed herein.

In both FIGS. 7A and 7B, the metalized coating would not significantly change the compliance or any other balloon properties. The additional thickness added to the balloon 204 may depend on whether the metalized coating 706 is on the interior balloon surface 702 or the exterior balloon surface 704. For instance, in FIG. 7A, the metalized coating 706 may be folded, which could increase the thickness of the balloon 204 by up to two times. In FIG. 7B, an additional layer may be situated outside the metalized coating 706 on the exterior balloon surface 704 to prevent particulate migration. This could suggest an increase in the thickness of the balloon 204 by up to six times.

FIG. 8 illustrates a perspective view of the IVL balloon 204 and an inset view illustrating a position for the distal fiber end (1402 below) of an optical fiber 802 according to the elongated body 302 of FIG. 6. In this example, and the examples following, any present optical fibers 802 act as the pressure wave emitters 206 as detailed in previous figures. According to the example of FIG. 8, a protective sleeve may contain the inner shaft and/or any present lumens 208 and protect these surfaces from any energy emissions from the distal fiber end 1402 of the optical fibers 802. While not shown in the figures, the optical fiber 802 may include a toe or blunt feature on its terminal portion to prevent accidental perforation of the balloon 204 by the optical fiber 802. It is understood that such a toe or blunt feature would not impede the passage of laser energy from the distal fiber end 1402.

Figure 9A:
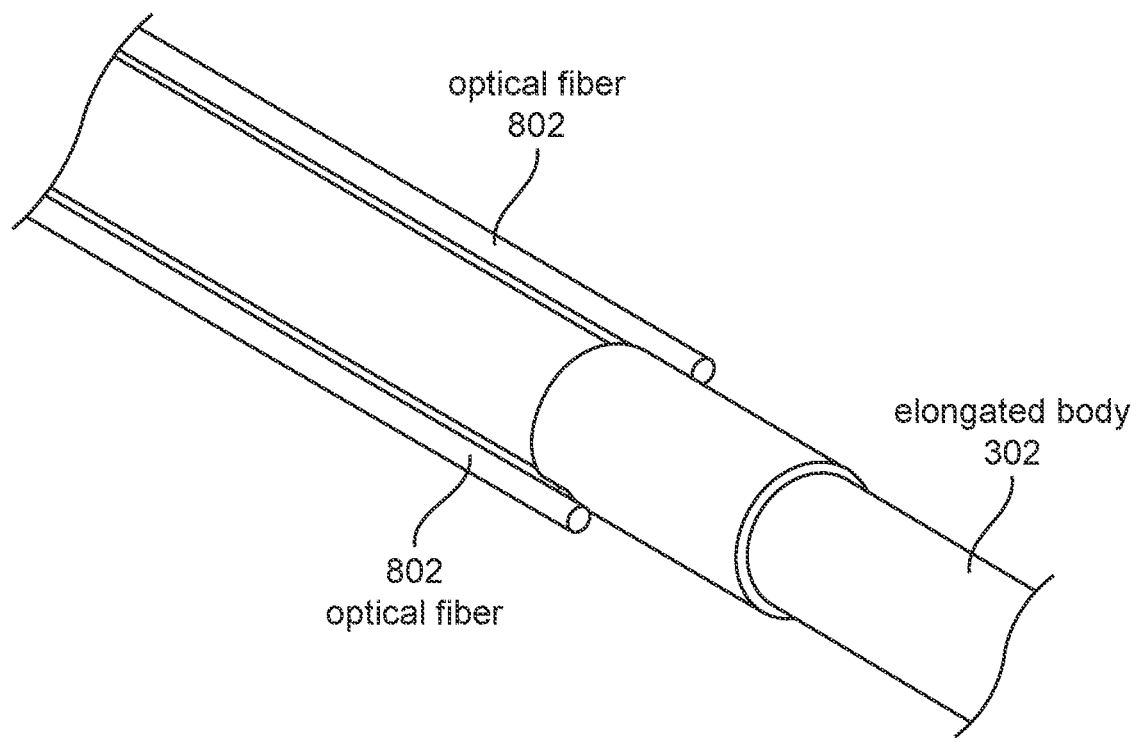
FIGS. 9A and 9B illustrate perspective views of a portion of the IVL catheter at the distal fiber end of two optical fibers, according to some examples.
Figure 9B:
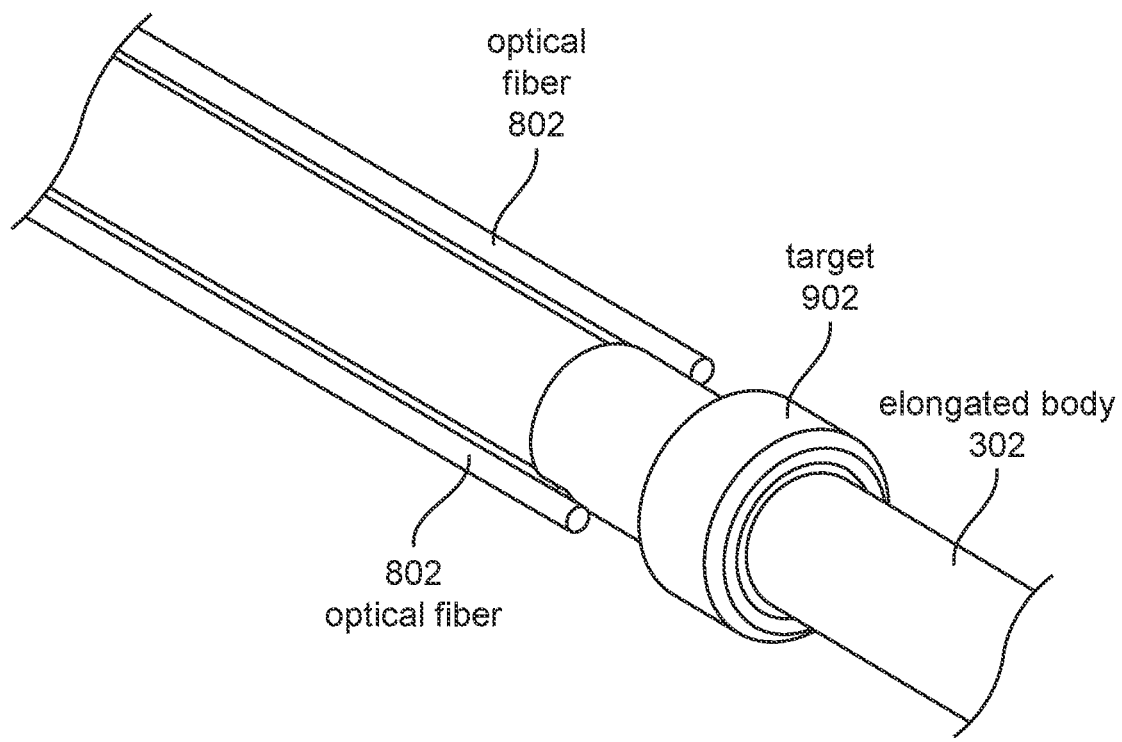

FIGS. 9A and 9B illustrate perspective views of a portion of the elongated body 302 at the distal fiber end 1402 of two optical fibers 802, according to some examples. At least one optical fiber 802 may terminate at least partially adjacent to a target 902. In situations of shorter wavelength emissions, such as an Nd:YAG laser, the target 902 may provide a safety feature, and a component in the formation of cavitation bubbles 1404.

As far as safety is concerned, the higher energy provided by an Nd:YAG laser, after causing cavitation, may proceed into a patient's vasculature if left uninterrupted. In such situations, and at high enough energy levels, this may be detrimental to the patient. The target 902 can prevent the energy from surpassing the boundaries of the IVL balloon 204 and/or the effective treatment area in situations where no IVL balloon 204 is provided.

As for the formation of cavitation bubbles 1404, the target 902 may receive the energy emitted by the optical fiber 802 and begin to heat up. As the target 902 heats up further, a cavitation bubble 1404 may be formed on the target 902. In this scenario, the wavelength of the laser is not, nor is it intended to be, absorbed by the saline/contrast fluid mixture, as all of the energy may be delivered into the target 902 to facilitate the creation of the superheated cavitation bubbles 1404 on the surface of target 902 due to the subsequent heating of the surrounding saline/contrast fluid mixture.

FIGS. 10A, 10B, 10C, and 10D show diagrams of a medical device 12 having an IVL balloon 204 with the distal fiber end 1402 of an optical fiber 802 held in place by a fiber positioner 1002 while aimed at a target 902.

Figure 10B:
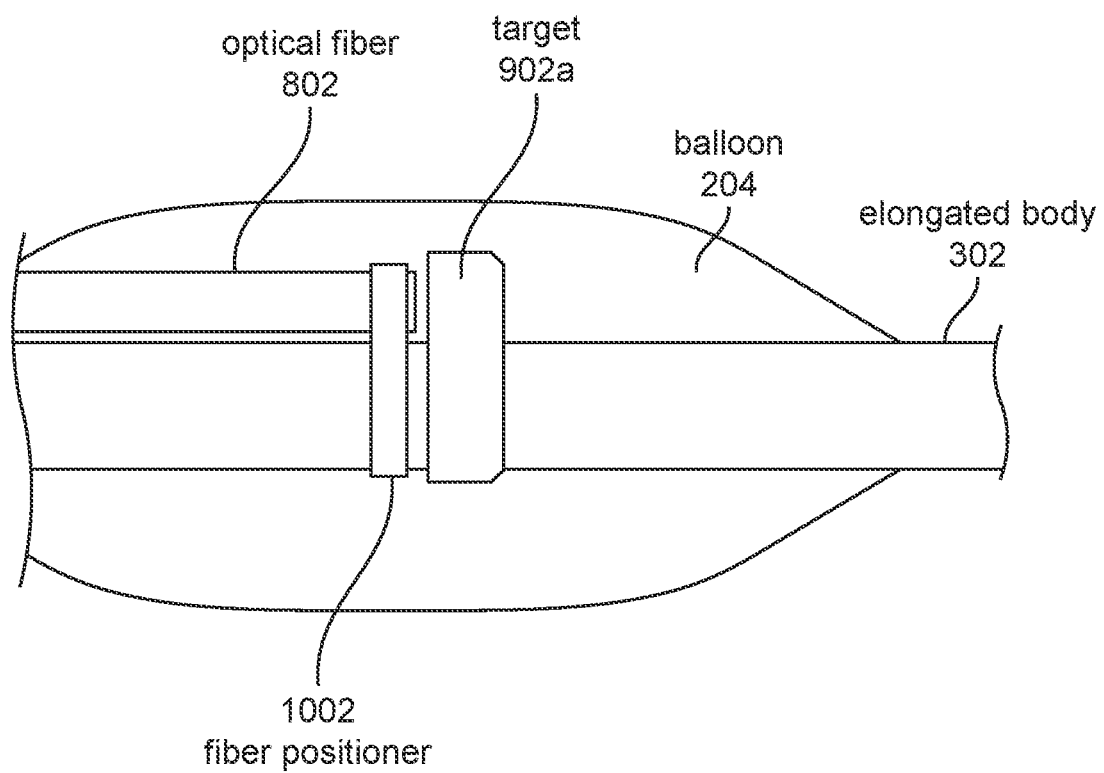
Figure 10C:
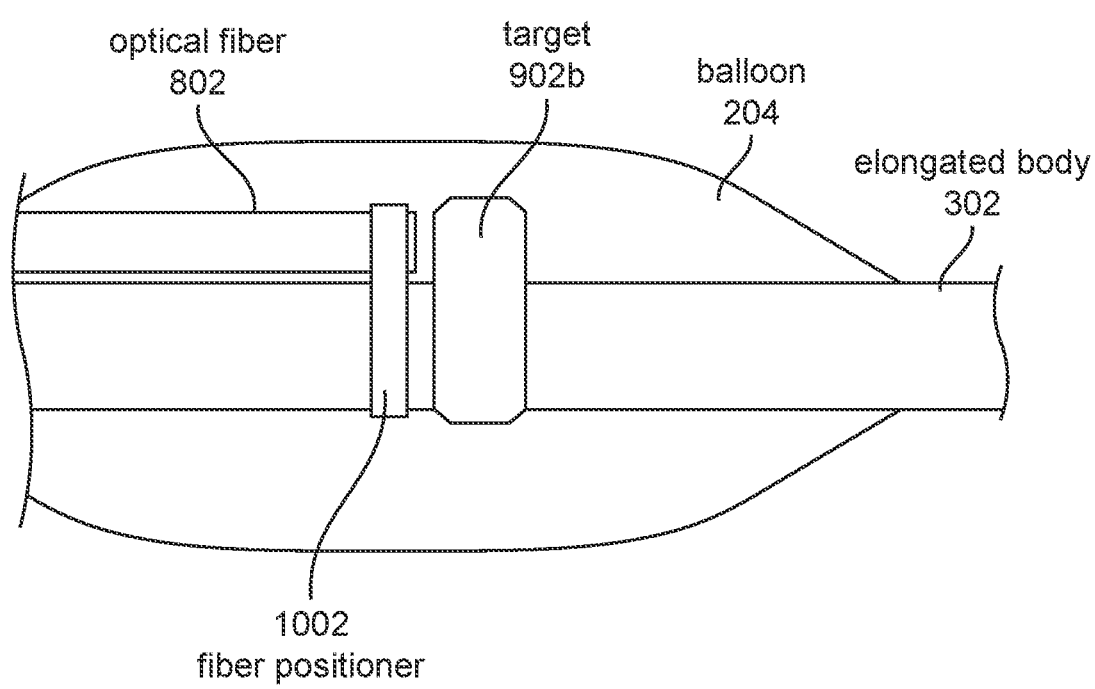
Figure 10D:
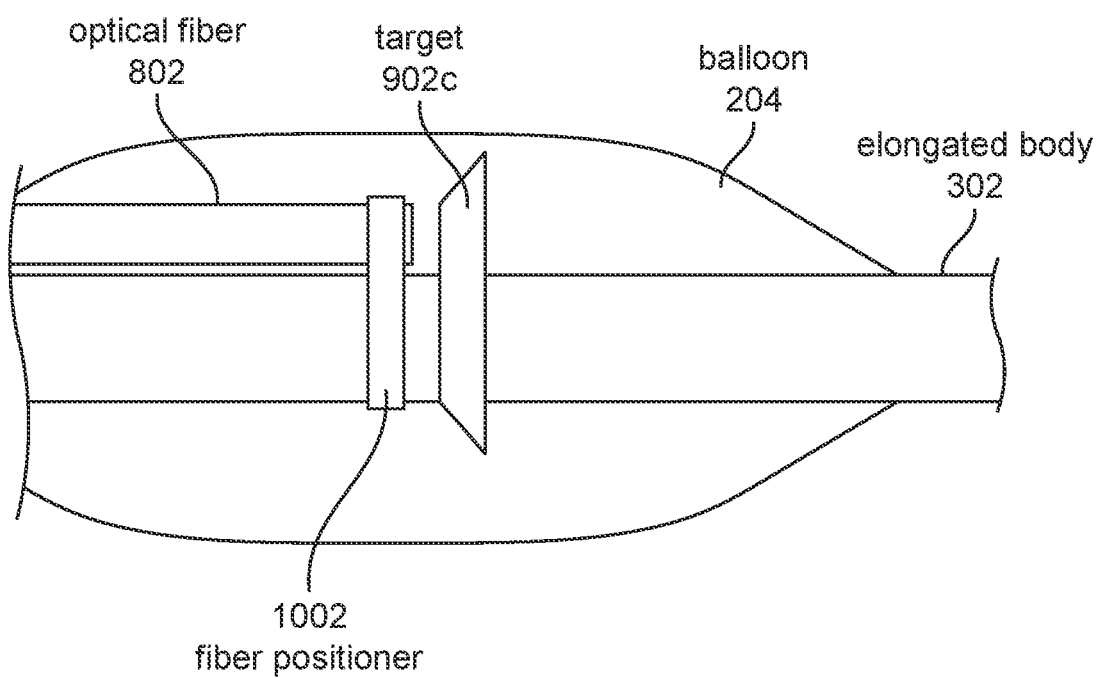

FIG. 10A illustrates a side view of a medical device 12 without a target. In this example, the wavelength of the energy from the laser is such that the saline/contrast-fluid mixture superheats from the laser itself, propagating the cavitation bubbles without necessitating an additional component in the form of the target. In FIGS. 10B-10D, various other wavelengths of laser energy may be used, as the saline/contrast-fluid mixture is not the intended recipient of said energy, and the target 902 is used to receive the laser energy and superheat, causing the surrounding saline/contrast fluid mixture to heat up in turn, and subsequently instigating the propagation of the cavitation bubbles.

FIG. 10B illustrates a side view of a target 902a as a trapezoid, with the flat side facing the distal fiber end 1402. FIG. 10C shows the side view of target 902b as an elongated octagon, wherein an angled or sloped surface may be in the path of the optical signal. FIG. 10D shows an example of a target 902c having a fiber-facing surface that is sloped or angled with respect to the angle of travel of the laser energy. This angled surface may permit the cavitation bubble 1404 to be emitted substantially perpendicular to this angle of travel of the laser energy and toward the calcified lesion.

In elongated bodies 302 of FIGS. 10A, 10B, 10C, and 10D, the optical fibers 802 are locked into place by a fiber positioner 1002. This fiber positioner 1002 may ensure that the relationship between the optical fiber 802 and the target 902 is consistent, both in the distance from one another and the distance the distal fiber end 1402 is from the central lumen 208.

According to some examples, the fiber may be repositioned within the balloon 204, and thus the distance to the target 902 may be modulated by the clinician. As described in other figures, this ability to reposition the optical fiber 802 is not dependent upon a target 902 being present in the elongated body 302. A sliding mechanism may be included on a handle or control interface coupled to the optical fibers 802, permitting axial movement and control of said optical fibers 802. Separate sliding mechanisms may be included should a clinician want to independently control each optical fiber 802 present in the elongated body 302. Should only a single optical fiber 802 be present in the elongated body 302, only a single sliding mechanism may be needed. Fiber positioners are shown and described in FIGS. 11A, 11B, 11C, and 11D.

Figure 11A:
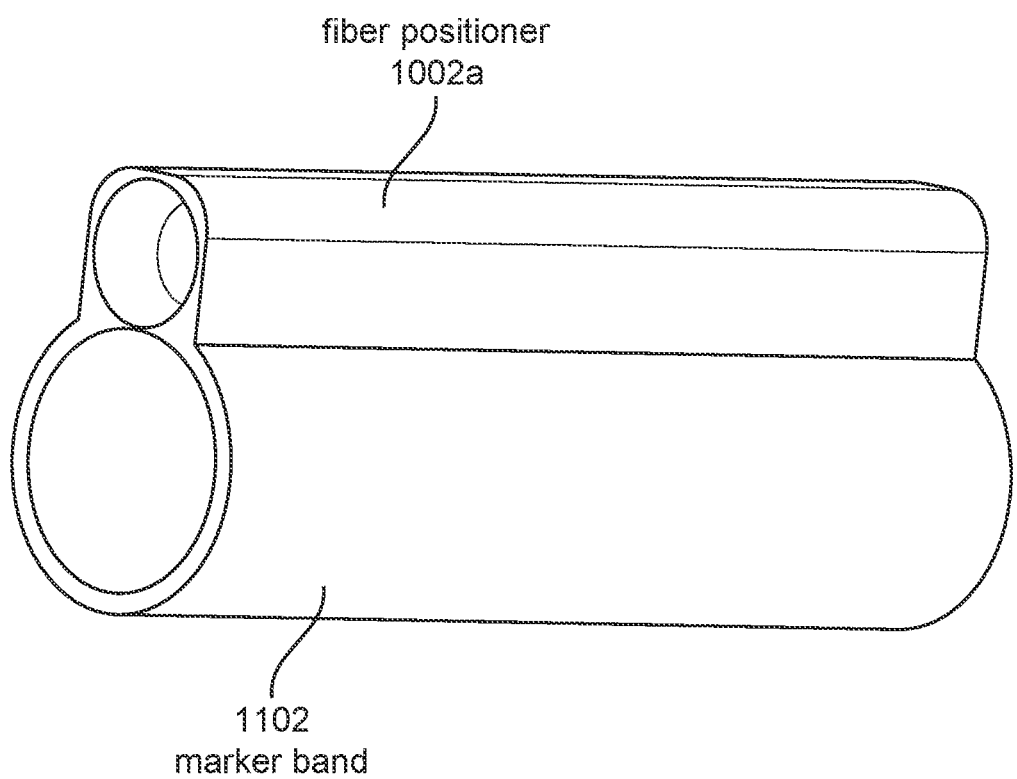
FIGS. 11A, 11B, 11C, and 11D illustrate profile views of three possible configurations of a fiber positioner for holding the optical fiber in place, as depicted in FIGS. 10A-10D.

FIGS. 11A, 11B, 11C, and 11D illustrate profile views of three possible configurations of a fiber positioner for holding the optical fiber in place, as depicted in FIGS. 10A-10D. Specifically, FIG. 11A illustrates a marker band 1102 with a top-component fiber positioner 1002a that holds onto the optical fiber 802 and has a chamfer at the end in which the tip of the optical fiber may sit but not make contact. Such a fiber positioner 1002 may be injection molded or extruded.

Figure 11B:
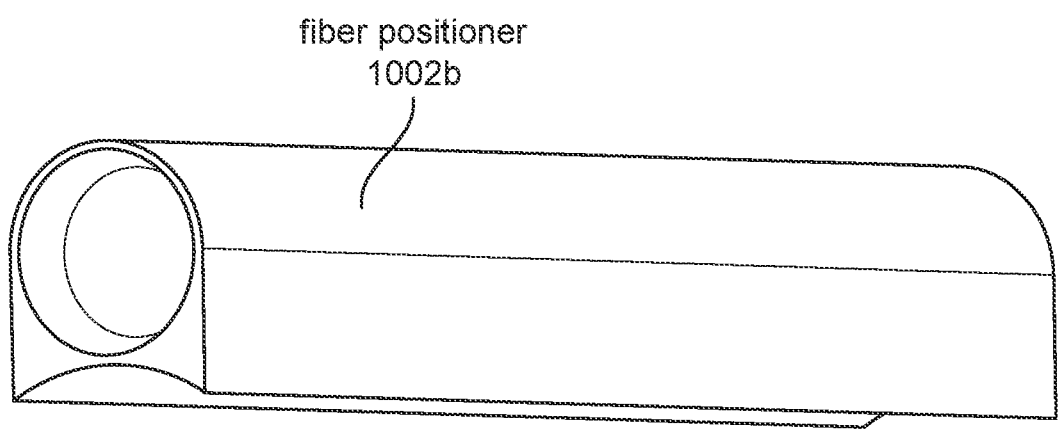

FIG. 11B illustrates the fiber positioner 1002 of FIG. 11A, but without the marker band 1102. This fiber positioner 1002b may also be extruded or injection molded, but because of the lack of marker band 1102, fiber positioner 1002b may be attached, such as with an adhesive, to a premade marker band 1102 or another component. The fiber positioner 1002b is radiused on the bottom to permit attachment to a circular mechanism, such as an elongated body 302, marker band 1102, or another component.

Figure 11C:
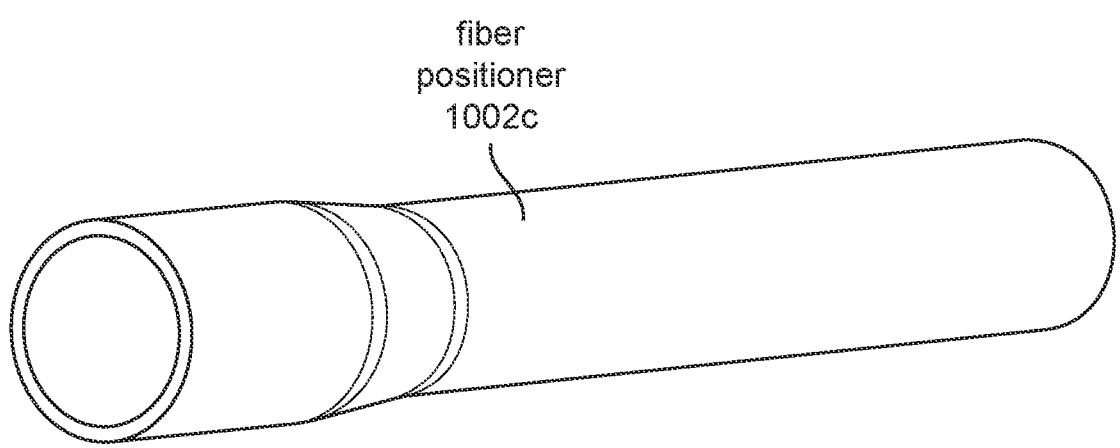

FIG. 11C illustrates another example of a fiber positioner 1002c. This fiber positioner 1002c is simpler in construction than those of FIGS. 11A and 11B, as it does not include multiple apertures or a radiused bottom portion. This fiber positioner 1002c may be held in place with respect to the elongated body 302 or may include laser-cut slits in its flared section to permit it to crimp down onto an elongated body 302, marker band 1102, or another component. Additional implementations include attaching the fiber positioner 1102c to the inner mechanism (i.e., elongated body 302, marker band 1102, etc.) via an ultraviolet (UV) adhesive, heat shrink, or a swagged marker band. It is understood that these attachment implementations may also be used with the fiber positioner 1002b of FIG. 11B. These attachment implementations are unnecessary in the fiber positioner 1002a of FIG. 11A, as the fiber positioner 1002a and the marker band 1102 are molded together in such an example.

Figure 11D:
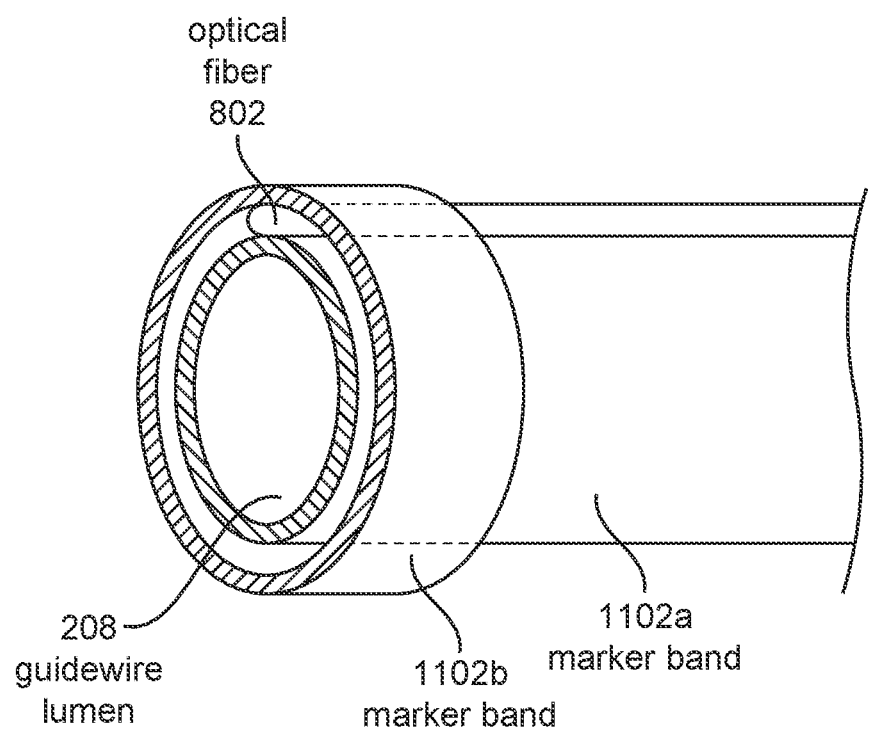

FIG. 11D illustrates another example of a fiber positioner 1002, shown as marker band 1102b. In this example, two marker bands 1102 are present—an inner marker band 1102a about the guidewire lumen 208, and an outer marker band 1102b which surrounds the inner marker band 1102a, as well as any present optical fibers 802. In this way, the inner marker band 1102a separates the optical fiber 802 a predetermined distance away from the guidewire lumen 208, and the outer marker band 1102b keeps the optical fibers 802 in place.

While not present in FIGS. 11A-11D, a flare, similar to the shroud as shown and described in FIG. 13 below, may be present in any of FIGS. 11A-11D. This flare may act as a safety feature, facilitating the prevention of any laser energy from contacting either the surface of the balloon or the guidewire lumen.

Figure 12:
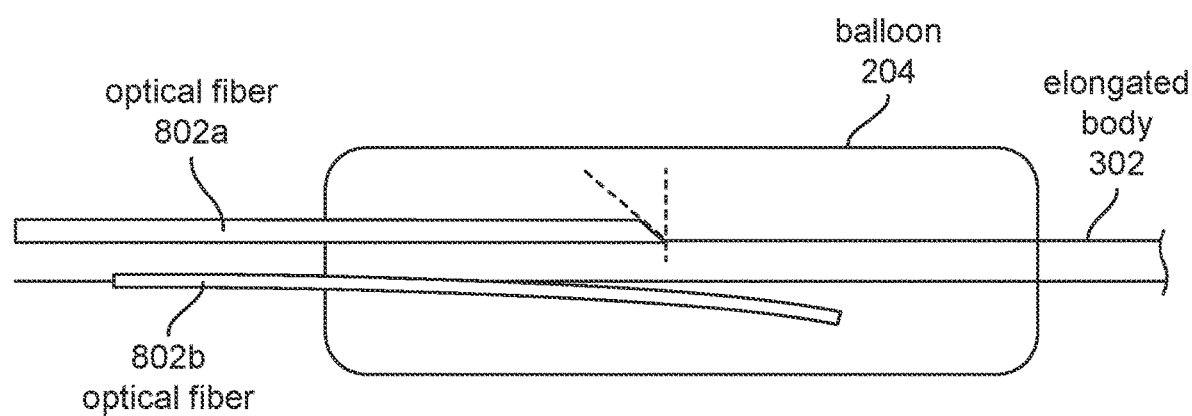
FIG. 12 illustrates a diagram of two optical fibers traversing an IVL catheter along a guidewire lumen and terminating inside an IVL balloon, according to some examples.

FIG. 12 illustrates a diagram of two optical fibers 802, represented as optical fiber 802a and optical fiber 802b, traversing an elongated body 302 along a guidewire lumen 208 and terminating inside of an IVL balloon 204, according to some examples. As seen in FIG. 12, the optical fiber 802a shown above the guidewire lumen 208 describes an angled distal tip end. According to some examples, this angled distal tip end is angled at greater than one hundred and fourteen degrees to the longitudinal axis of the guidewire lumen 208. Stated another way, if the distal fiber end 1402 travels substantially parallel to the vasculature through which it moves, the distal tip end may be angled at greater than twenty-four degrees to a plane perpendicular to the longitudinal axis of the lumen 208. This angled distal tip end may facilitate avoidance of the laser energy impinging upon the outer surface of the guidewire lumen 208. This may assist with the safety of the guidewire lumen 208, ensure that all of the laser energy is delivered into a target 902, or both.

As can be seen in the optical fiber 802b below the guidewire lumen 208, the optical fiber 802b may also terminate radially off-center from the guidewire lumen 208. Similar to the angled distal tip end, this radially off-center terminating optical fiber 802b may facilitate avoidance of the laser energy impinging upon the outer surface of the guidewire lumen 208. The distance at which the optical fiber 802b may be presented radially off-center from the guidewire lumen 208 depends upon the diameter of the optical fiber, as well as the location at which the optical fiber 802b is permitted to begin bending. Larger bends in the optical fiber 802b may necessitate larger balloons 204, which could be problematic for smaller diameter vasculature.

Figure 13:
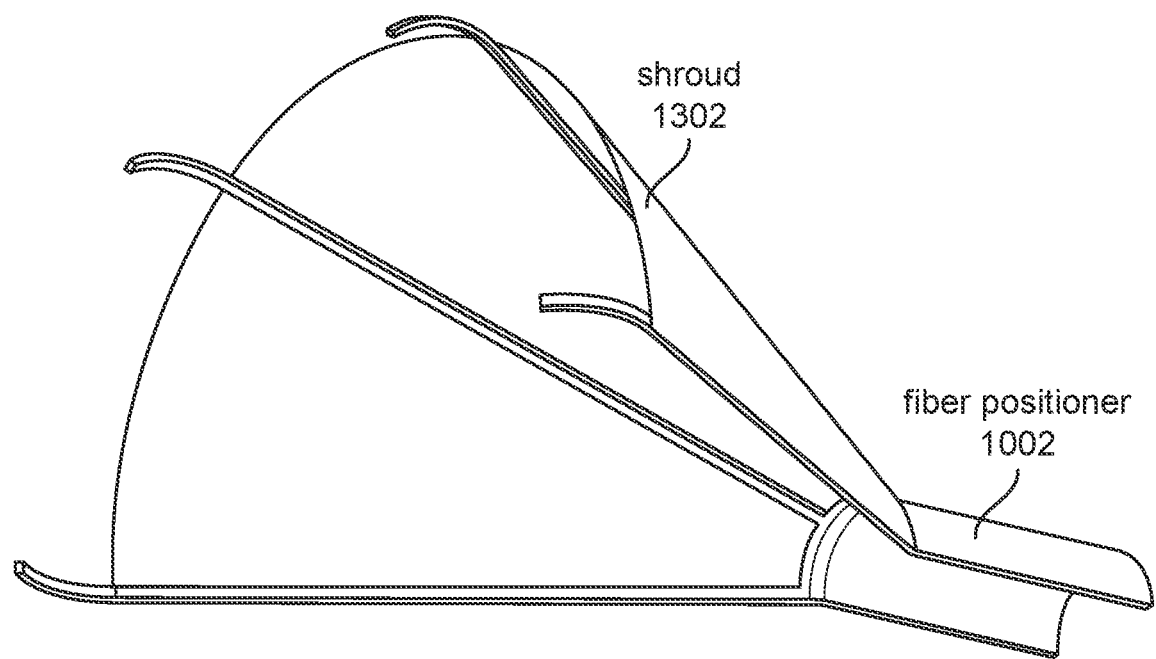
FIG. 13 illustrates a profile view of a shroud for protecting a balloon from an optical fiber.

FIG. 13 illustrates a profile view of a shroud 1302 for protecting a balloon 204 from an optical fiber 802. The shroud 1302 may be a laser-cut nitinol structure bonded to a skirt made of a material such as fabric, polymer, or anything else that is flexible. The skirt may expand when the balloon 204 is inflated. The nitinol structure may include tines with curved ends to provide smooth points of contact with the balloon 204 to prevent accidental perforation of said balloon 204. The skirt may also be expanded using a different mechanism within a handle proximal to the elongated body 302.

As used with the examples of FIGS. 11A, 11B, 11C, and 11D, the shroud 1302 may be used to protect the balloon 204 from the tip of the optical fiber 802, preventing accidental perforation of the balloon 204. The shroud 1302 may also be used with any of the fiber positioners 1002.

The solid portion of the shroud 1302 may be crimped or potted over the optical fiber 802, with the optical fiber 802 extending to a point just within the portion of the shroud 1302 where the skirt begins. This would permit the nitinol structure ("arms") and the skirt to collapse down about and past the tip of the optical fiber 802. While the shroud 1302 is presented as a 180-degree structure, it is understood that the shroud 1302 may present any amount of circumferential coverage between 0 degrees (no coverage) and 360 degrees (full circumferential coverage).

Figure 14A:
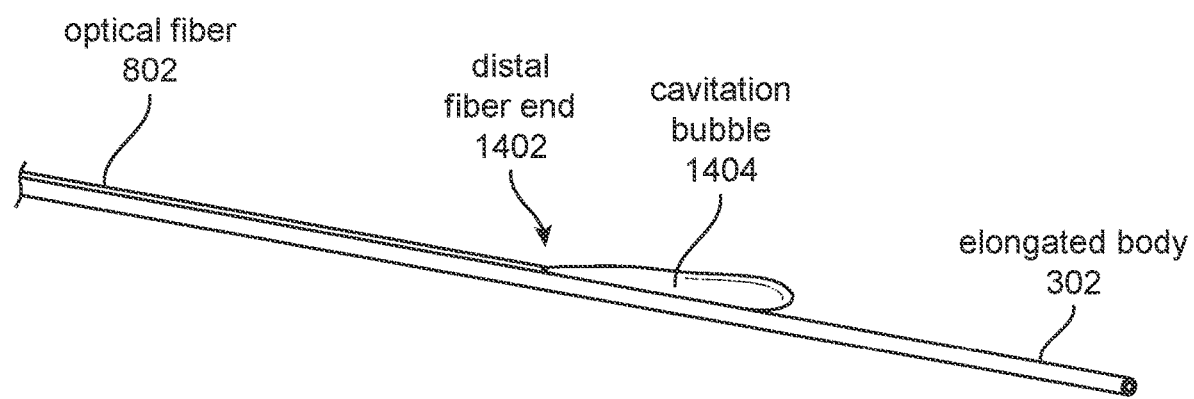
FIGS. 14A and 14B illustrate perspective views of a single optical fiber traveling along an IVL catheter and a cavitation bubble forming at the distal fiber end.
Figure 14B:
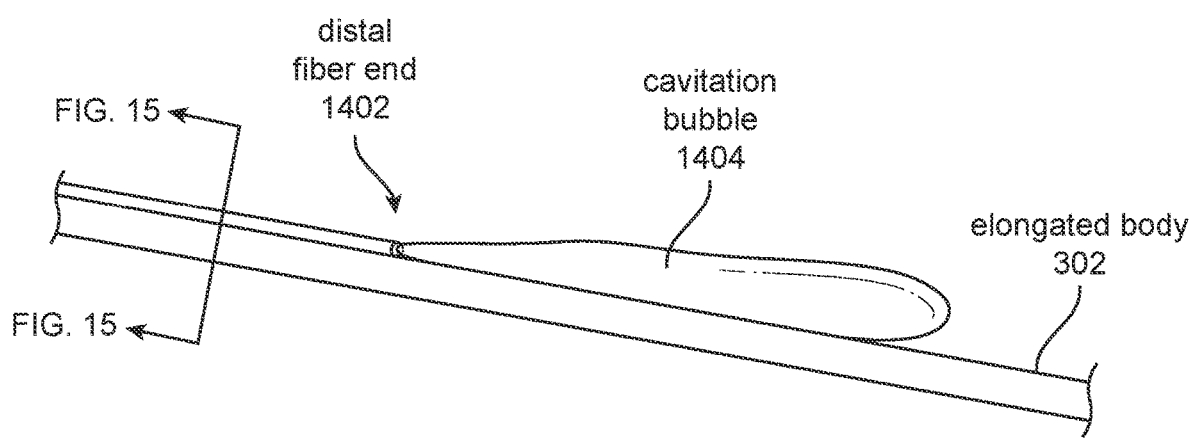

FIGS. 14A and 14B illustrate perspective views of a single optical fiber 802 traveling along an elongated body 302 and an elongated cavitation bubble 1404 being created at the distal fiber end 1402. Specifically, FIG. 14A illustrates the distal elongated body portion 306, while FIG. 14B illustrates a close-up view of the distal fiber end 1402 of the optical fiber.

While an elongated cavitation bubble 1404 is shown in FIGS. 14A and 14B, in some examples, a smaller cavitation bubble 1404 may be created. In either case, a single optical fiber 802 may travel the length of the elongated body 302 and terminate near the distal elongated body portion 306. In examples including an IVL balloon 204, the optical fiber 802 may terminate within the IVL balloon 204. If a small cavitation bubble 1404 is used, the distal fiber end 1402 may be located at least partially concentrically with the treatment site. Here, the cavitation bubble 1404 is formed through energy generation and subsequent directing of the energy along the optical fiber. This energy is dispelled from the distal fiber end 1402 and then interacts with the saline/contrast-fluid mixture to create the cavitation bubble. Once this cavitation bubble 1404 collapses, a shockwave is propelled radially away from the point of collapse, striking or penetrating the treatment site, and damaging any present calcification.

In the case of an elongated cavitation bubble, such as shown in FIGS. 14A and 14B, the process is very similar. The difference, however, is in the pulse width and frequency generated to produce a Moses effect. The Moses effect is a propagating cavitation bubble. The forming cavitation bubble 1404 enables subsequent laser energies to travel through the forming cavitation bubble to deposit the laser energy at the distal-most end of the cavitation bubble 1404, i.e., the end of the cavitation bubble 1404 furthest from the distal fiber end 1402. The cavitation bubble 1404 will continue propagating and collapsing through the length of the treatment site (the area of saline/contrast-fluid mixture, such as that of the portion of vasculature that has had the blood displaced or up to the length of the IVL balloon 204) permitting the treatment of a longer lesion than would a single cavitation bubble.

A target 902, such as that described in FIGS. 9B, 10B, 10C, and 10D, would likely not be used in conjunction with an elongated body 302 implementing the Moses effect, as this would significantly limit the distance the cavitation bubble 1404 may propagate. In some examples, a longer wavelength energy source may be utilized, such as Ho:YAG or CTH:Yag.

Figure 15:
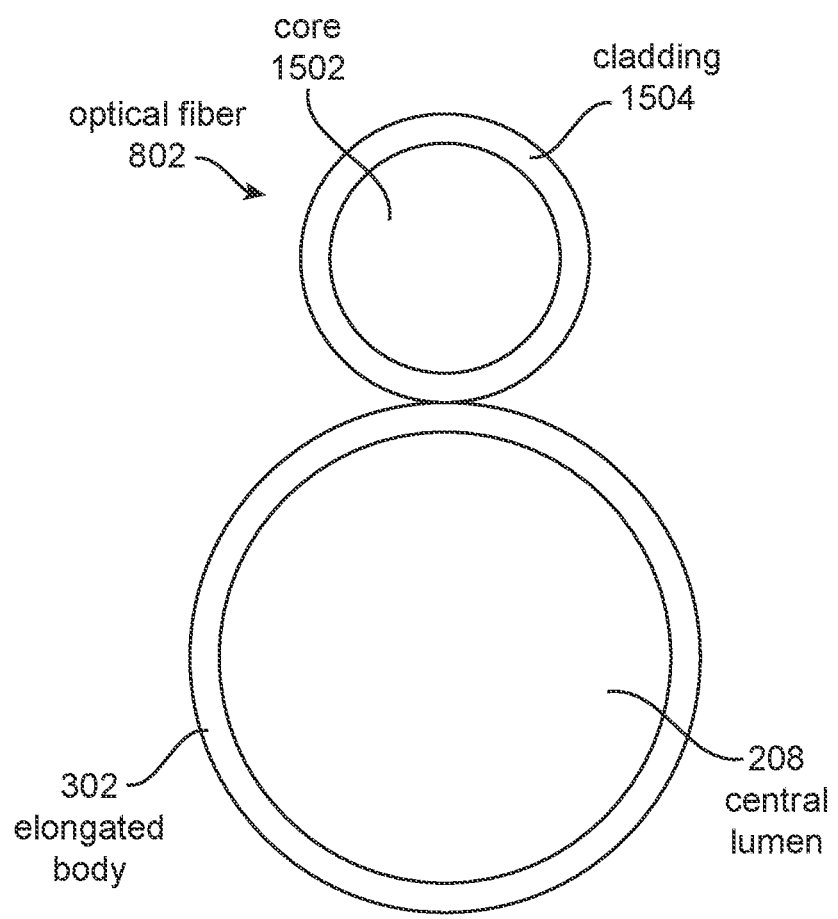
FIG. 15 illustrates a cross-sectional view of the elongated body and optical fiber of FIGS. 14A and 14B.

FIG. 15 illustrates a cross-sectional view of the elongated body 302 and optical fiber 802 of FIGS. 14A and 14B. As can be seen in FIG. 15, the optical fiber 802 includes a core 1502 and a cladding 1504. The cladding 1504 prevents laser energy from egressing the optical fiber 802 from the core 1502. Not present in FIG. 15, but shown and described in FIGS. 16A-18C is a score in the cladding 1504 to permit egress of laser energy from the optical fiber 802 premature to the distal fiber end 1402, as in some examples, such as the examples of FIGS. 14A, 14B, and 15, the system may not have this laser energy exit the optical fiber 802 prematurely. While not shown, according to some examples, the core may end up being scored a minor amount as well. Similar to FIGS. 7A and 7B above, the radii and proportions of each feature are exaggerated to simplify the expression of each independent structure in the drawing.

Figure 16A:
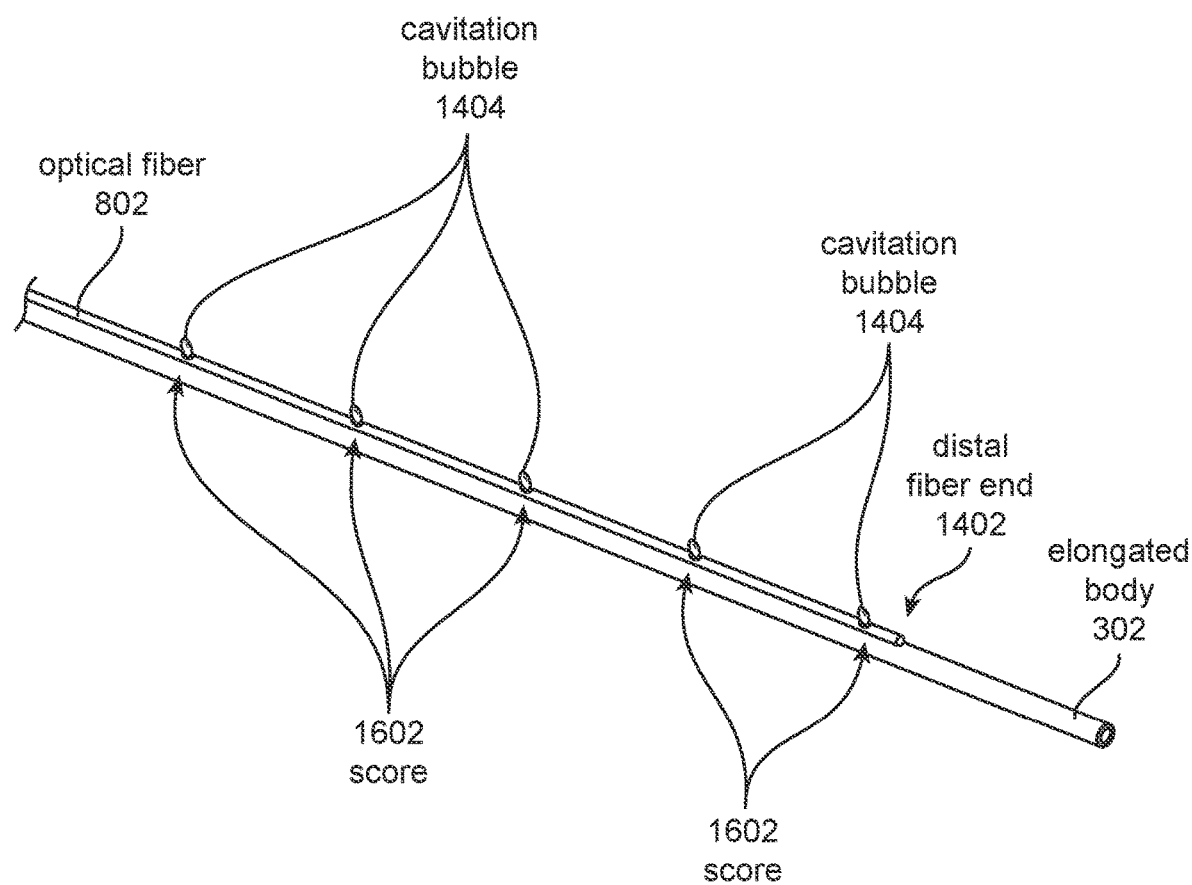
FIGS. 16A and 16B illustrate perspective views of a single optical fiber traveling along an IVL catheter with scores cut into the optical fiber.
Figure 16B:
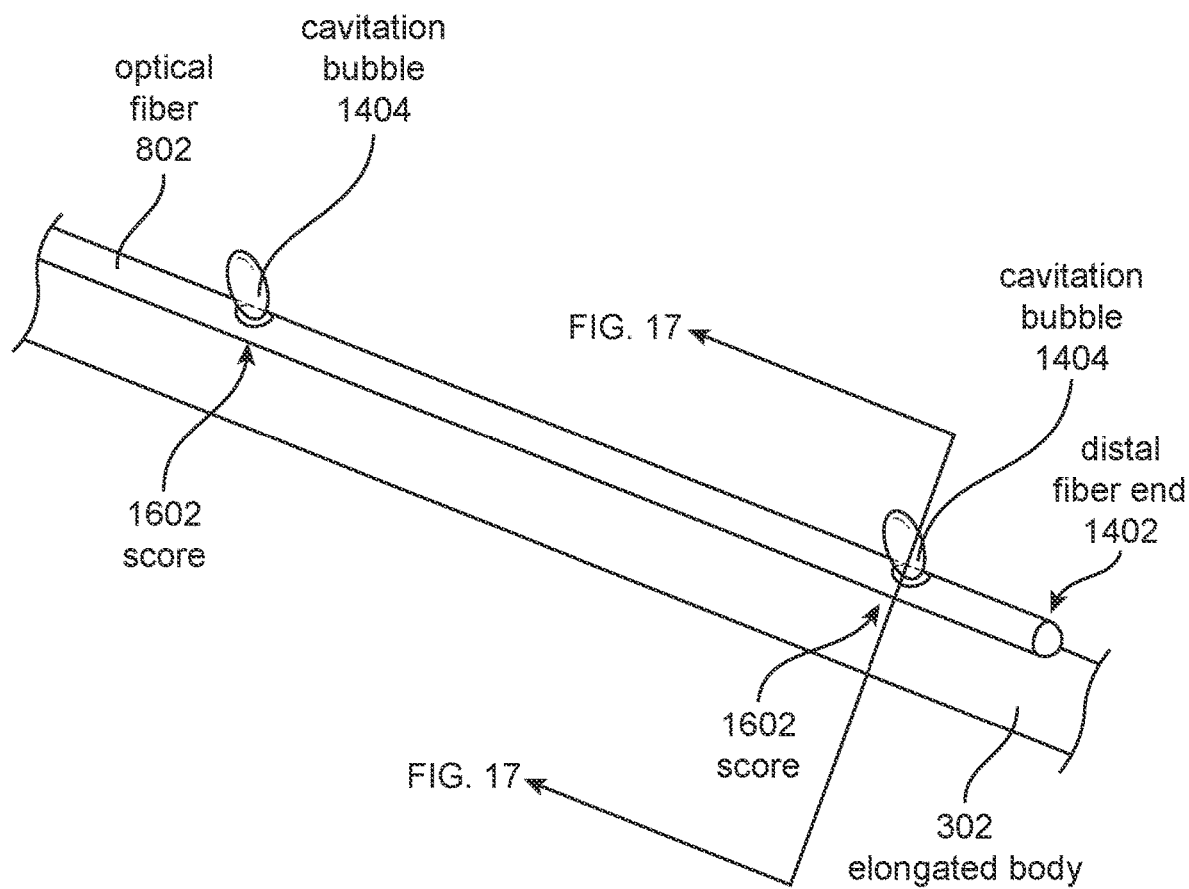

FIGS. 16A and 16B show perspective views of a single optical fiber 802 traveling along an elongated body 302 with scores 1602 cut into the optical fiber. Specifically, FIG. 16A illustrates the distal elongated body portion 306, while FIG. 16B illustrates a close-up view of two of the scores 1602 in the optical fiber 802. Both FIGS. 16A and 16B show cavitation bubbles 1404, initiating at the scores 1602 of the optical fiber 802.

As shown in FIGS. 16A and 16B, each score 1602 presents an exit point for the energy. This may effectively turn a single optical fiber 802 into a multiple-emitter laser fiber. In these examples, the energy is reflected within the optical fiber 802 until finding a natural termination point through which it may emit, such as each of the scores 1602. As shown in FIG. 16B, the energy may also be released through an opening at the distal fiber end 1402 in addition to the scores 1602.

Similar to the single optical fiber 802 examples of FIGS. 14A and 14B, once the energy is emitted from a score, it reacts with the saline/contrast-fluid mixture to create a cavitation bubble. This cavitation bubble 1404 will then collapse, causing a shock wave that impacts or penetrates the treatment area to cause damage to any present calcification. Similar to the above-described Moses effect, the presence of multiple scores 1602 permits multiple cavitation bubbles 1404 throughout the treatment area, thus extending the length of applicable treatment.

As shown in FIG. 16B, the distal fiber end 1402 may be used as an exit point, similar to the examples shown in FIGS. 14A and 14B. This distal fiber end 1402 may work the same way as the distal fiber end 1402 of the single optical fiber 802 in that a cavitation bubble 1404 may be formed here. Depending on the generator settings, such as pulse width and frequency, a Moses effect may be utilized at this distal fiber end 1402.

FIG. 16A shows five scores 1602 and FIG. 16B shows the distal-most two scores 1602. As few as one score, or a plurality of scores 1602 (e.g., as many scores 1602 as may fit within the IVL balloon 204, in examples including an IVL balloon 204) may be present.

Figure 17:
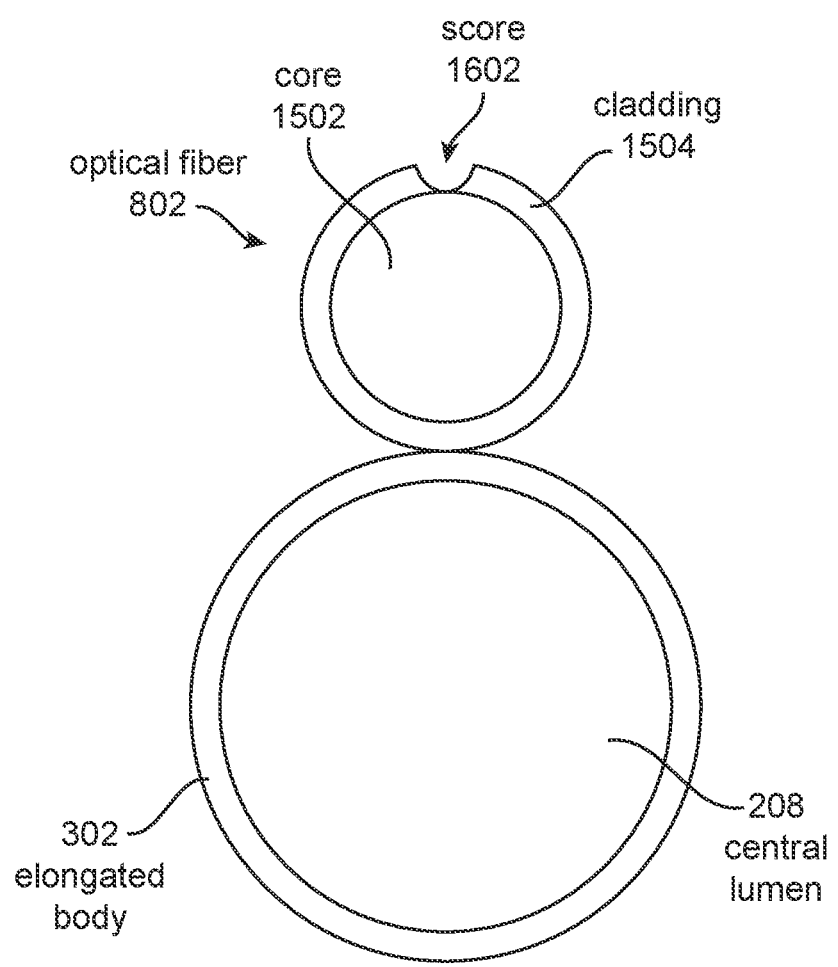
FIG. 17 illustrates a cross-sectional view of the elongated body and optical fiber of FIGS. 16A and 16B.

FIG. 17 illustrates a cross-sectional view of the elongated body and optical fiber of FIGS. 16A and 16B. Similar to FIG. 15, the optical fiber 802 includes a core 1502 and a cladding 1504. The cladding prevents laser energy from exiting the optical fiber 802 from the core 1502 in unwanted locations. Dissimilar to FIG. 15, the cladding 1504 is depicted as including a score 1602 in FIG. 17. The score 1602 as shown and described above in FIGS. 16A and 16B, and below in FIGS. 18A, 18B, and 18C, permits laser energy to exit the optical fiber 802 prior to the distal fiber end 1402. This premature emission can permit multiple cavitation bubbles 1404 to form along the body of the optical fiber 802, increasing the length of efficacious treatment along a calcified lesion 50 in a treatment area 40. Similar to FIGS. 7A, 7B, and 15 above, the radii and proportions of each feature are exaggerated to simplify the expression of each independent structure in the drawing.

Figure 18A:
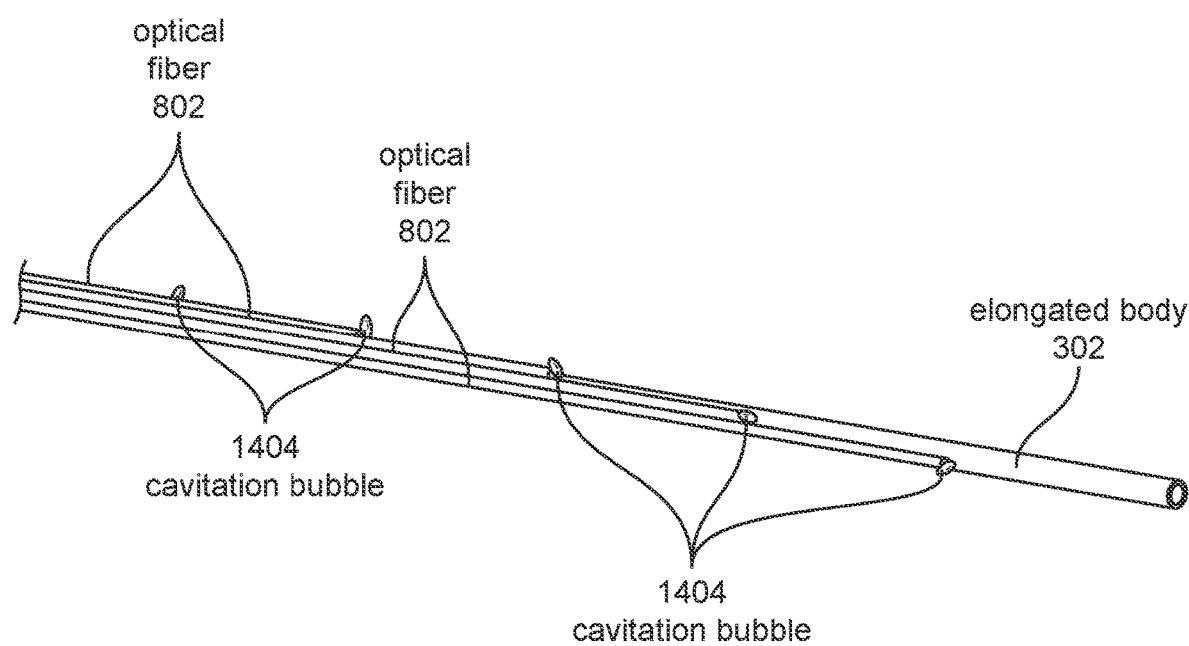
FIGS. 18A, 18B, and 18C illustrate various perspective views of a multiple optical fiber embodiment of the IVL catheter.
Figure 18B:
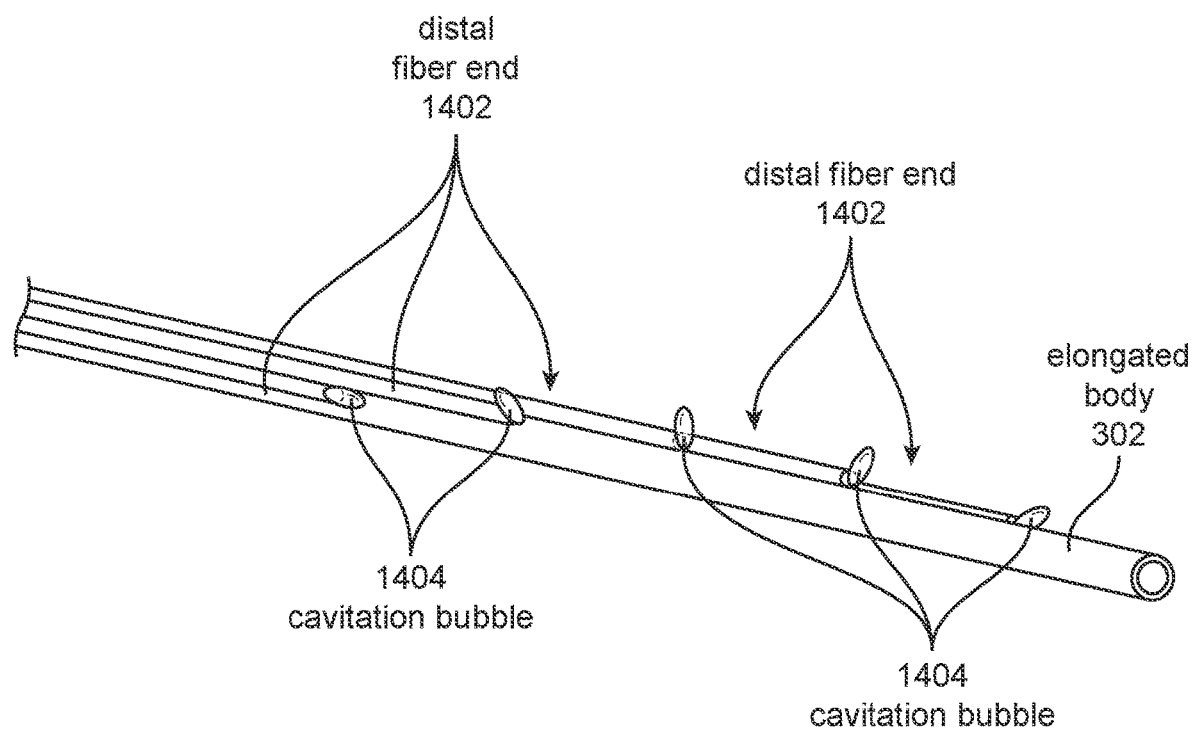
Figure 18C:
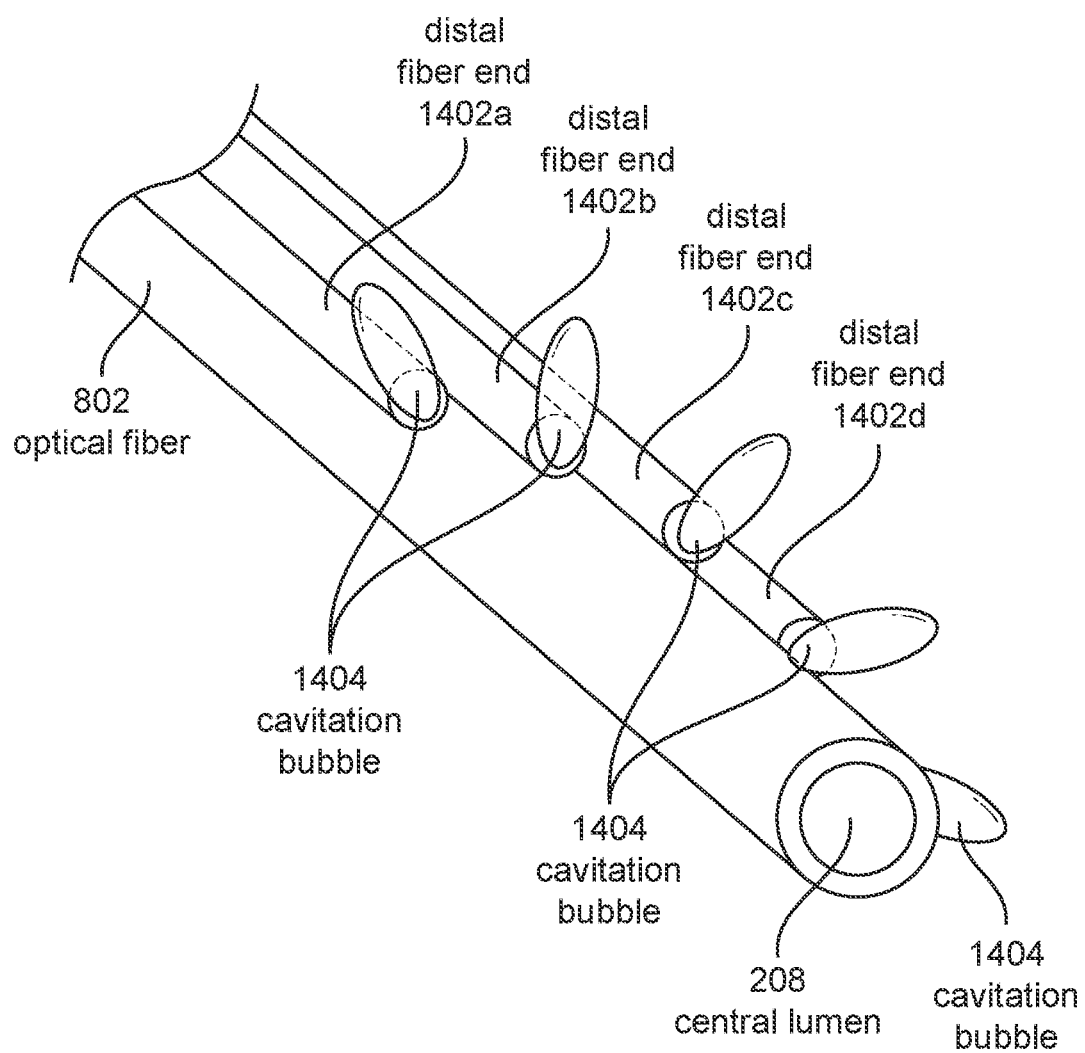

FIGS. 18A, 18B, and 18C illustrate various perspective views of a multiple optical fiber 802 embodiment of the elongated body 302. In each of FIGS. 18A-18C, the point of termination at the distal fiber end 1402 for each of the present optical fibers 802 depicts the initiation of a cavitation bubble.

According to the elongated body 302 of FIGS. 18A-18C, each optical fiber 802 acts similarly to the elongated body 302 of FIGS. 14A and 14B. Energy is transmitted from the generator 310 through each optical fiber. When the energy is emitted from each distal fiber end 1402a, 1402b, 1402c, and 1402d, it may interact with the saline/contrast-fluid mixture to create the cavitation bubbles 1404, as shown. Once the cavitation bubbles 1404 collapse, a shock wave is propelled substantially radially away from each point of collapse, striking and penetrating the treatment site and damaging any present calcification. Because there are multiple optical fibers 802, and the distal fiber ends 1402 are positioned a distance away from each other in the longitudinal direction, multiple cavitation bubbles 1404 may be formed along the length of the treatment area, thus extending the size of the lesion that can be treated.

By controlling the pulse width and frequency of the delivered energy, an operator could also achieve a Moses effect from each optical fiber 802. However, the benefits of accomplishing this with multiple laser emitters 206 may be less efficacious than with a single laser emitter, as the multiple laser emitters 206 already achieve the goal of lengthening the treatment area.

Depending on the energy source used, a target 902, or targets 902, may also be applied at the distal elongated body portion 306 to absorb the energy provided by the optical fibers 802. Similar to the example targets 902 of FIGS. 9B, 10B, 10C, and 10D, the target 902 may heat up due to absorbing this energy. As the target 902 continues to heat, a cavitation bubble 1404 may be formed on the target 902 as a result of the target heating up the surrounding saline/contrast solution. In this instance, the wavelength of the energy may not be intended to be absorbed directly by the saline/contrast-fluid mixture. All of the energy may be delivered into the target 902 to facilitate the creation of the superheated cavitation bubbles 1404 on the surface of the target 902 through absorption of this generated heat by the saline/contrast-fluid mixture.

While not shown in FIGS. 18A-18C, the optical fibers 802 may be locked into place by a fiber positioner 1002. This fiber positioner 1002 may ensure that the relationship between each distal fiber end 1402 and its related target 902 remains consistent, as well as the distance that each optical fiber 802 is offset from the central lumen 208.

Each of FIGS. 18A-18C show five optical fibers 802. As few as one optical fiber 802 (such as that shown in FIGS. 14A and 14B), or as many optical fibers 802 that may fit within the IVL balloon 204 (in examples including an IVL balloon 204), or as many optical fibers 802 as can fit within the vasculature being treated may be present.

The example elongated body 302 of FIGS. 18A-18C shows the optical fibers 802 surrounding the central lumen 208, with the distal fiber ends 1402 terminating at different points along the central lumen 208. For example, the optical fibers 802 may be spaced further from one another, or the optical fibers 802 may be provided as symmetrically dispositioned about the central lumen 208. Any configuration may be utilized.

While a cross-sectional view is not illustrated for FIGS. 18A-18C, it is understood that the cross-section may appear similar to the unscored cross-section of FIG. 15 or the cross-section with scores 1602 of FIG. 17. In either case, the only change is the number of optical fiber 802 surrounding the elongated body 302.

In all of the FIGS. 14A-18C, it is understood that the cavitation bubble 1404 formed, by any means disclosed herein, is considered to radiate outward from essentially the center of the elongated body 302, despite the short radius away each optical fiber 802 resides. The central lumen 208 does not interfere with the cavitation bubbles 1404 in any meaningful way. As such, each provided cavitation bubble 1404 is understood to radiate with complete, or approximately complete, 360-degree coverage about the vessel wall. In examples where the central lumen 208 does create some shadowing, the cavitation bubbles 1404 will still radiate with 360-degree coverage about the vessel wall, but some variance in the magnitude of strength of the bubble about this periphery may be observed.

FIGS. 19A-19H illustrate side views of various distal fiber ends 1402 for an optical fiber 802, as may be provided in an elongated body 302. In examples of distal fiber ends 1402 that are intended for collecting light or an optical signal (such as FIGS. 19A, 19C, 19D, 19E, and 19H), the shape of the fiber tip at the distal fiber end 1402 may improve the capabilities of the aforementioned fiber interrogation mechanism 524. By increasing the probability that light or the optical signal reflected back at the optical fiber 802 is captured by the distal fiber end 1402 through the use of these various fiber tips, it becomes more likely that a false negative of a problem with the fiber, such as a break is not reported. Thus the clinician will not prematurely remove the elongated body 302 due to faulty data reporting an issue with the optical fiber.

In examples of distal fiber ends 1402 that are intended for the emission of light or the laser energy in a certain direction (FIGS. 19B, 19C, 19D, 19F, and 19G), the shape of the fiber tip at the distal fiber end 1402 may facilitate directional discharge of the laser, redirection of the laser without the use of bending the optical fiber, or narrowing or broadening of the light beam or optical signal to affect the amount of energy delivered to a point.

Figure 19A:
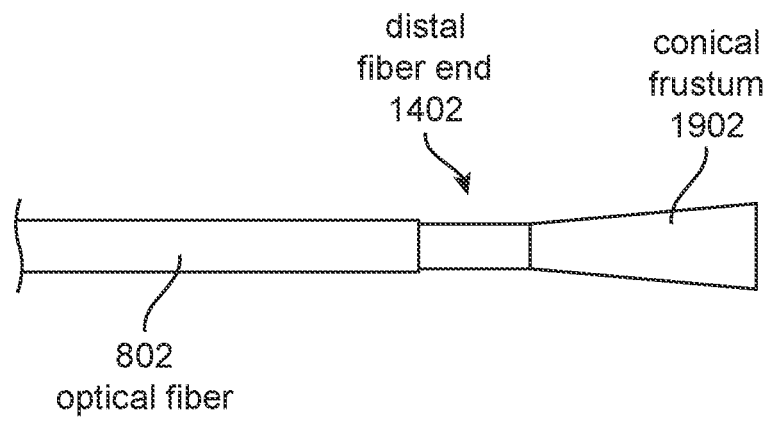
FIGS. 19A-19H illustrate side views of various distal fiber ends for an optical fiber, as may be provided in an IVL catheter.
Figure 19B:
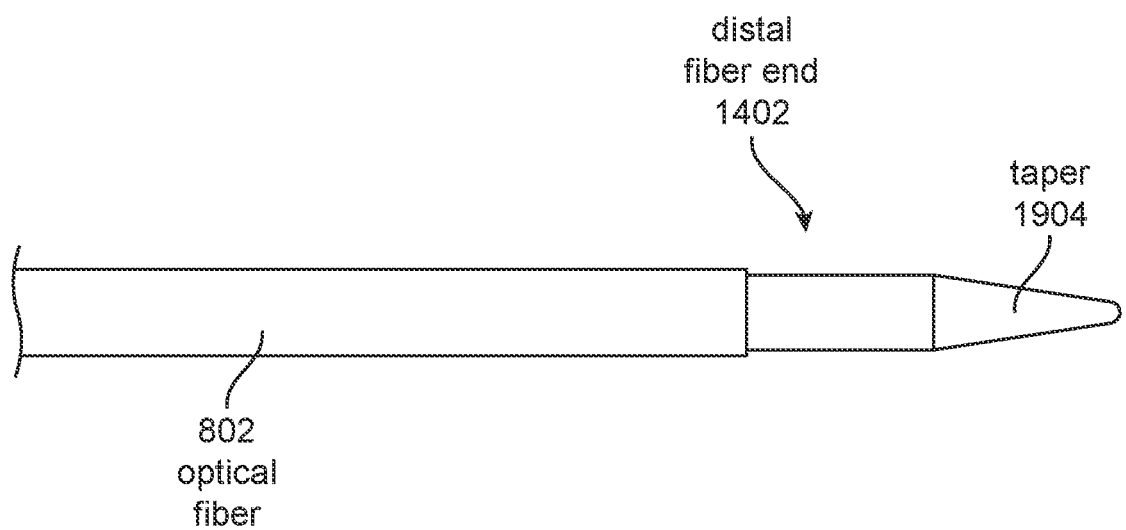
Figure 19C:
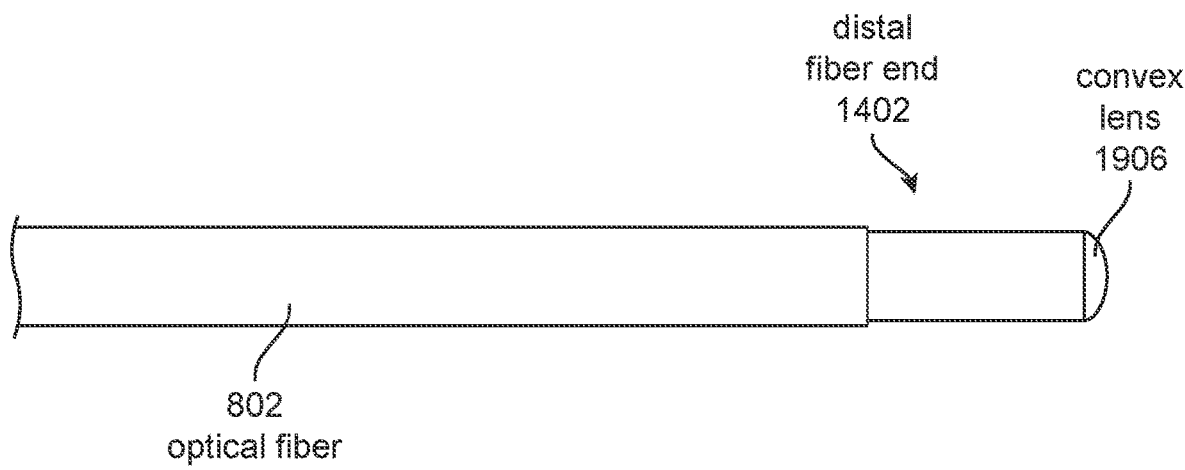
Figure 19D:
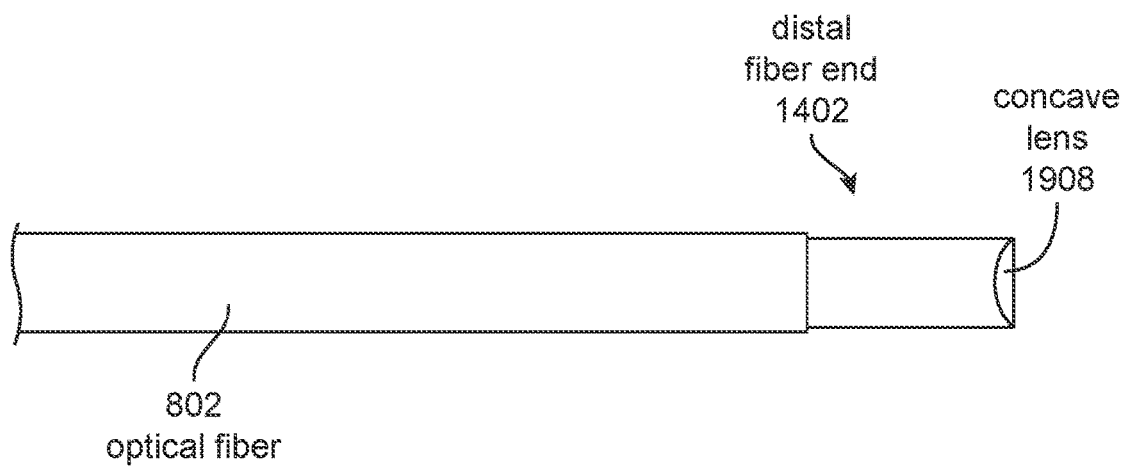

Of note, the examples illustrated in FIGS. 19C and 19D can facilitate the collection of light or an optical signal from a laser, as well as the emission of light or an optical signal from a laser. The fiber tips include functionality to improve both of these actions, and thus, depending on the user's needs, may assist in both a means of delivery of the laser and safety in the form of sensing the laser being reflected back.

FIG. 19A shows a distal fiber end 1402 including a conical frustum 1902 (an increase in the radial dimension), according to some examples. A conical frustum 1902 may increase the laser's spot size to decrease power density at the interface between the distal fiber end 1402 and the saline/contrast-fluid mixture or the target 902. FIG. 19B illustrates a distal fiber end 1402 having a taper 1904 (a decrease in radial dimension). A tapered 1904 profile may decrease the spot size of the laser and increase the laser's fluence or energy density.

FIG. 19C shows an optical fiber 802 with a distal fiber end 1402 including a convex lens 1906. A convex lens 1906 may increase light or optical signal collection from the laser while decreasing divergence. FIG. 19D illustrates a distal fiber end 1402 including a concave lens 1908, according to some examples. A concave lens 1908 may increase the laser's light or optical signal divergence.

Figure 19E:
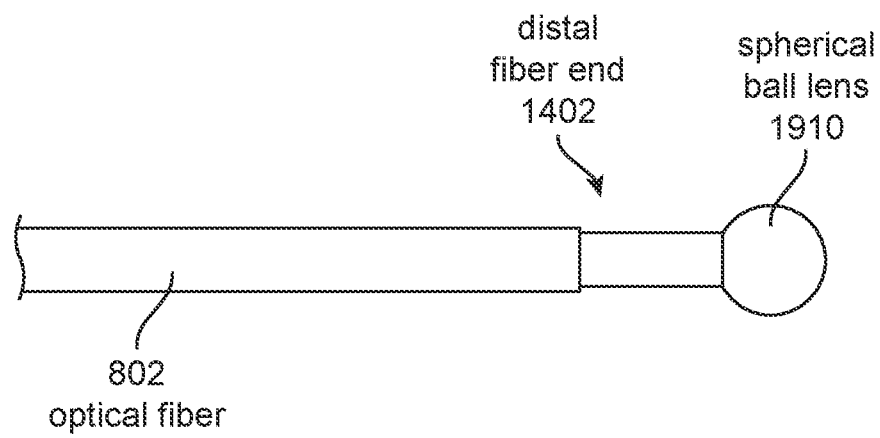
Figure 19F:
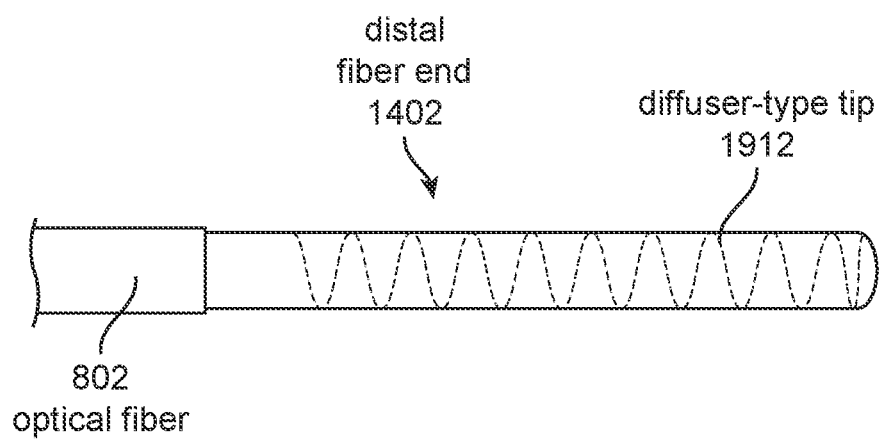

FIG. 19E illustrates an optical fiber 802 with a distal fiber end 1402 including a spherical ball lens 1910. A spherical ball lens 1910 may increase the angle of potential light collection by the optical fiber. FIG. 19F shows a distal fiber end 1402 including a diffuser-type tip 1912. The diffuser-type tip 1912 may permit full peripheral illumination through all sides of the distal fiber end 1402.

Figure 19G:
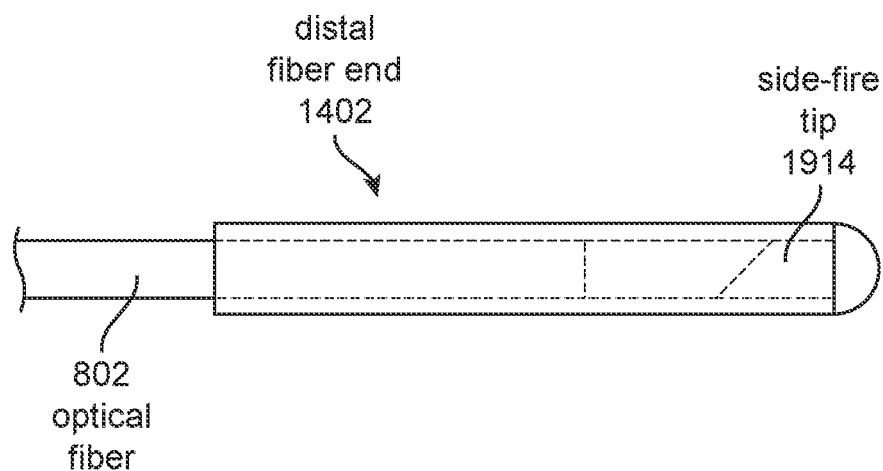
Figure 19H:
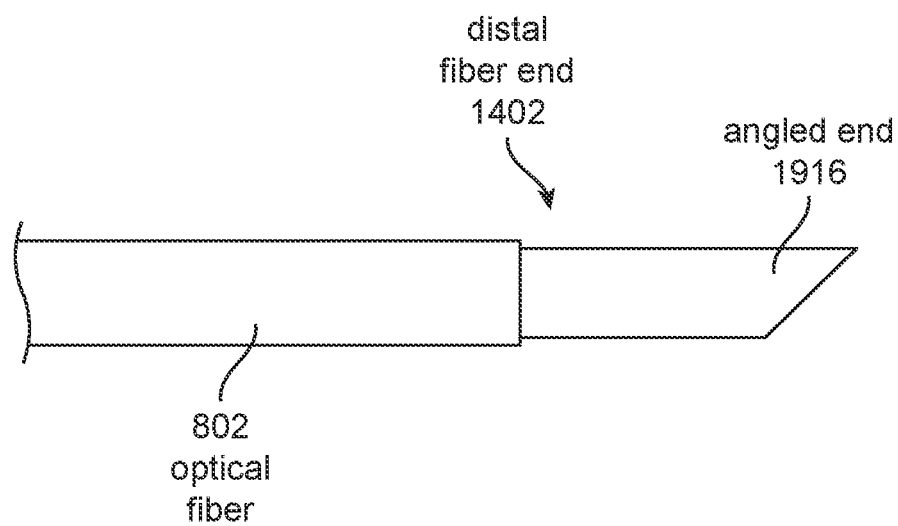

FIG. 19G shows an optical fiber 802 where the distal fiber end 1402 includes a side-fire tip 1914. The angle of the side-fire tip 1914 redirects the laser, at least partially, with respect to the elongated body 302 angle of traverse through the vasculature. This redirection may be any angle, including substantially perpendicular angles, as well as 180-degree redirection of the laser. FIG. 19H illustrates a distal fiber end 1402 including an angled end 1916. The angled end 1916 may reduce back reflection when collecting light or laser energy.

In any of FIGS. 19A-19H, where an IVL balloon 204 is present on the elongated body 302, the polished distal fiber end 1402 terminates within the IVL balloon 204. The polished distal fiber end 1402 may be cleaved, shaped, or flame-polished. In all examples, including a balloon 204, rough edges of the distal fiber end 1402 may be undesirable, as they can create wear and tear on the interior wall of the balloon 204, which may decrease the life expectancy of the balloon 204. It is understood, however, that it is not required to have the distal fiber end 1402 polished in any way without affecting the capabilities of the IVL system 10 as a whole.

Any energy source suitable for providing energy through an optical fiber 802 to produce a cavitation bubble, either through interaction with the saline/contrast-fluid mixture or a target 902, may be used in conjunction with any of the example IVL systems 10 and features depicted in FIGS. 1-19H. Some examples include the use of a lasing medium such as Nd:YAG (neodymium-doped:yttrium aluminum garnet), Ho:YAG (Holmium), or CTH:YAG (chromium, thulium, holmium). Lasing mediums such as Nd:YAG with a short wavelength (~3124 nanometers for Nd:YAG) may benefit from using the target 902 described in FIGS. 9B, 10B, 10C, and 10D. Lasing mediums such as CTH:YAG with a longer wavelength (~2.1 microns for CTH:YAG) may benefit from IVL systems 10, where the cavitation bubble 1404 is formed through interaction with the saline/contrast-fluid mixture. Additionally, different types of pumped lasers may be used with any of the example IVL systems 10 and features depicted in FIGS. 1-19H, such as discharge-pumped excimer lasers or flashlamp-pumped lasers.

Dimensions for the provided laser include wavelengths ranging from 308 nanometers to 2.1 microns (examples include 308 nanometer excimer lasers and 355 nanometer tripled Nd:YAG lasers), but any suitable wavelength may be used. Pulse widths may be "long" (about 300 to 600 microseconds) or short (less than 100 nanoseconds). The pulse repetition rate may be approximately 1-2 hertz (HZ), but any pulse repetition rate may be used. Optical fiber 802 diameters include 150 micrometers, 175 micrometers, and 200 micrometers. Again, any functional optical fiber 802 diameter may be used. The provided energy levels may be between 40 and 1500 milliJoules (mJ) and the like.

Figure 20:
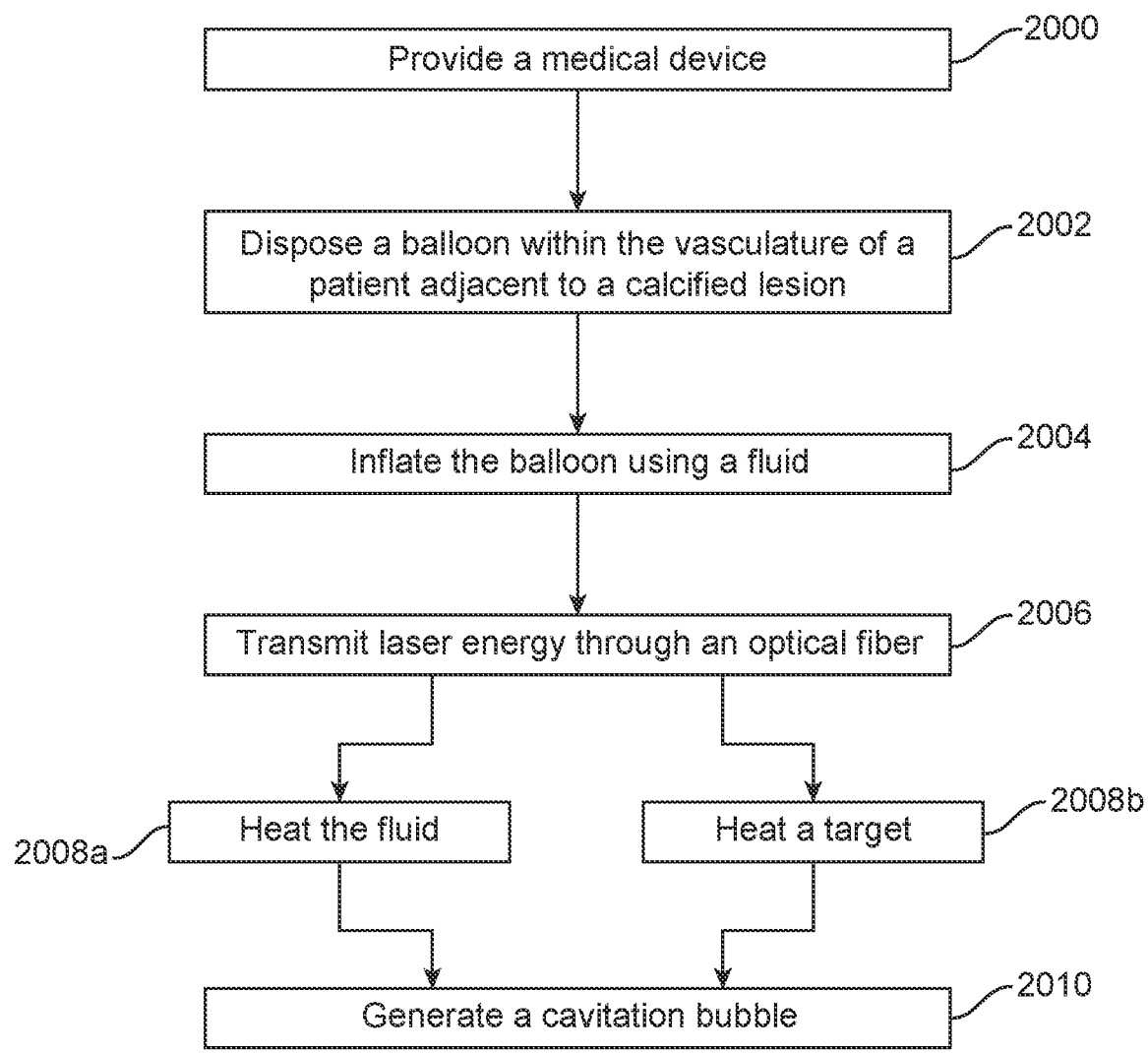
FIG. 20 illustrates a flowchart depicting a method of generating a cavitation bubble in a balloon catheter.

FIG. 20 illustrates a flowchart depicting a method of generating a cavitation bubble in a balloon catheter. In some examples, the method includes providing a medical device according to the description and the figures herein (at step 2000). The medical device may be a medical device as shown and described in FIGS. 1-19H, or any combination of these examples. According to some examples, the method includes disposing a balloon within a patient's vasculature adjacent to a calcified lesion (at step 2002). The balloon may surround, or partially surround, a distal end of a catheter.

The method may include inflating the balloon using a fluid (at step 2004). This inflation may serve multiple purposes. For example, inflating the balloon with the fluid may cause the balloon to make contact with a calcified lesion in the treatment area. Additionally, the fluid used to inflate the balloon may serve as a receptacle for incoming energy from a laser source, should one be provided. In this case, the fluid may be a saline/contrast-fluid mixture of any percentage composition. In some examples, the method includes transmitting laser energy through an optical fiber (at step 2006). This laser energy is delivered through a catheter and toward the distal end of said catheter. The laser energy is intended to heat a target, be it a physical target (as described in step 2008*b*) or the fluid within the balloon (as described in step 2008*a*).

According to some examples, the method includes heating the fluid (at step 2008*a*). The laser energy is absorbed by the fluid, such as a saline/contrast-fluid mixture, and subsequently, the absorbed energy heats up the fluid. The method may include generating a cavitation bubble (at step 2010). As a result of the fluid heating up, a cavitation bubble may form and subsequently collapse. This cavitation bubble may generate high-energy pressure waves, which can be utilized to disrupt calcified lesions in a treatment area.

Alternatively, in some examples, the method includes heating a target (at step 2008*b*). This physical target may act as a receptacle for the laser energy in this case. As the target heats up, it may impart its heat to the surrounding fluid, thus causing the surrounding fluid to heat up as well. According to some examples, the method includes generating a cavitation bubble (at step 2010). In a similar manner as expressed above, as a result of the fluid heating up, a cavitation bubble may form and subsequently collapse. To reiterate—this cavitation bubble may then generate high-energy pressure waves, which can be used to disrupt calcified lesions in a treatment area.

Figure 21:
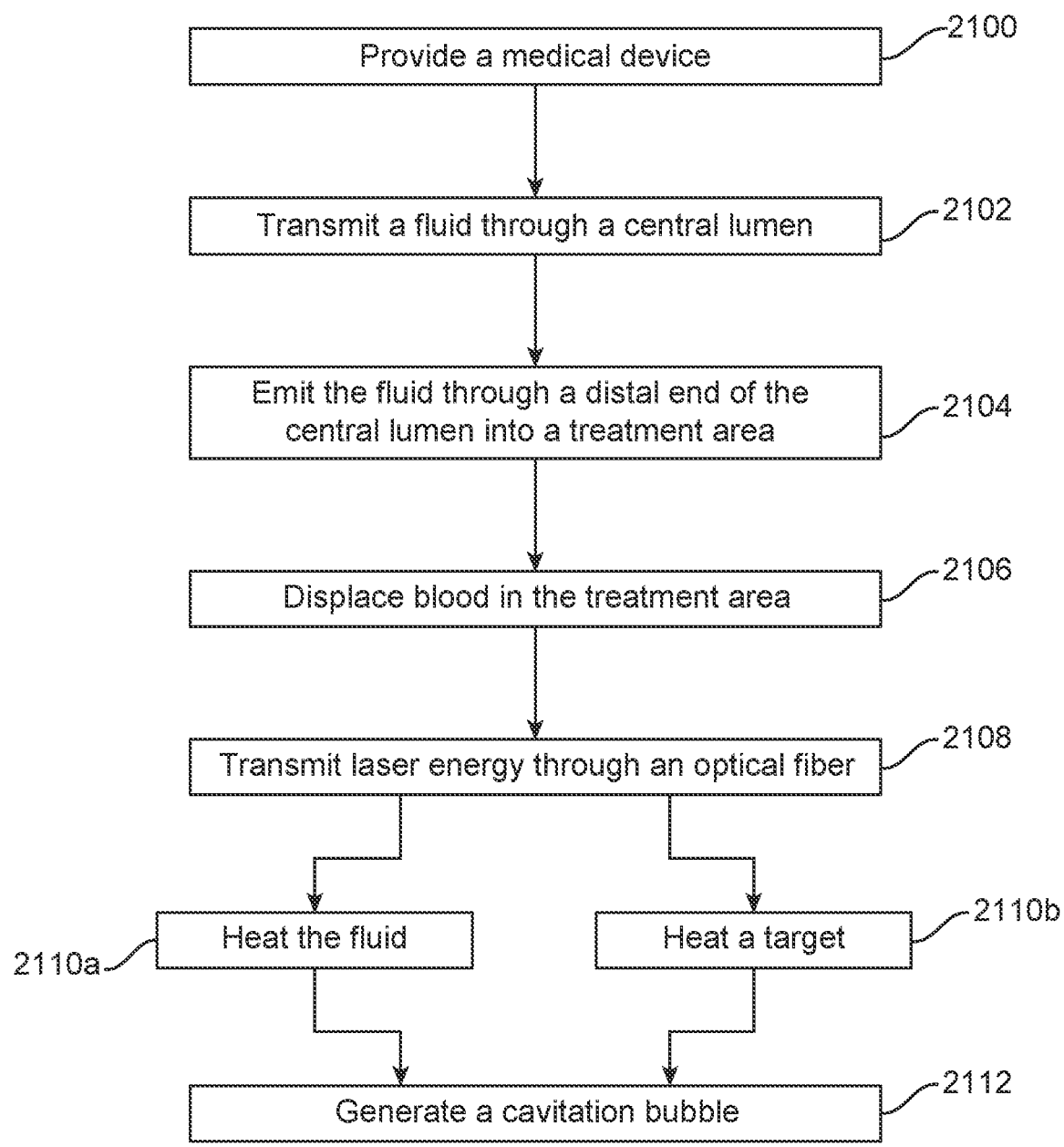
FIG. 21 illustrates a flowchart depicting a method of generating a cavitation bubble within a vessel.

FIG. 21 illustrates a flowchart depicting a method of generating a cavitation bubble within a vessel. In some examples, the method includes providing a medical device according to the description and the figures herein (at step 2100). Again, the medical device may be a medical device as shown and described in FIGS. 1-19H, or any combination of these examples. According to some examples, the method includes transmitting a fluid through a central lumen (at step 2102). The provided fluid may be used to inflate a balloon, if present, as described in FIG. 20. The provided fluid may also be used as a receptacle for incoming energy from a laser source, should one be provided. In this case, the fluid may be a saline/contrast-fluid mixture of any percentage composition.

The method may include emitting the fluid through a distal elongated body portion of the central lumen into a treatment area (at step 2104). In this case, a balloon is not present, and the fluid is instead injected directly into the vasculature of a patient. In some examples, the method includes displacing blood in the treatment area (at step 2106). This blood displacement may facilitate better contact between the fluid and the walls of the treatment area, allowing the pressure waves emitted from the collapsing cavitation bubbles to better disrupt any present calcified lesions. By removing the blood from the treatment area, the fluid may fill the entirety, or a substantial portion of, the treatment area.

According to some examples, the method includes transmitting laser energy through an optical fiber (at step 2108). This laser energy may be delivered through a catheter and toward the distal end of said catheter. In some examples, the laser energy is intended to heat a target, be it a physical target (as described in step 2108*b*) or the fluid within the balloon (as described in step 2108*a*).

The method may include heating the fluid (at step 2110*a*). The laser energy may be absorbed by the fluid, such as a saline/contrast-fluid mixture, and subsequently, the absorbed energy heats up the fluid. In some examples, the method includes generating a cavitation bubble (at step 2112). As a result of the fluid heating up, a cavitation bubble may form and subsequently collapse. This cavitation bubble may generate high-energy pressure waves, which can be utilized to disrupt calcified lesions in a treatment area.

Alternatively, according to some examples, the method includes heating a target (at step 2110*b*). This physical target may act as a receptacle for the laser energy in this case. As the target heats up, it may impart its heat to the surrounding fluid, thus causing the surrounding fluid to heat up as well. The method may include generating a cavitation bubble (at step 2112). In a similar manner as expressed above, as a result of the fluid heating up, a cavitation bubble may form and subsequently collapse. To reiterate—this cavitation bubble may then generate high-energy pressure waves, which can be used to disrupt calcified lesions in a treatment area.

Included in the present disclosure is a medical device 12 including an elongated body 302 having a distal elongated body portion 306 and a central longitudinal axis 308. According to some examples, the medical device 12 includes a balloon 204 positioned along the distal elongated body portion 306, the balloon 12 having an interior balloon surface 702 and an exterior balloon surface 704 and configured to receive a fluid 212 to inflate the balloon 204 such that the exterior balloon surface 704 contacts a calcified lesion 50 within a vasculature of a patient 20. The medical device 12 may include one or more pressure wave emitters 206 positioned along the central longitudinal axis 308 of the elongated body 302 within the balloon 204, the one or more pressure wave emitters 206 configured to propagate at least one pressure wave through the fluid 212 to fragment the calcified lesion 50. In some examples, at least one of the pressure wave emitters 206 includes an optical fiber 802 configured to transmit laser energy into the balloon 204. According to some examples, the laser energy is configured to create a cavitation bubble 1404 in the fluid 212 upon contact with the fluid 212 to generate the at least one pressure wave.

The optical fiber 802 may terminate near the distal elongated body portion 306. In some examples, the medical device 12 further includes a laser energy generator 310, wherein the laser energy generator 310 is configured to selectively pulse the laser energy. According to some examples, the pulsed laser energy is configured to generate a Moses Effect.

The medical device 12 may further include a plurality of optical fibers 802, each optical fiber 802 configured to transmit laser energy and terminating at a distal fiber end 1402 at a different distance along the distal elongated body portion 306. In some examples, the laser energy is emitted from the distal fiber ends 1402.

According to some examples, the optical fiber 802 includes a core and a cladding. In some examples, the cladding is disposed around the core, and the laser energy is emitted from the core through scores placed in the cladding. The medical device 12 may further include multiple optical fibers 802 disposed around the distal elongated body portion 306.

In some examples, the laser energy is configured to have a wavelength of between about 1900 nanometers (nm) and 2100 nm. According to some examples, the wavelength is about 2000 nm. Isotopes of the doping elements may cause some small spread in the wavelength, and doping concentrations in the crystal may slightly shift the wavelengths as well. Because of this, "about" as used herein in conjunction with "wavelength" is intended to mean plus or minus 30 nm. In some examples, the wavelength is between 1970 nm and 2030 nm. In examples where a CTH:YAG laser is used, the wavelength may be selected from the group consisting of 1970 nm, 2030 nm, 2080 nm, 2091 nm, 2097 nm, and 2121 nm. In examples where a Ho:YAG laser is used, the wavelength may be about 2100 nm.

In some examples, the laser energy is configured to have an energy between about 40 mJ and about 1500 mJ. According to some examples, the laser energy has a pulse width between about 10 nanoseconds and about 600 microseconds. The laser energy may have a pulse repetition rate between about 1 Hz and about 2 Hz.

In some examples, the medical device 12 further includes an Nd-YAG laser configured to provide the laser energy. According to some examples, the medical device 12 further includes a Holmium laser selected from the group consisting of Ho:YAG and CTH:YAG, the Holmium laser configured to provide the laser energy. The medical device 12 may further include an excimer laser configured to provide the laser energy.

In some examples, the medical device 12 further includes a pressure sensor 522 configured to detect ruptures in the balloon 204, wherein the pressure sensor 522 is configured to halt the laser energy upon detection of a balloon rupture. This detection may also occur due to any loss of pressure of a certain threshold. According to some examples, the medical device 12 further includes a fiber interrogation mechanism 524 configured to detect breakage of the optical fiber 802.

The medical device 12 may further include a target 902 disposed distally of the optical fiber 802. In some examples, at least one of the pressure wave emitters 206 includes an optical fiber 802 configured to transmit laser energy into the balloon 204 and impact the target 902. According to some examples, the target 902 is configured to heat up upon being impacted by the laser energy, and the heat from the target 902 is configured to heat a fluid 212 causing emission of the pressure wave. The medical device 12 may further include the optical fiber 802 having a distal fiber end 1402 and a fiber positioner 1002 to maintain a constant distance between the distal fiber end 1402 and the target 902 such that the laser energy transmitted into the balloon 204 will impact the target 902.

In some examples, the medical device 12 defines a central lumen 208 extending through the elongated body 302, the central lumen 208 having a proximal lumen end and a distal lumen end opposite the proximal lumen end. In some examples, the central lumen 208 is configured to transmit fluid 212 to displace blood in a treatment area 40 adjacent a calcified lesion 50 within a vasculature of a patient 20.

According to some examples, a balloon surface selected from the group consisting of the interior balloon surface 702, the exterior balloon surface 704, and combinations thereof further includes a metalized coating 706 configured to increase a damage threshold of the balloon 204.

Figure 22:
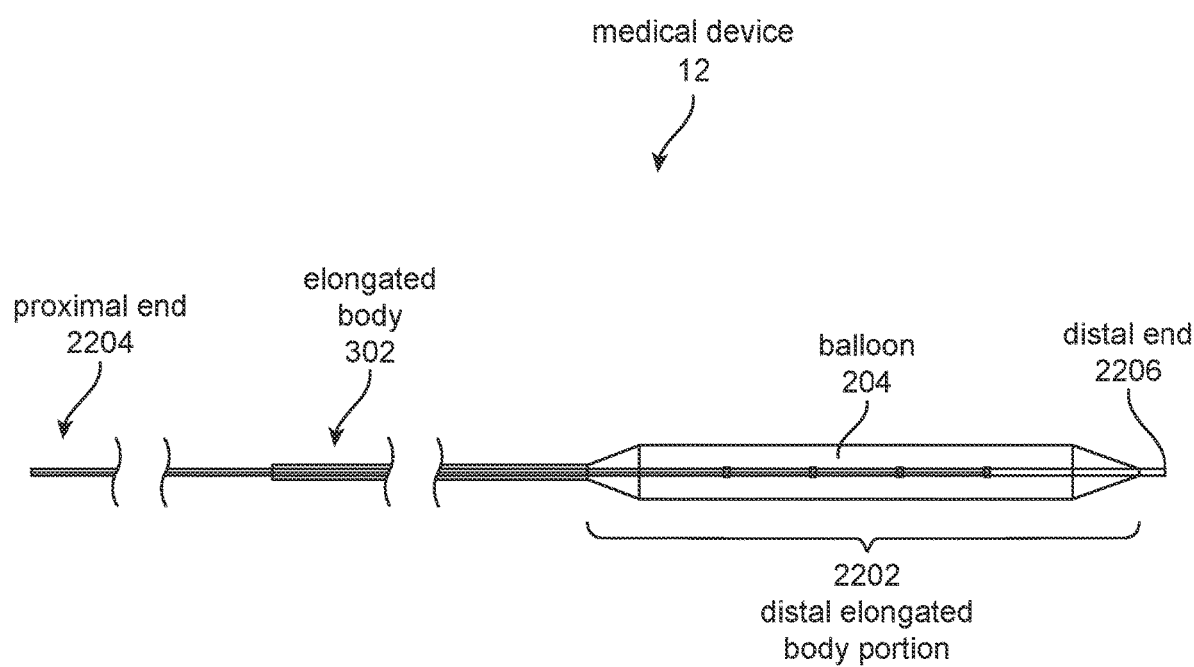
FIG. 22 illustrates another side view of an example IVL system.

FIG. 22 illustrates another side view of an example IVL system including a medical device 12. As shown, the medical device 12 extends from a proximal end 2204 to a distal end 2206. An elongated body 302, such as a catheter, may be implemented in the medical device 12 and extend the length of the medical device 12. A portion of the elongated body 302 near the distal end 2206 is referred to here as the distal elongated body portion 2202. The distal elongated body portion 2202 may extend from where the elongated body 302 enters the balloon 204 all the way to the distal end 2206, as seen in FIG. 22. In some examples, the distal elongated body portion 2202 may extend proximal to the balloon 204, or terminate at the same location as the point at which the balloon 204 comes back into contact with the elongated body 302 at its distal end.

In any case, the distal elongated body portion 2202 may be of a different cross-sectional size than the rest of the elongated body 302. This may provide benefits such as decreasing the crossing profile of the medical device 12 due to additional components along this distal elongated body portion 2202, such as the balloon 204 or fiber positioners as have been, and will be further shown and described in this disclosure. Additionally, the distal elongated body portion 2202 may have a different cross-sectional shape than the rest of the elongated body 302.

One of the problems seen in the prior art is how to manipulate the optical fiber such that it moves longitudinally. It is desirable to move the optical fiber with respect to the catheter, because once a balloon has been filled, it is more difficult to move the entire device. Especially in instances where the balloon is intended to make contact with a vessel, or, in this case, a calcified lesion in the vessel, the balloon may need to be deflated, or partially deflated, in order to reposition the entire device. Thus, moving the optical fiber within the balloon would remedy this problem. While devices are known to be capable of moving the optical fiber longitudinally, one of the problems left unresolved in the prior art is how to effectuate this longitudinal movement, which the present disclosure seeks to solve.

Figure 23A:
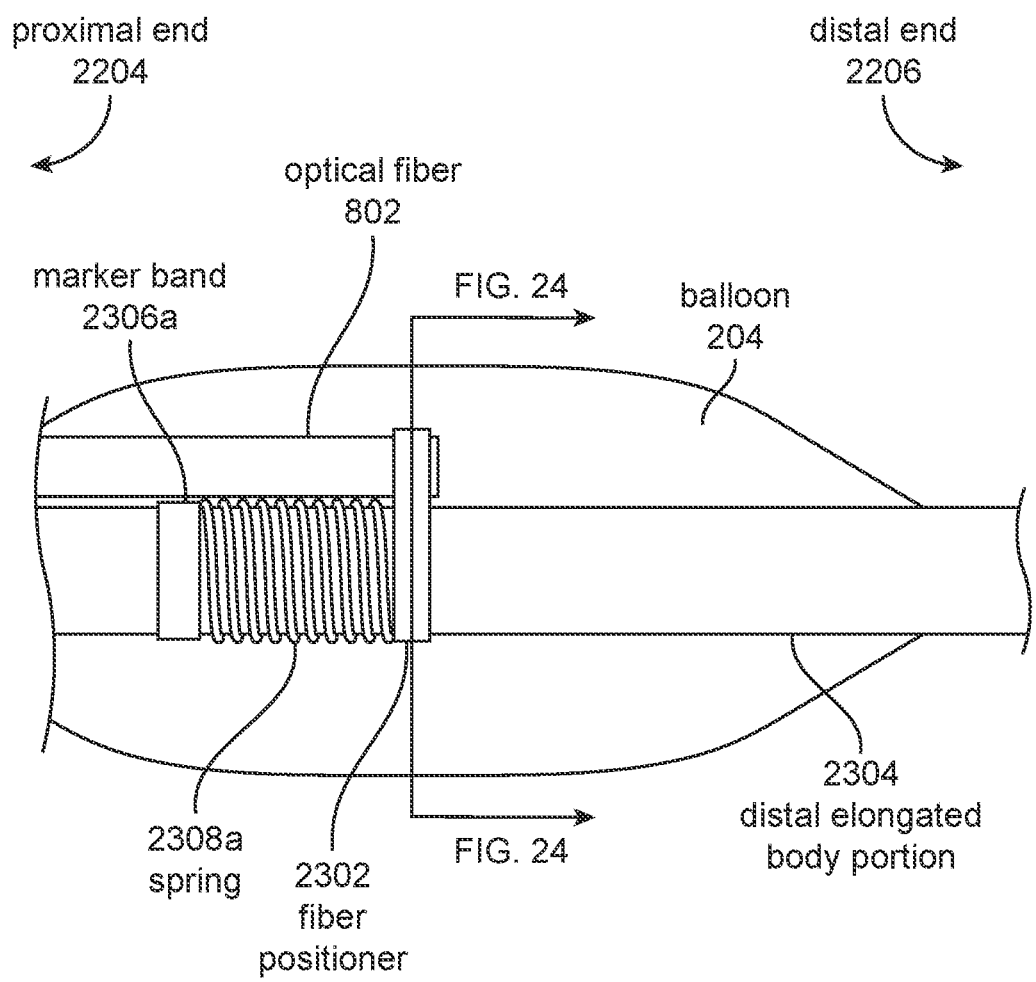
FIGS. 23A, 23B, and 23C illustrate diagrams of an IVL device including a movable fiber positioner, according to some examples.
Figure 23B:
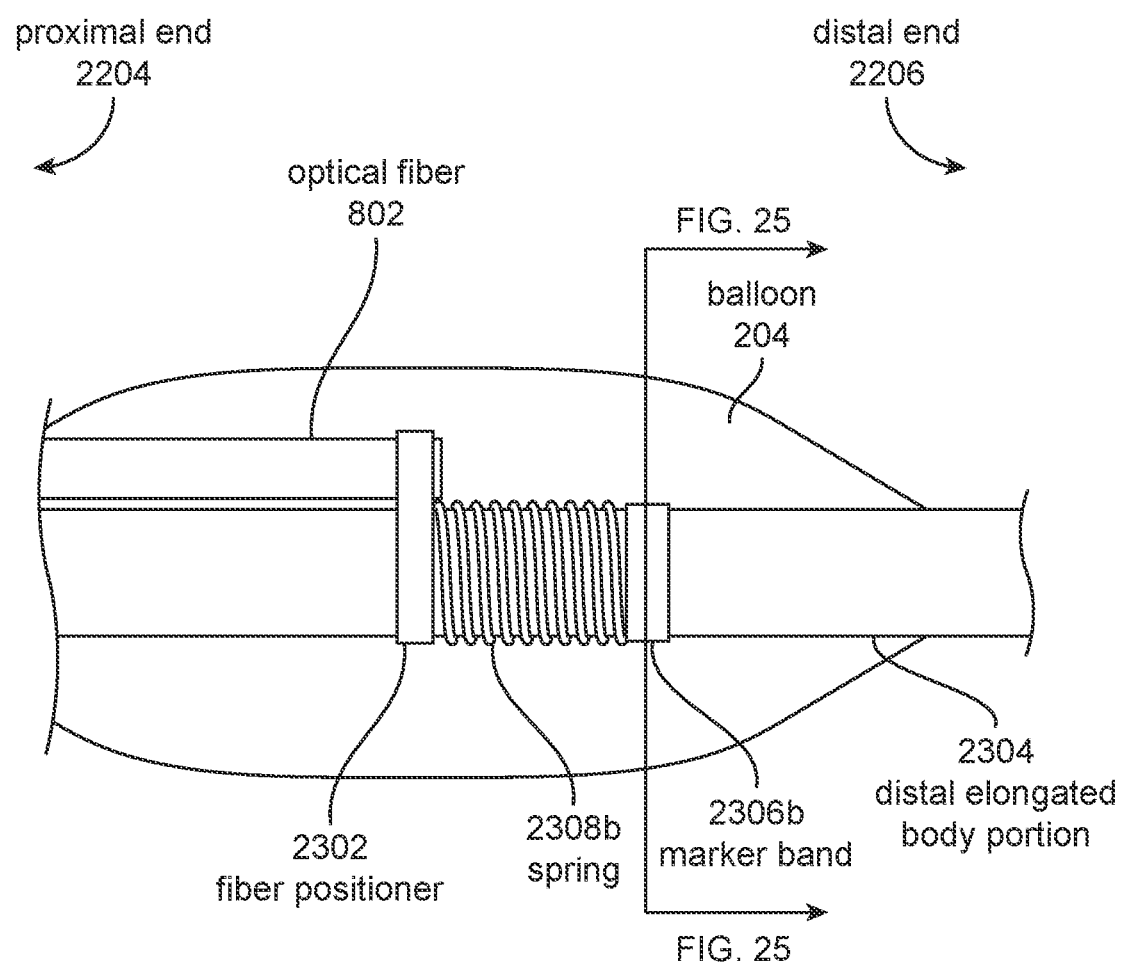
Figure 23C:
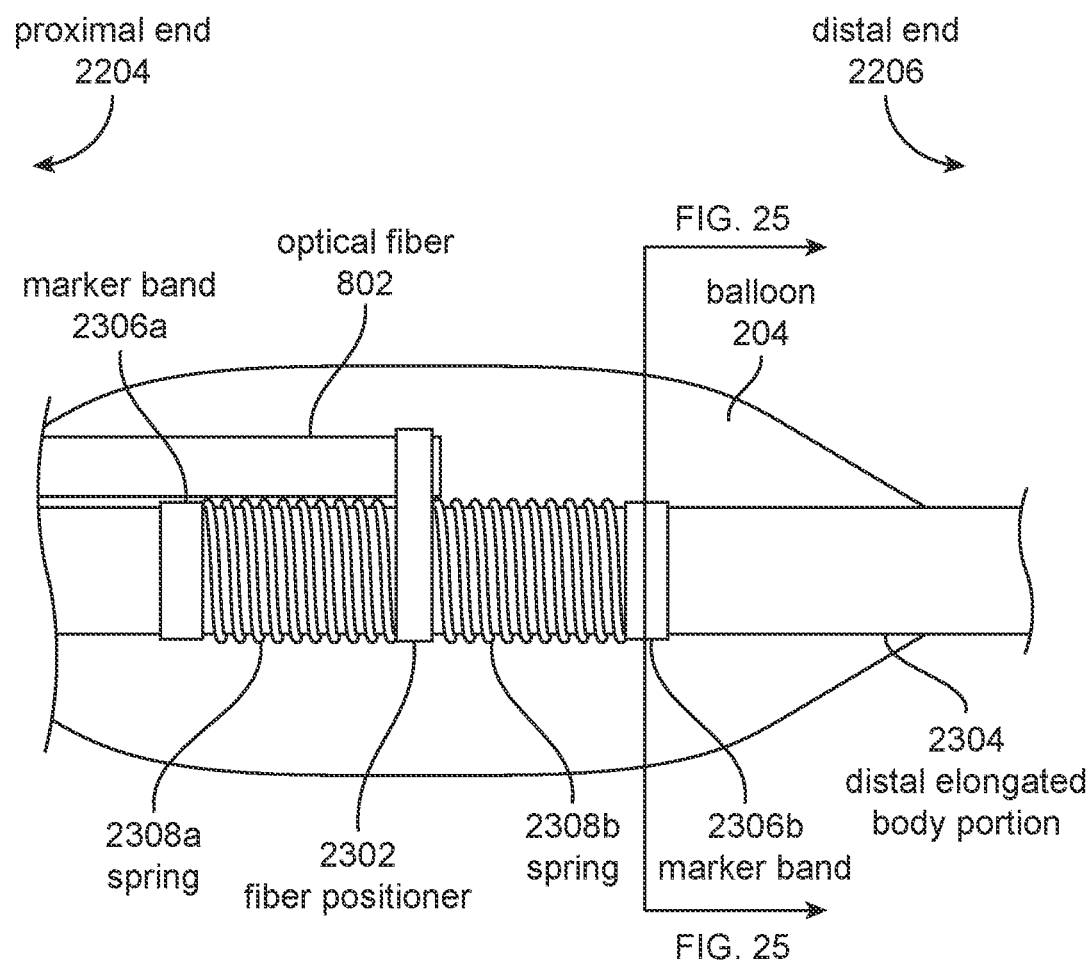

FIGS. 23A, 23B, and 23C illustrate diagrams of an IVL device including a movable fiber positioner, according to some examples. Specifically, FIG. 23A shows an IVL device including a spring 2308a attached to the fiber positioner 2302 proximal to the fiber positioner 2302. This spring 2308a may be attached to a permanent or semi-permanently fixed component of the IVL device, such as a marker band 2306a (as shown) or other component. A marker band 2306a may assist an operator with locating the IVL device within the vasculature of a patient.

In this example, the fiber positioner 2302 may rest at a nominal position with respect to the IVL device. An operator may then effectuate longitudinal movement on the fiber positioner 2302, either by interacting with the fiber positioner 2302 itself, or manipulating something fixedly coupled to the fiber positioner 2302, such as the optical fiber 802. When the fiber positioner 2302 is moved distally, it places the spring 2308a under tension, such that the spring 2308a wants to return to its nominal position. The operator may then lock the fiber positioner 2302, or the spring 2308a, in place while they perform a procedure. The operator may then unlock the fiber positioner 2302 or spring 2308a once the procedure is completed, allowing the spring 2308a to return to its nominal position prior to retracting the IVL device.

Likewise, when the fiber positioner 2302 is moved proximally, it places the spring 2308a under compression, such that the spring 2308a wants to return to its nominal position. Again, the operator may then lock the fiber positioner 2302, or the spring 2308a, in place while they perform a procedure. The operator may then unlock the fiber positioner 2302 or spring 2308a once the procedure is completed, again allowing the spring 2308a to return to its nominal position prior to retracting the IVL device.

In some examples, the nominal position of the spring 2308a may be a fully compressed state. In such examples, the operator would only be capable of pushing the fiber positioner 2302 distally, thus placing the spring 2308a under tension.

FIG. 23B illustrates a similar IVL device, however, in this example the spring 2308b is distal to the fiber positioner 2302. Also in this example, the fixed component, in this case a marker band 2306b, is also distal to the fiber positioner 2302. Once again, the marker band 2306b may assist an operator with locating the IVL device within the vasculature of a patient.

This means that, should the fiber positioner 2302 be moved distally, the spring 2308b would be placed under compression. Alternatively, should the fiber positioner 2302 be moved proximally, the spring 2308b would be placed under tension. In both cases, the spring 2308b would want to return to its nominal position, but the operator may lock the spring 2308b and/or the fiber positioner 2302 in place during the procedure.

As discussed with reference to FIG. 23A above, the nominal position of the spring 2308b may be a fully compressed state. However, due to the different position of spring 2308b as compared to spring 2308a, the operator may only be capable of pulling the fiber positioner 2302 proximally, thus placing the spring 2308b under tension.

In either case—a spring 2308 under compression or under tension—once an operator releases the spring 2308 (or component holding the spring 2308 in position), this compression or tension will want to release, returning the spring 2308 to its nominal position. This may assist returning the fiber positioner 2302, and the optical fiber 802, to this nominal position. In the case of spring 2308a, because the tension is formed by moving the fiber positioner 2302 distally, this tension may facilitate the return of the fiber positioner 2302 and optical fiber 802 proximally to its nominal position. In this case of spring 2308b, because the tension is formed by moving the fiber positioner 2302 proximally, this tension may facilitate the return of the fiber positioner 2302 and the optical fiber 802 distally to its nominal position.

FIG. 23C combines the features of FIGS. 23A and 23B. In this example, proximal spring 2308a and distal spring 2308b are both coupled to the fiber positioner 2302. Once again, the permanent or semi-permanent fixtures to which these springs 2308 are coupled are marker bands 2306, in this case proximal marker band 2306a and distal marker band 2306b.

In this example, moving the fiber positioner 2302 proximally would place the spring 2308a under compression and the spring 2308b under tension. This may cause more resistance, with the springs 2308 wanting to return to their nominal position. Alternatively, moving the fiber positioner distally would place the spring 2308a under tension and the spring 2308b under compression.

In other examples, springs with lower spring constants could be used due to this additive resistance. As springs with lower spring constants could be smaller, this may facilitate the creation of a smaller crossing profile for the IVL device.

In the example shown in FIG. 23C, the nominal position for the fiber positioner 2302 could see the spring 2308a fully compressed or the spring 2308b fully compressed, but not both. If the nominal position of the fiber positioner 2302 had both spring 2308a and spring 2308b under full compression, the fiber positioner would likely not be capable of longitudinal movement.

Figure 24:
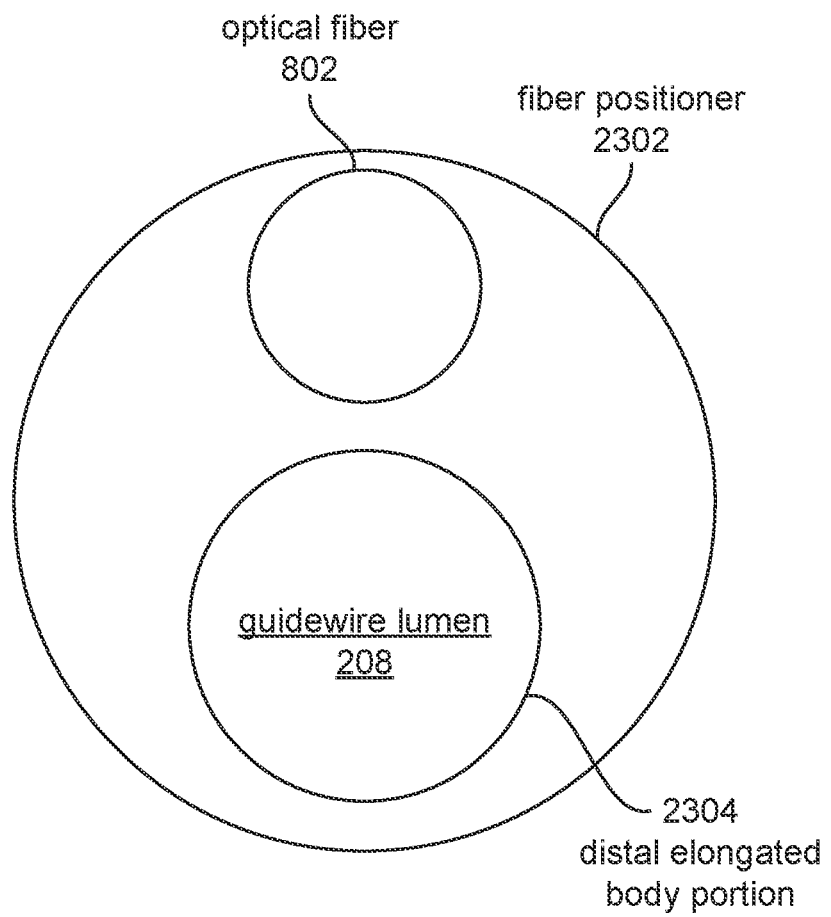
FIG. 24 illustrates a cross-sectional view of the IVL device of FIG. 23A.

FIG. 24 illustrates a cross-sectional view of the IVL device of FIG. 23A. In this example, as the spring 2308a and the marker band 2306a are proximal to the fiber positioner 2302, they would not be seen.

Figure 25:
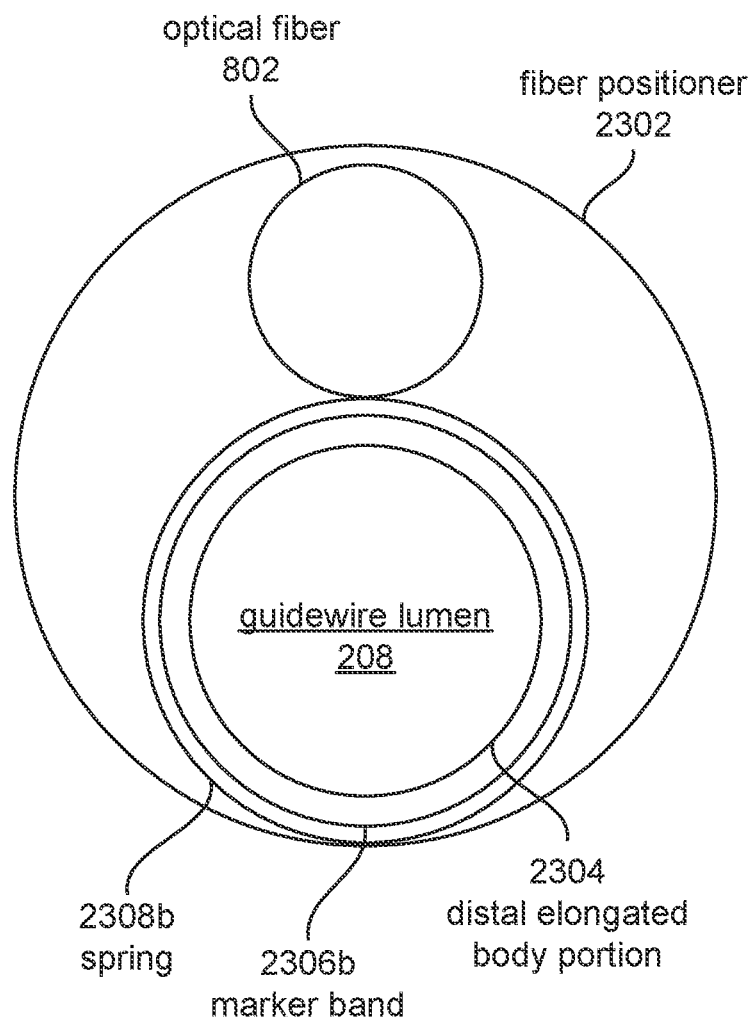
FIG. 25 illustrates a cross-sectional view of the IVL device of FIGS. 23B and 23C.

FIG. 25 illustrates a cross-sectional view of the medical device of FIGS. 23B and 23C. In this example, because the spring 2308b and the marker band 2306b are distal to the fiber positioner 2302, they would be seen.

Another problem found in prior art solutions to longitudinal movement of the optical fiber is that the optical fiber may also want to move rotationally with respect to the guidewire lumen (or central axis, or IVL device as a whole, etc.) Especially in instances where the optical fiber is manipulated itself by the operator, the optical fiber may try to "kick," where it wants to move at an angle in addition to moving longitudinally. This is a problem, because, as the optical fiber becomes more radially offline—i.e., rotationally misaligned from its nominal position with respect to the central axis—the longitudinal translation of the optical fiber may see increased resistance, making it more difficult for an operator to longitudinally displace the optical fiber. Permitting the optical fiber to move rotationally may also increase wear and tear on the optical fiber, potentially causing issues with durability in the optical fiber.

The present disclosure also seeks to remedy this deficiency in prior art solutions. Through the below disclosures, a fiber positioner may be rotationally fixed to a catheter. Because a provided optical fiber would run through the fiber positioner, or be otherwise coupled to the fiber positioner, this would prevent the optical fiber from rotating with respect to the catheter. Thus, by knowing the position of the catheter, through means such as a provided marker band, an operator would be able to know the exact position of the optical fiber, longitudinally and axially, in order to deliver the most efficacious treatment.

Figure 26:
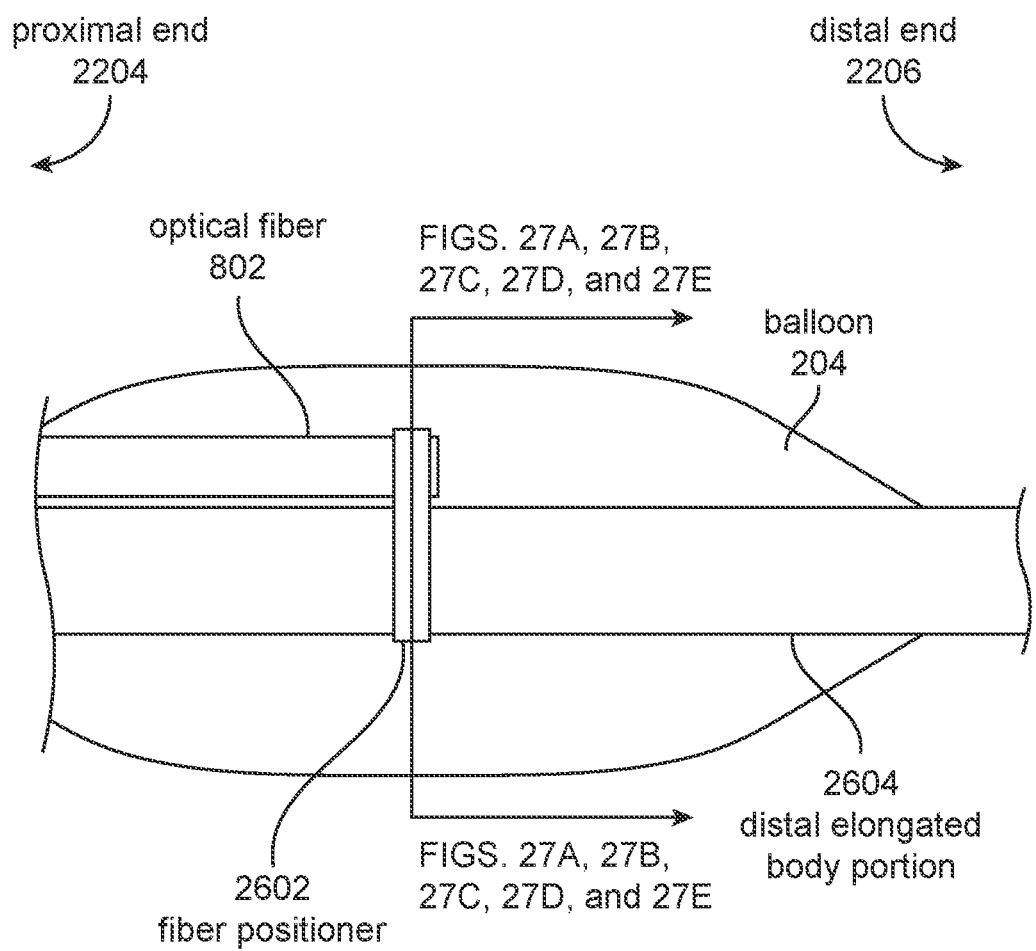
FIG. 26 illustrates a diagram of an IVL device with the distal fiber end of an optical fiber held in place.

FIG. 26 illustrates a diagram of an IVL device with the distal fiber end of an optical fiber 802 held in place. The purpose of FIG. 26 is to orient a viewer as to where the cross-sectional depictions of fiber positioner 2602 as seen in FIGS. 27A, 27B, 27C, 27D, and 27E take place. However, it is understood that previous perspective views of the fiber positioner 2602, such as fiber positioners as shown in FIGS. 11A, 11B, 11C, and 11D may also be used in conjunction with this disclosure.

Figure 27A:
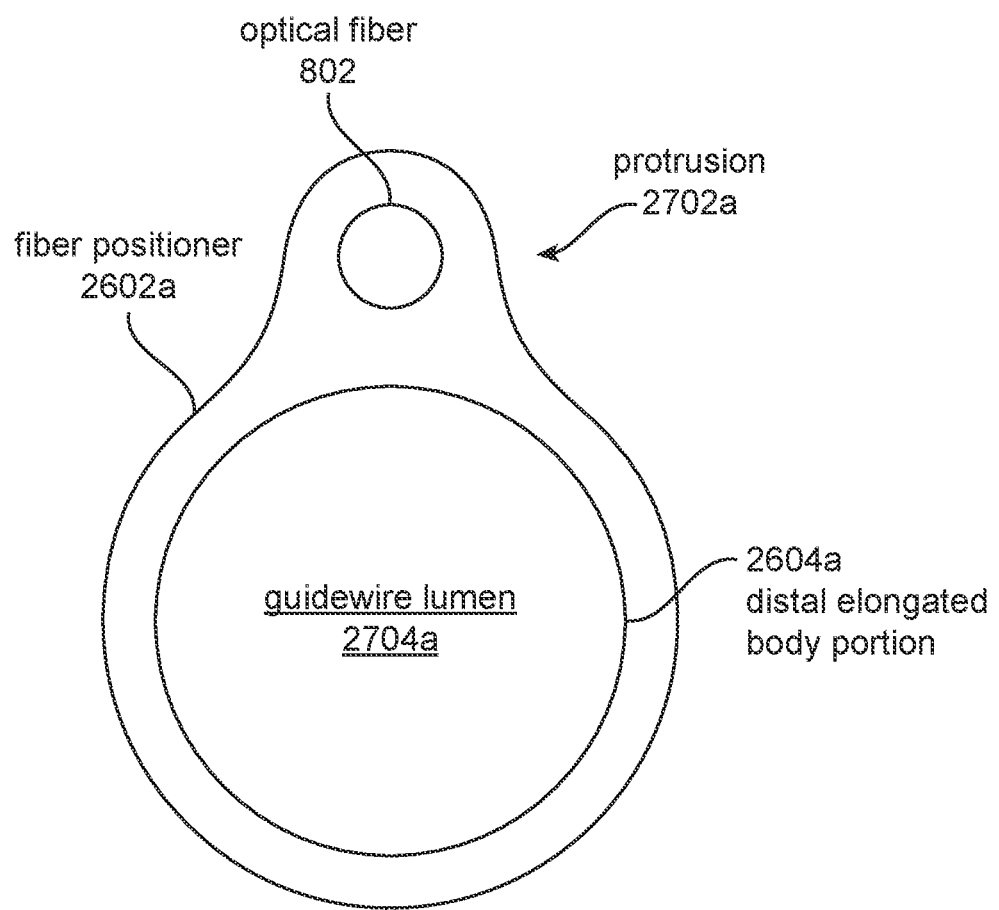
FIGS. 27A, 27B, 27C, 27D, and 27E illustrate various examples of cross-sections of the IVL device of FIG. 26.

FIGS. 27A, 27B, 27C, 27D, and 27E illustrate various examples of cross-sections of the IVL device of FIG. 26. Specifically, FIG. 27A illustrates a circular fiber positioner 2602a including a circular distal elongated body portion 2604a. In this example, the fiber positioner 2602a includes a protrusion 2702a for receiving the optical fiber 802. This example fiber positioner 2602a and distal elongated body portion 2604a are each shown with an eccentricity of zero, which may allow for the aforementioned rotation of the optical fiber 802.

Figure 27B:
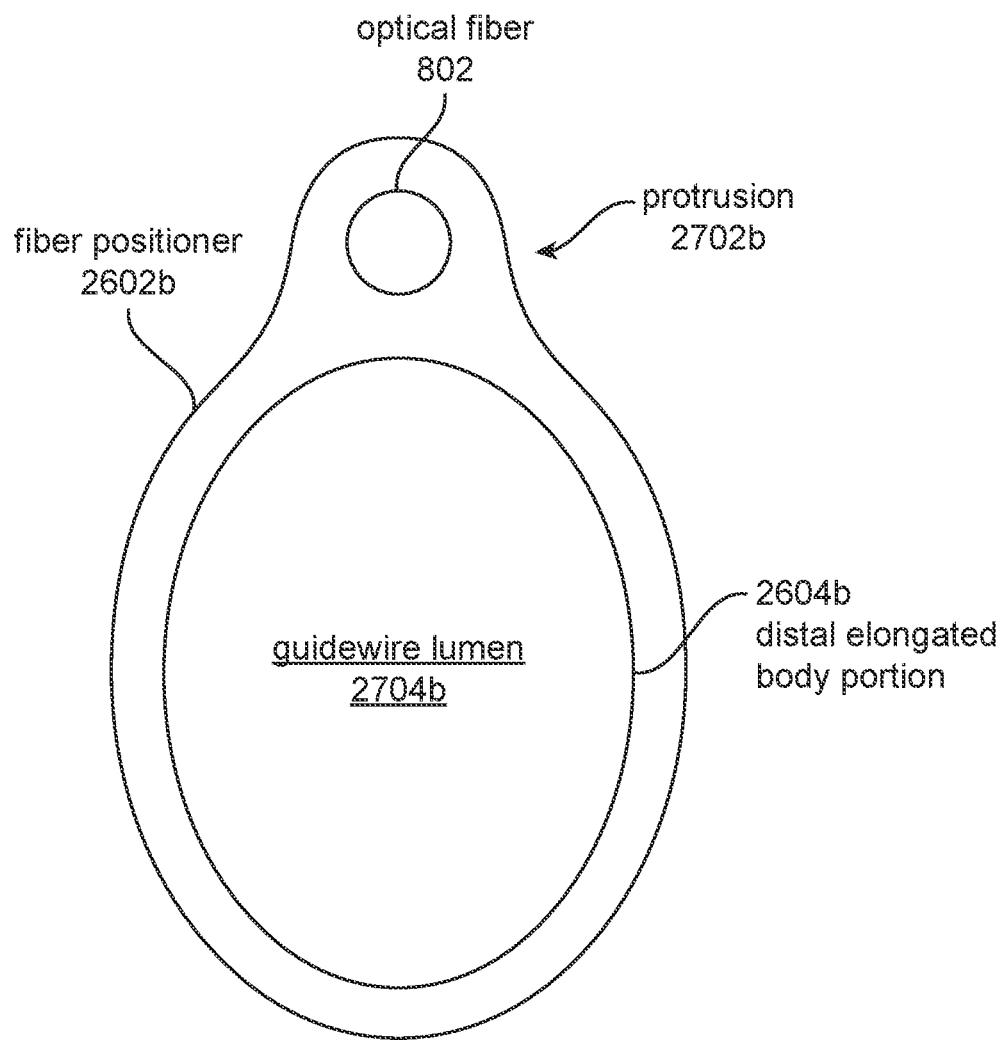

FIG. 27B illustrates an oval-shaped fiber positioner 2602b surrounding an oval-shaped distal elongated body portion 2604b. The specific shape of the oval for both the fiber positioner 2602b and the distal elongated body portion 2604b is not important, so long as the eccentricity of each is greater than zero and less than one. This is because, with an eccentricity of greater than zero and less than one, the fiber positioner 2602b is unable to rotate about the distal elongated body portion 2604b, thus preserving the axial location of the optical fiber 802 with respect to the distal elongated body portion 2604b. Also shown in FIG. 27B is a protrusion 2702b for receiving the optical fiber 802 in the fiber positioner 2602b.

Figure 27C:
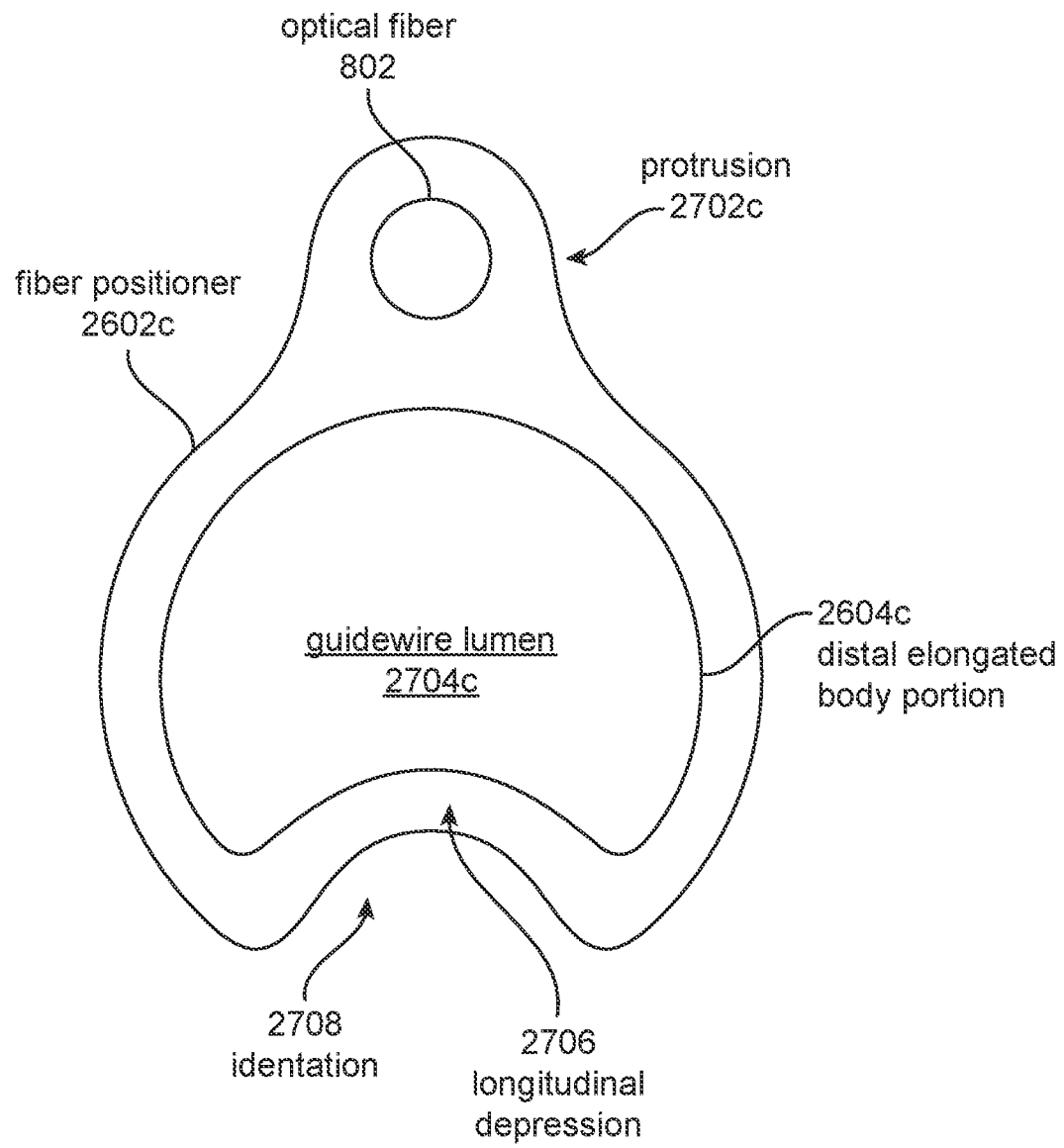

FIG. 27C illustrates a distal elongated body portion 2604c including a longitudinal depression 2706. In this example, the fiber positioner 2602c includes an indentation 2708 configured to be accepted by the longitudinal depression 2706. In this way, the fiber positioner 2602c is prevented from rotating about the distal elongated body portion 2604c, thus preserving the axial location of the optical fiber 802 with respect to the distal elongated body portion 2604c. Additionally, the longitudinal depression 2706 may run the entire length of the distal elongated body portion 2604c, or it may only run for a portion of the distal elongated body portion 2604c. In such examples where the longitudinal depression 2706 does not extend the entire length of the distal elongated body portion, the longitudinal depression 2706 may prevent the fiber positioner 2602c from moving longitudinally further than this longitudinal depression 2706 length.

Also shown in FIG. 27C is a protrusion 2702c for receiving the optical fiber 802 in the fiber positioner 2602c. In all of FIGS. 27A, 27B, and 27C, these protrusions 2702 are by way of example only, and it is understood that other solutions for maintaining the optical fiber 802 in the fiber positioner 2602 would be equally operable.

Figure 27D:
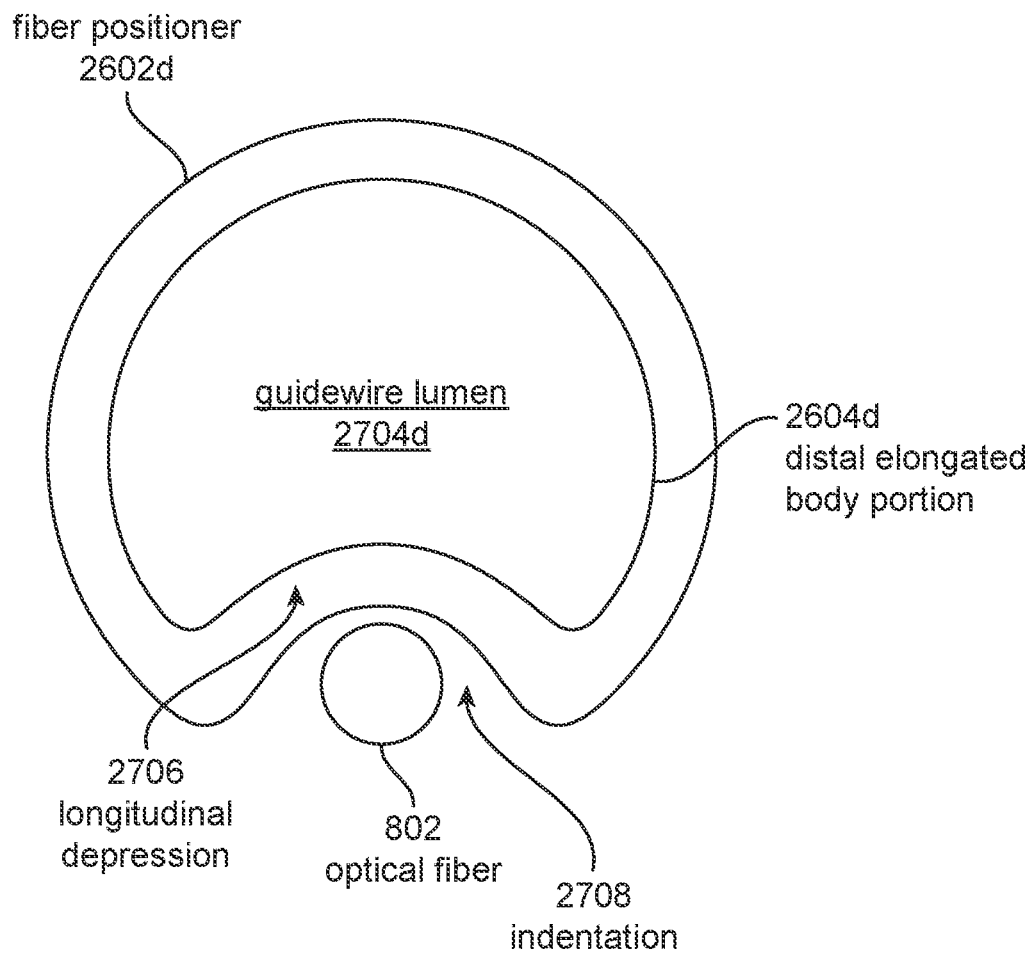

For example, FIG. 27D illustrates another distal elongated body portion 2604d including a longitudinal depression 2706, along with another fiber positioner 2602d including an indentation 2708 configured to be accepted by the longitudinal depression 2706. However, in this case, the optical fiber 802 may nest in the indentation 2708 of the fiber positioner 2602d on the side opposite the longitudinal depression 2706 of the distal elongated body portion 2604d. While the illustration of FIG. 27D is simplified, it is understood that the indentation 2708 may further surround the optical fiber 802 in order to prevent the optical fiber 802 from decoupling from the fiber positioner 2602d. "Decoupling" in this context is intended to be interpreted as one object becoming not coupled from another object, either actively or passively.

Figure 27E:
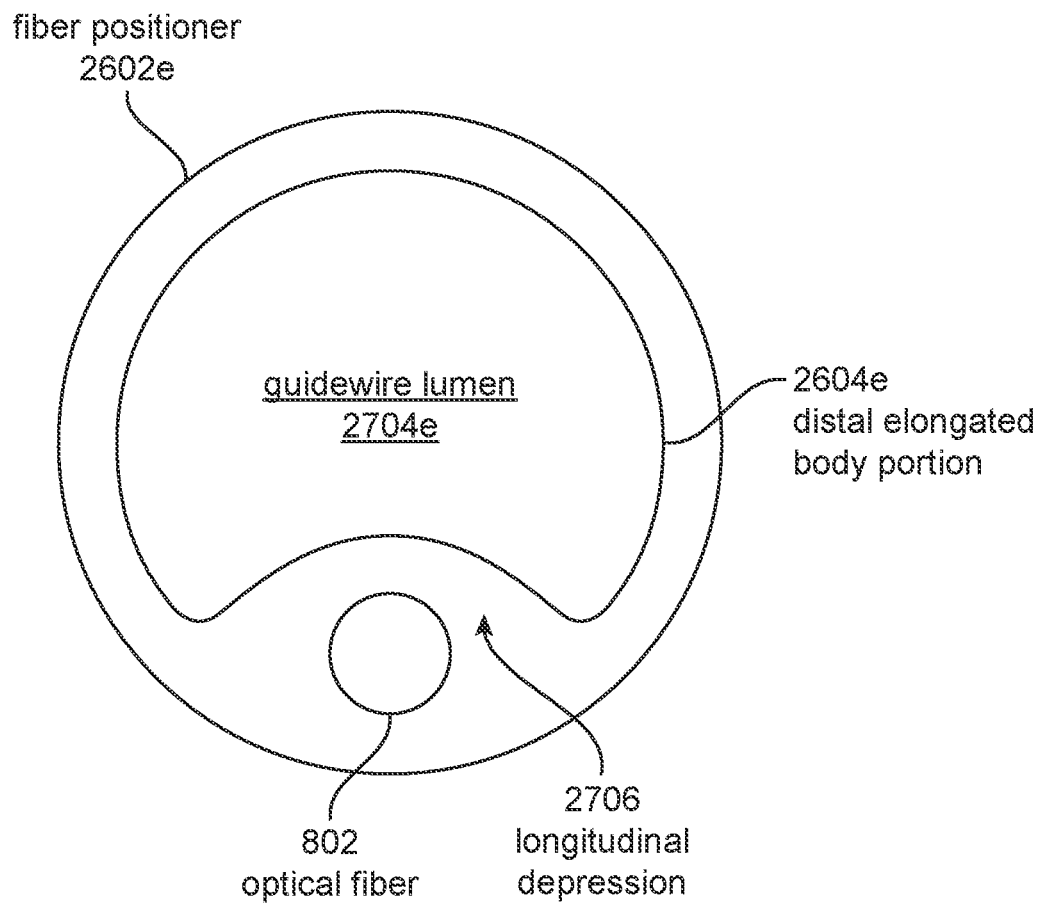

FIG. 27E illustrates a distal elongated body portion 2604e including a longitudinal depression 2706, but in this example, the surrounding fiber positioner 2602e does not include an indentation. Instead, the optical fiber 802 extends near the longitudinal depression 2706 through the fiber positioner 2602e. In this example, the fiber positioner 2602e is prevented from rotating about the distal elongated body portion 2604e because the longitudinal depression 2706 prevents the optical fiber 802 itself from rotating. This is another method by which the axial location of the optical fiber 802 with respect to the distal elongated body portion 2604e may be preserved.

Figure 28A:
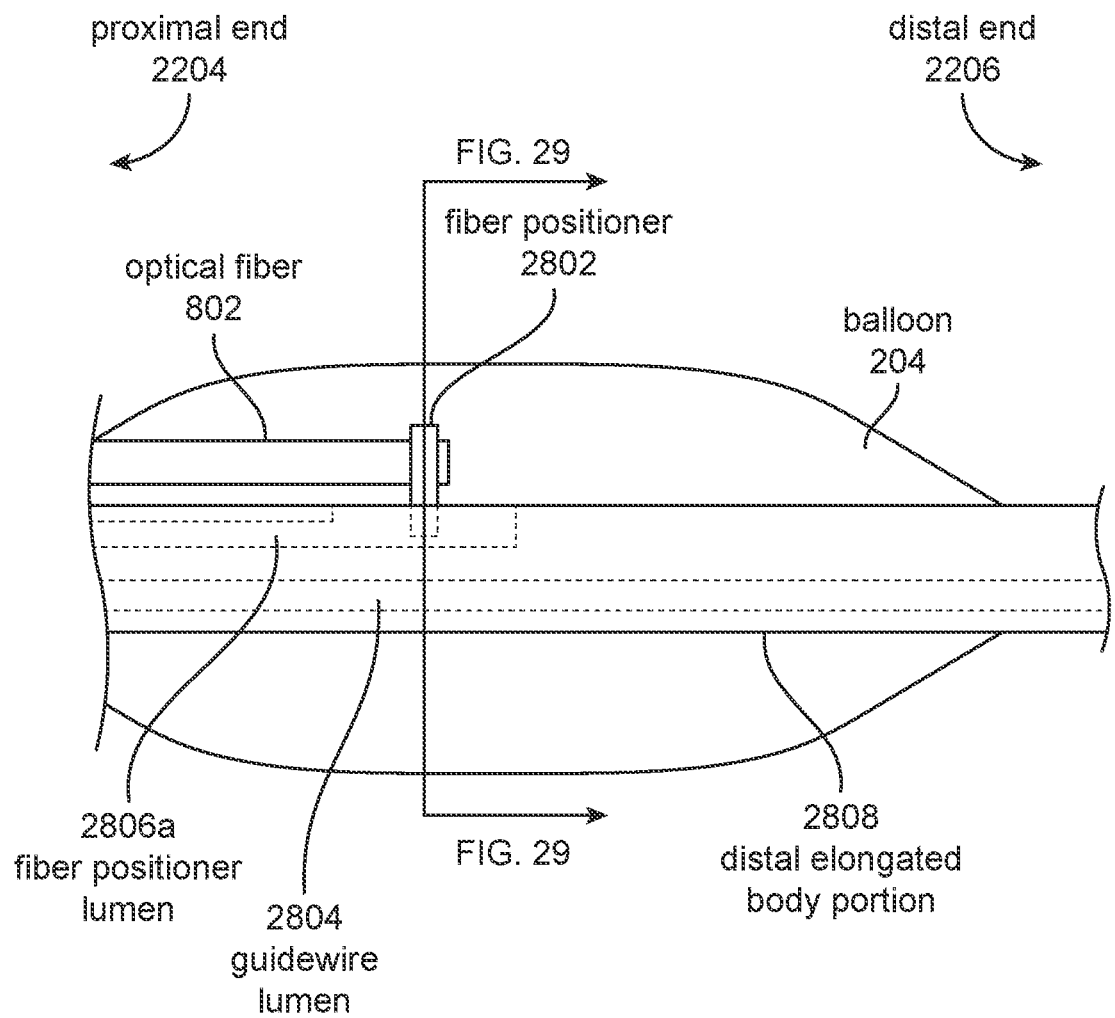
FIGS. 28A and 28B illustrate diagrams of an IVL device including a fiber positioner lumen.
Figure 28B:
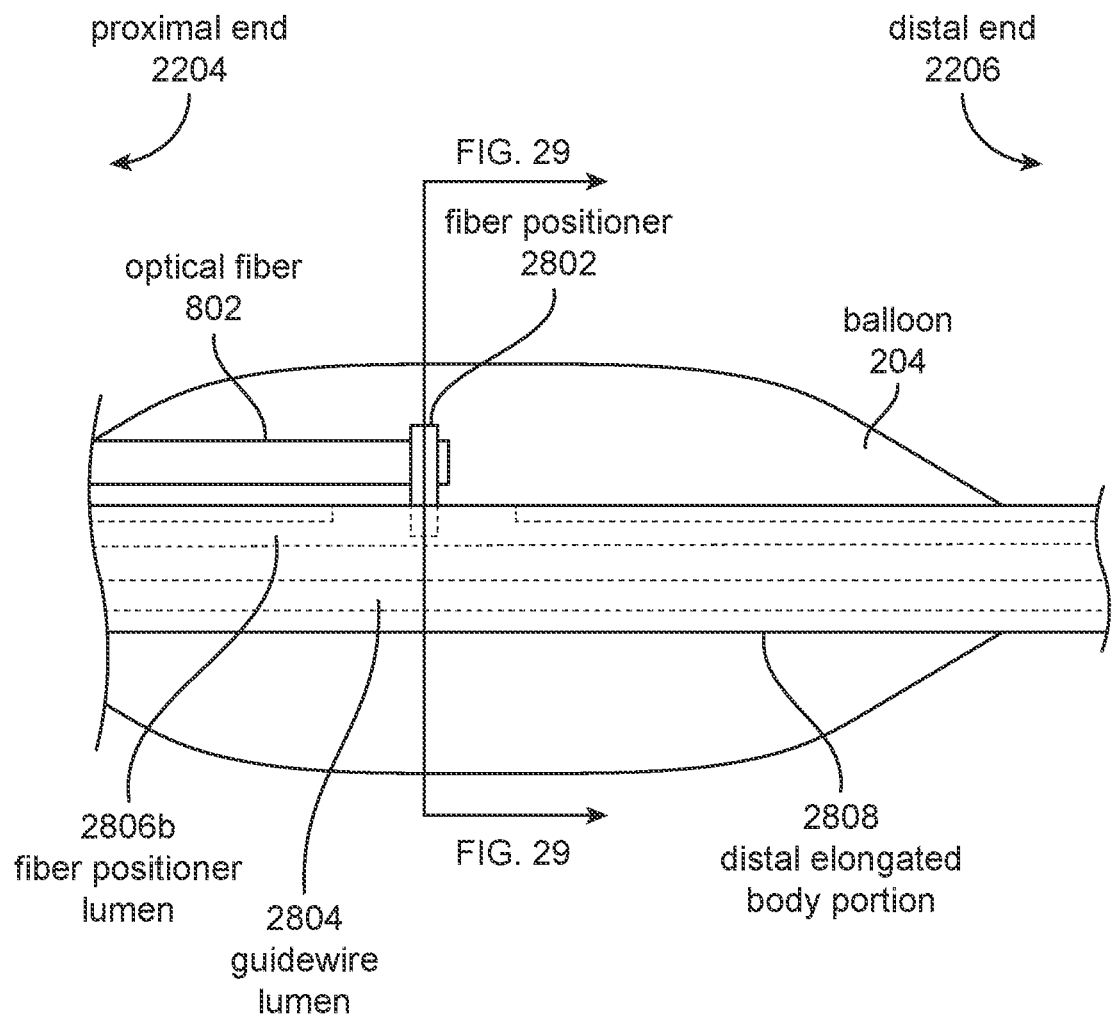

FIGS. 28A and 28B illustrate diagrams of an IVL device including a fiber positioner lumen. In both FIGS. 28A and 28B, a fiber positioner 2802 is shown coupled to a distal elongated body portion 2808. In these examples, however, the fiber positioner 2802 does not surround the distal elongated body portion 2808. Instead, multiple lumens run through the catheter, one being a guidewire lumen 2804, and the other being a fiber positioner lumen 2806.

Specifically, in FIG. 28A, the fiber positioner lumen 2806a terminates proximal to the distal end 2206. This point of termination may prevent the fiber positioner 2802 from moving distally any further. In FIG. 28B, the fiber positioner lumen 2806b extends the length of the distal elongated body portion 2808. In both the fiber positioner lumen 2806a and the fiber positioner lumen 2806b, a slit may be present in order to fluidly couple an inner portion of the fiber positioner lumen 2806 to an exterior of the distal elongated body portion 2808. This is illustrated in FIG. 29, which is a cross-sectional view of the IVL device of FIGS. 28A and 28B.

Figure 29:
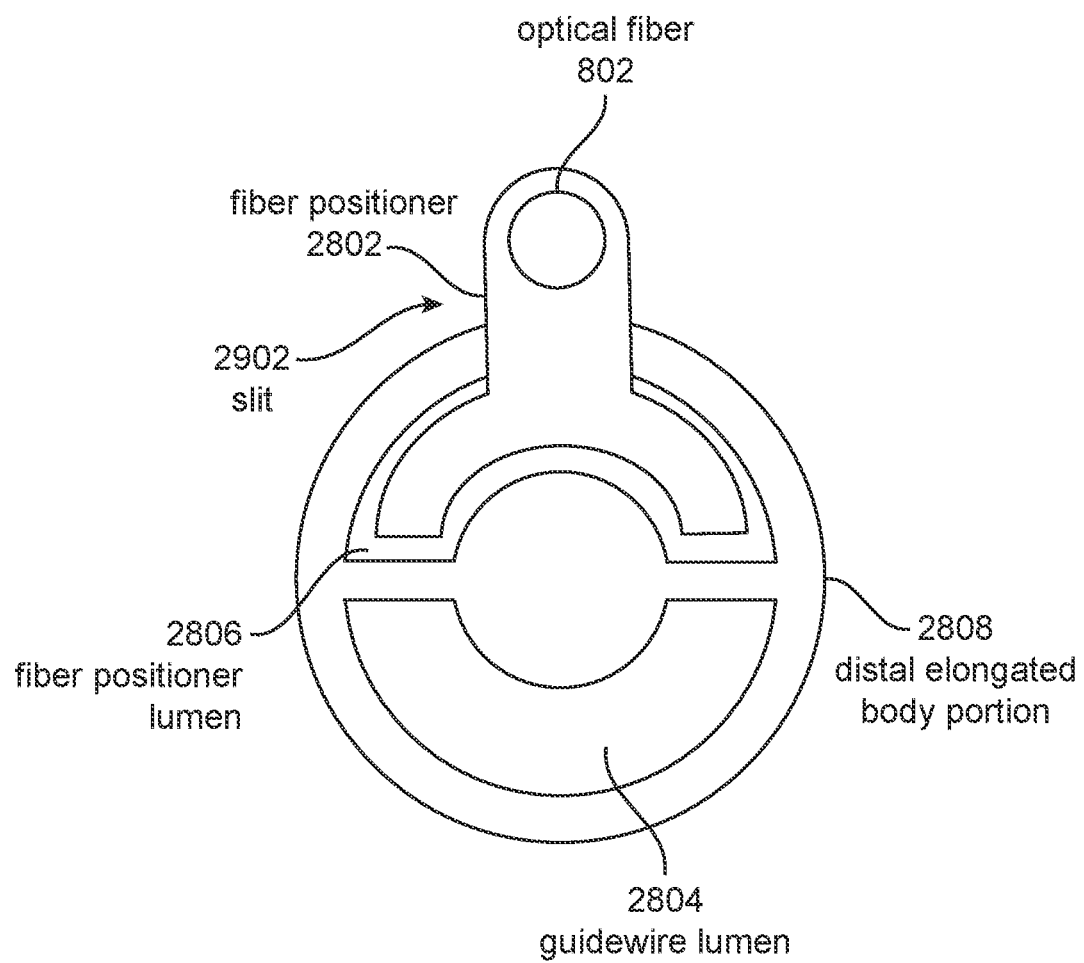
FIG. 29 illustrates a cross-sectional view of the IVL device of FIGS. 28A and 28B.

As seen in FIG. 29, a slit 2902 is present through which a portion of the fiber positioner 2802 may extend. The purpose of this is so that the optical fiber 802 is exterior the distal elongated body portion 2808 such that any emitted laser energy is not interfered with by the distal elongated body portion 2808. As can also be seen in FIG. 29, a portion of the fiber positioner 2802 may be shaped such that it aligns at least partially with the fiber positioner lumen 2806. This is another manner in which the fiber positioner 2802 may be at least partially, if not fully, rotationally fixed with respect to the distal elongated body portion 2808, thus preserving the axial location of the optical fiber 802 with respect to the distal elongated body portion 2808.

Additionally, the slit 2902 may only extend a certain distance along the distal elongated body portion 2808. In this manner, the proximal and distal termination points of the slit 2902 may act as stopping points for the longitudinal movement of the fiber positioner 2802. That is to say, the proximal termination point of the slit 2902 may prevent the fiber positioner 2802 from moving longitudinally any further proximally, and the distal termination point of the slit 2902 may prevent the fiber positioner 2802 from moving longitudinally any further distally.

Figure 30:
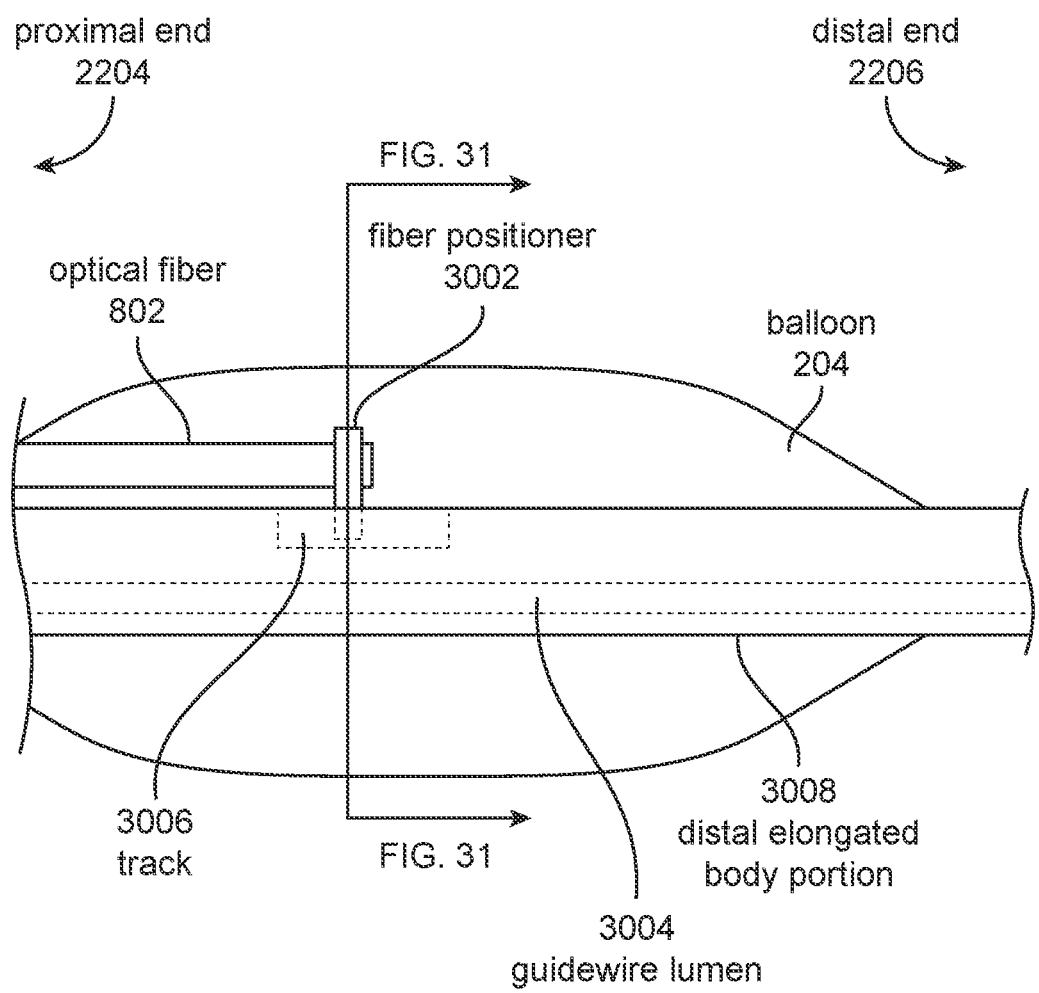
FIG. 30 illustrates a diagram of an IVL device including a track.

FIG. 30 illustrates a diagram of an IVL device including a track 3006. The track 3006 may share some similarities to the fiber positioner lumen 2806, but does not extend proximally back to a controller in a way a lumen might. The track 3006 includes proximal and distal points of termination, thus controlling how far the fiber positioner 3002 may move longitudinally in both the proximal and distal directions.

Figure 31:
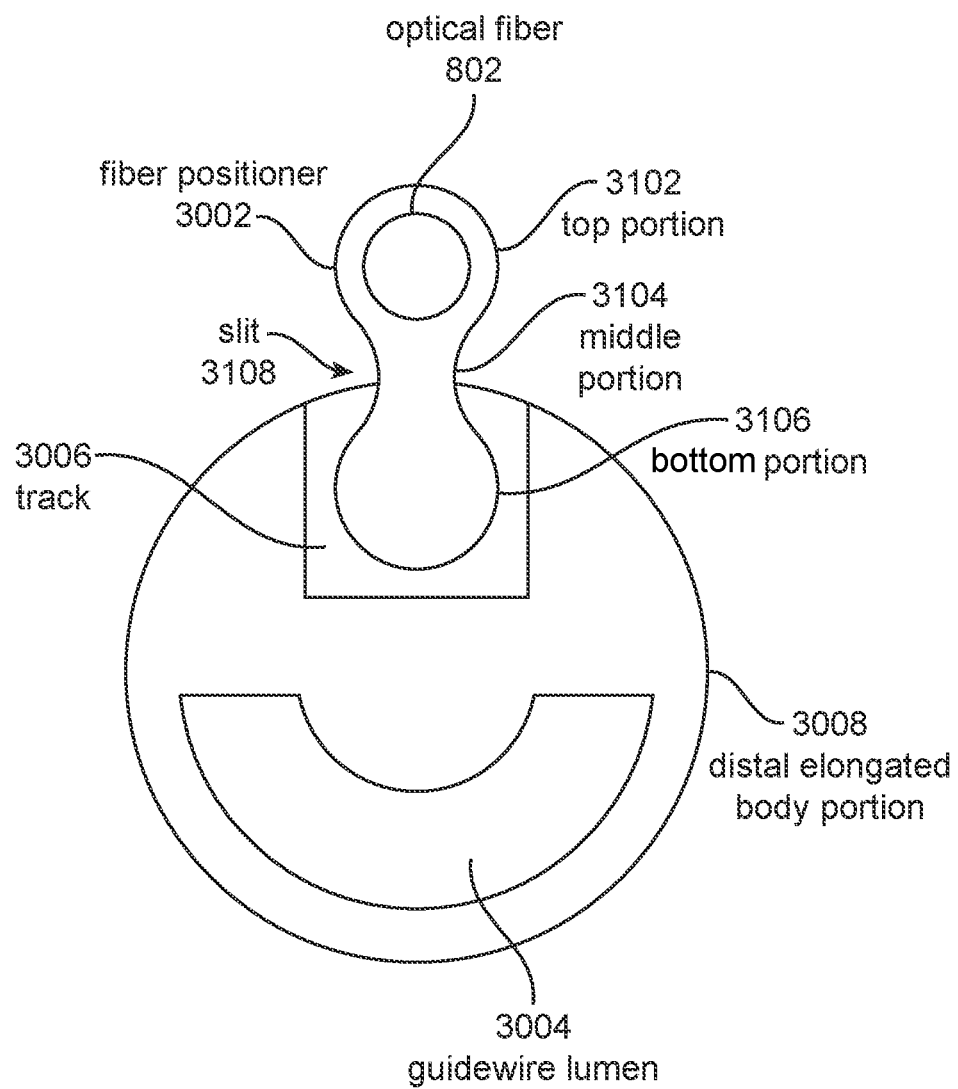
FIG. 31 illustrates a cross-sectional view of the IVL device of FIG. 30.

FIG. 31 illustrates a cross-sectional view of the IVL device of FIG. 30. From this perspective, one example of how a fiber positioner 3002 is rotationally fixed with respect to the distal elongated body portion 3008 can be seen. A slit 3108, running either a portion of the length of the track 3006 or the entire length of the track 3006 permits the fiber positioner 3002 to extend from inside the track 3006 to outside the distal elongated body portion 3008.

In this example, the fiber positioner 3002 includes a top portion 3102, a middle portion 3104, and a bottom portion 3106. The top portion 3102 can be seen surrounding the optical fiber 802, thus keeping the optical fiber 802 fixed to the fiber positioner 3002. The bottom portion 3106 can be seen seated within the track. The middle portion 3104 is shown having a width that is less than a width of the top portion 3102 and the bottom portion 3106, and this middle portion 3104 is located where the slit 3108 may be. By having larger widths than the middle portion 3104, the bottom portion 3106 is prevented from sliding out of the track 3006, and the top portion 3102 is prevented from sliding into the track 3006. The fiber positioner 3002 is unable to move rotationally in the track 3006, thus preserving the axial location of the optical fiber 802 with respect to the distal elongated body portion 3008.

In any or all of the preceding disclosure pertaining to fiber positioners, it is understood that the optical fiber 802 may either be fixedly coupled or slidably coupled to the fiber positioner.

Figure 32:
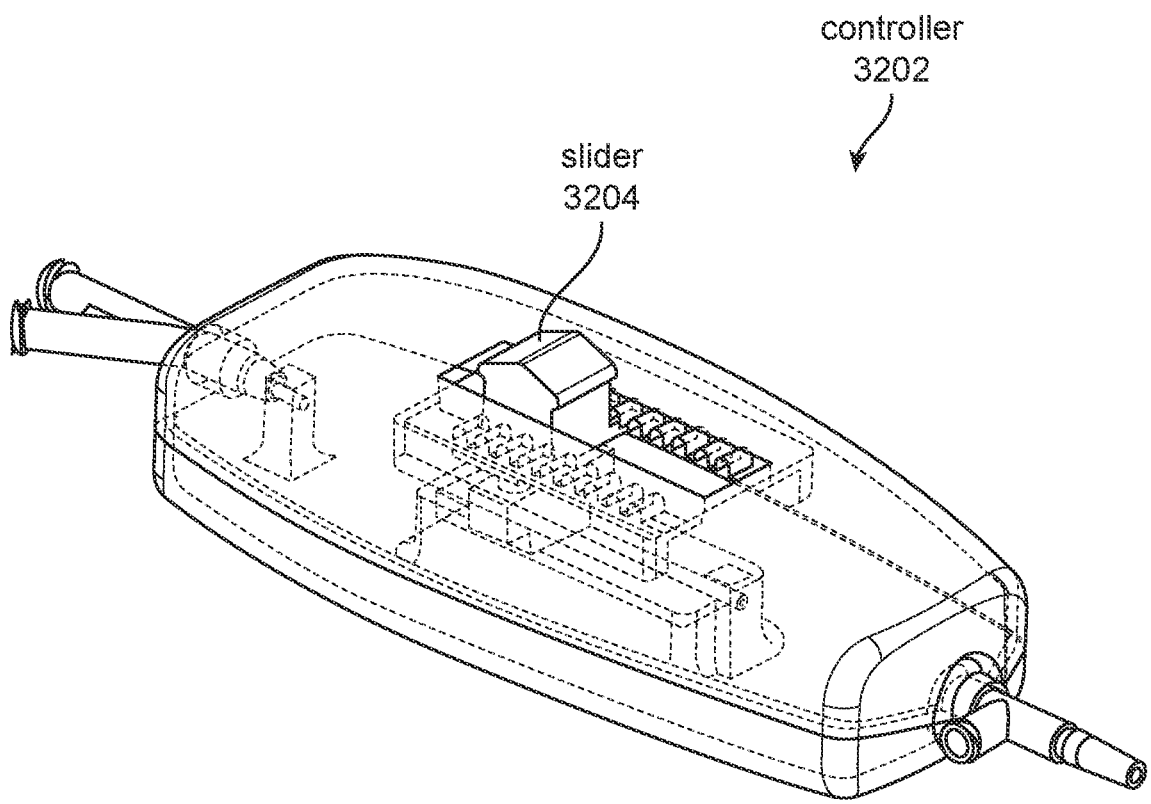
FIG. 32 illustrates a perspective view of a controller, according to some examples.
Figure 33:
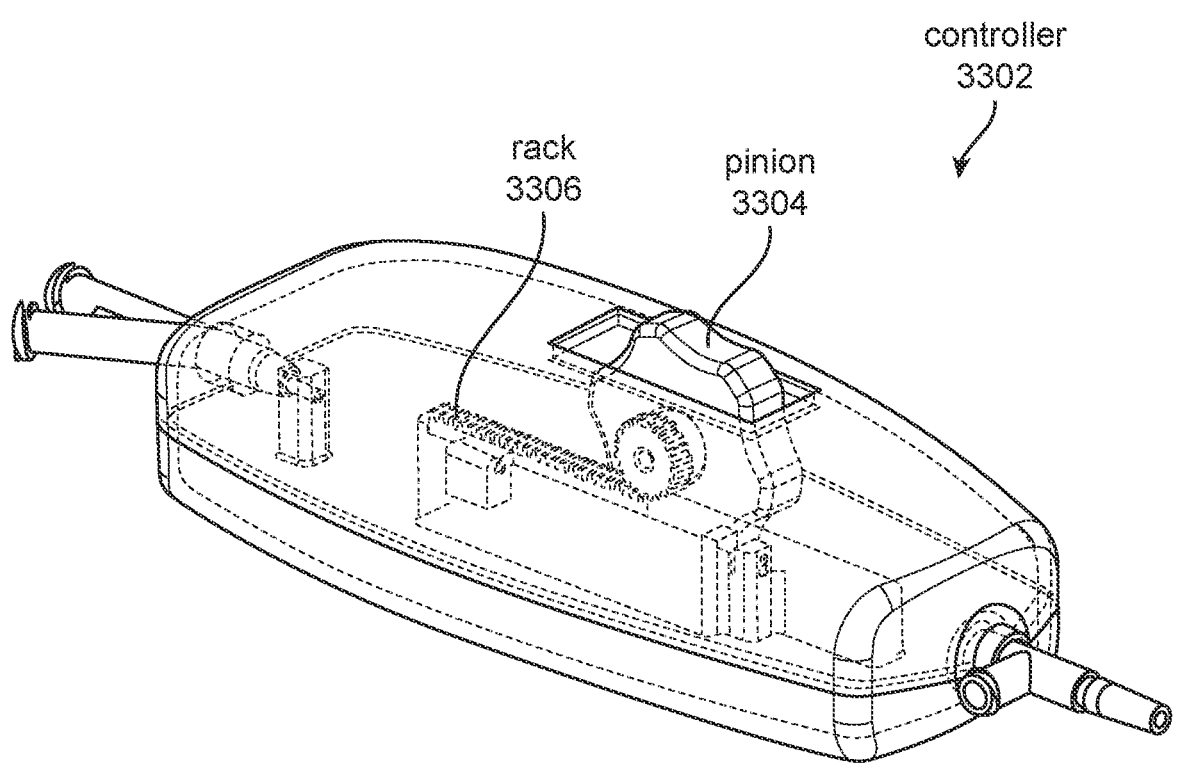
FIG. 33 illustrates a perspective view of an additional example controller.

FIG. 32 illustrates a perspective view of an example controller 3202, and FIG. 33 illustrates a perspective view of another example controller 3302. Specifically, FIG. 32 shows a controller 3202 including a slider 3204. The slider 3204 may be coupled to a catheter, the elongated body 302, and/or the optical fiber 802. This slider 3204 may permit longitudinal translation of any or all of these elements. In some cases, the slider 3204 may be used for repositioning the elongated body 302 when at or near a treatment site. In additional cases, the slider 3204 may be used for repositioning the optical fiber 802 within the elongated body 302, such that the elongated body 302 may not need to be moved, at often or at all, during a treatment.

FIG. 33 specifically shows a controller 3302 including a rack 3306 and pinion 3304. The rack 3306 and pinion 3304 achieve the longitudinal translation of the catheter, elongated body 302, and/or the optical fiber 802 in an additional manner. Instead of moving a slider 3204, an operator may turn the pinion 3304 to effectuate longitudinal movement on the rack 3306. While not shown in FIG. 32 or 33, any additional methods of imparting longitudinal movement on the catheter, the elongated body 302, and/or the optical fiber 802 are considered operable with the rest of the present disclosure.

FIGS. 34-38 illustrate bottom views of various example controllers including optical fiber 802 movement capabilities. These controllers may feature the slider 3204 of FIG. 32, and/or the rack 3306 and pinion 3304 of FIG. 33 for imparting movement on the optical fiber 802. These are manners in which the solution to the problems in the prior art mentioned with reference to FIGS. 23A, 23B, and 23C may be located external to a catheter.

Figure 34:
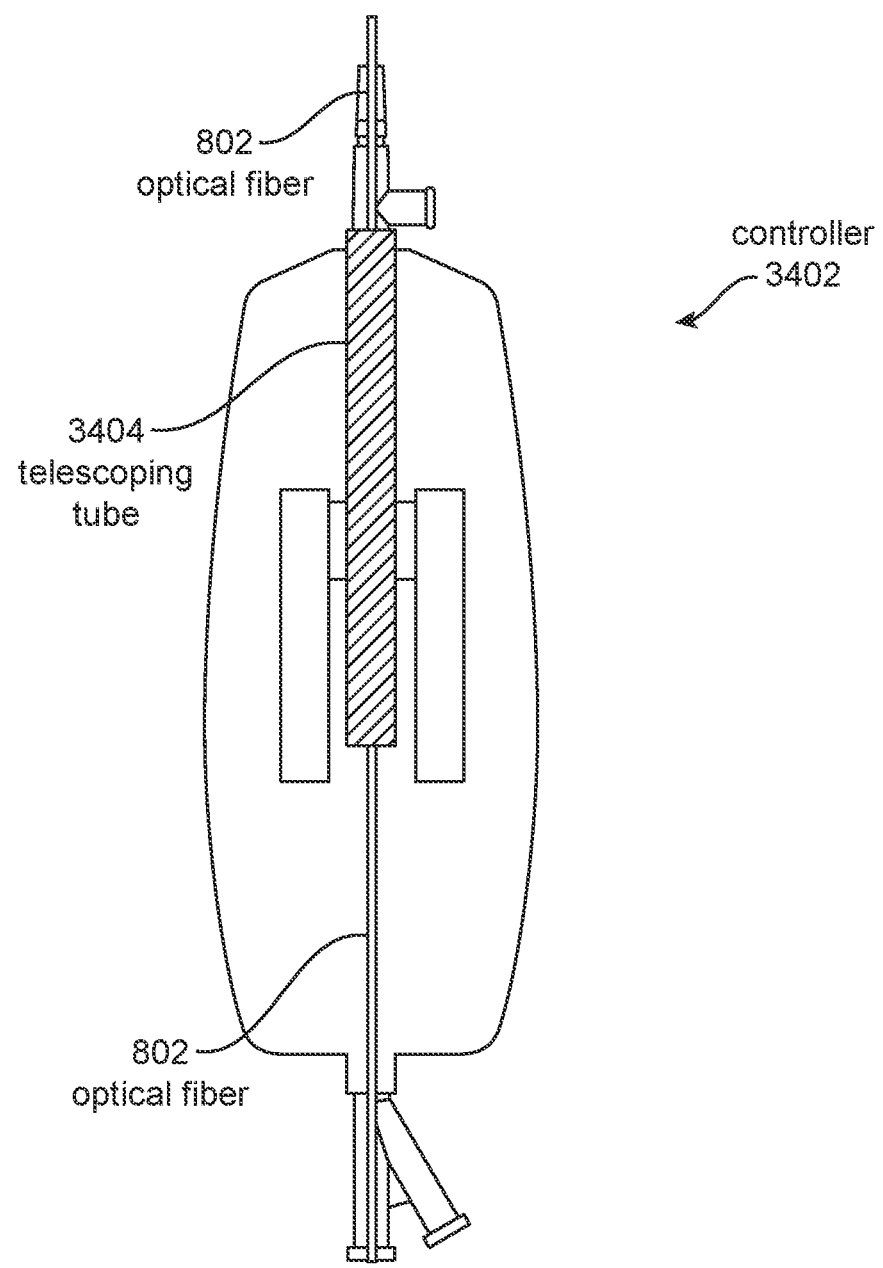
FIGS. 34, 35, 36, 37, and 38 illustrate bottom views of various example controllers including optical fiber movement capabilities.

Specifically, FIG. 34 shows a controller 3402 including a telescoping tube 3404. The telescoping tube 3404 may include an inner tube slidably coupled to an outer tube. Either or both of the outer tube and the inner tube may be stainless steel hypotubes. In such an example, the outer tube may be fixedly coupled to the controller 3402 or an optical fiber lumen. The inner tube may be fixedly coupled to the optical fiber 802. In such examples, when the inner tube slides through the outer tube, this longitudinal movement would be imparted on the optical fiber 802. The purpose of such a telescoping tube 3404 may be permit pushing of the optical fiber 802 longitudinally without permitting the optical fiber 802 to buckle.

Figure 35:
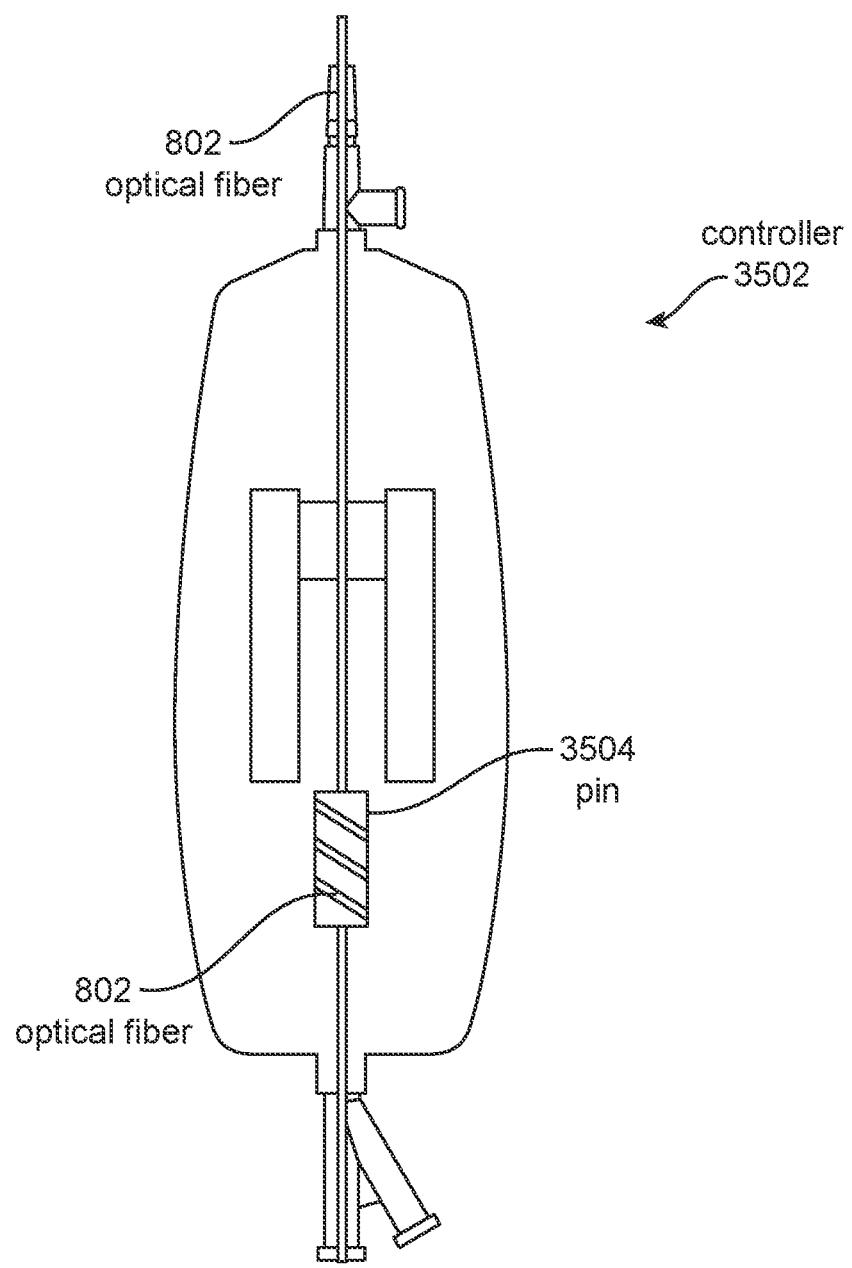
Figure 36:
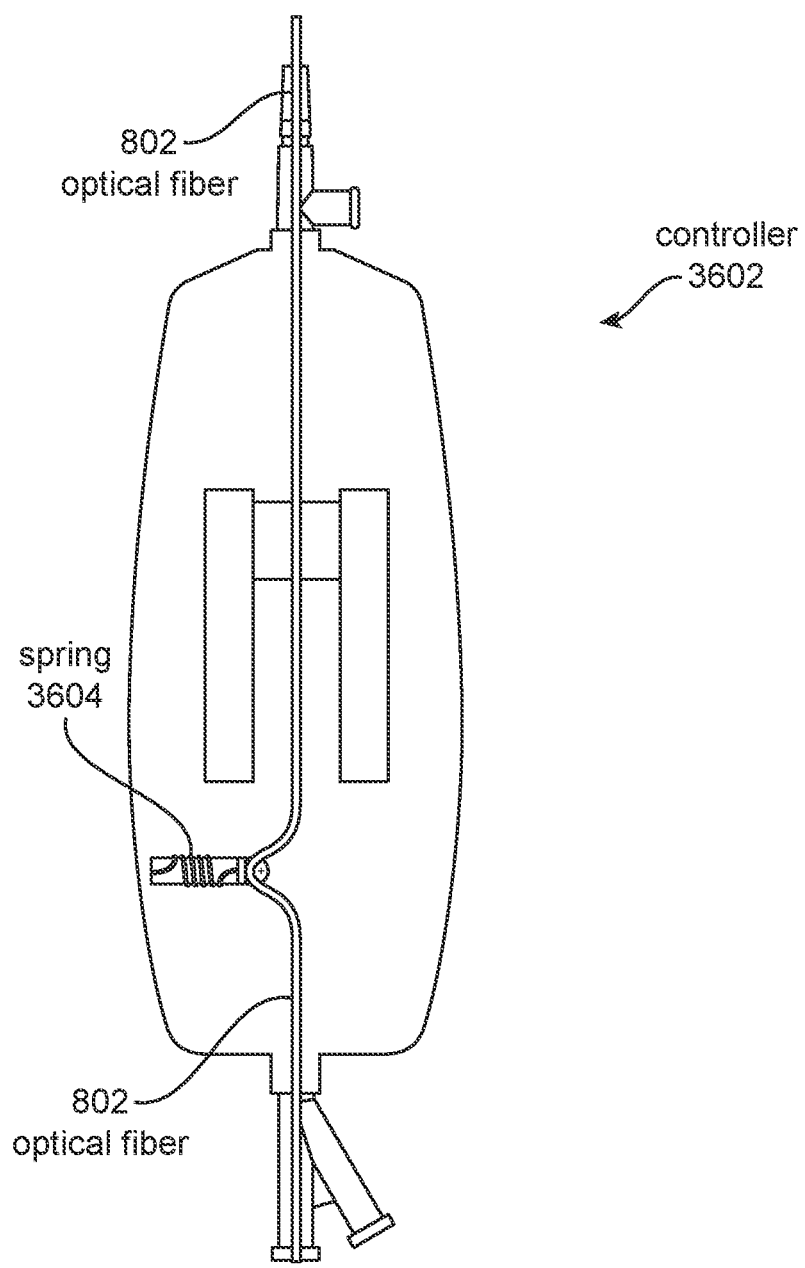
Figure 37:
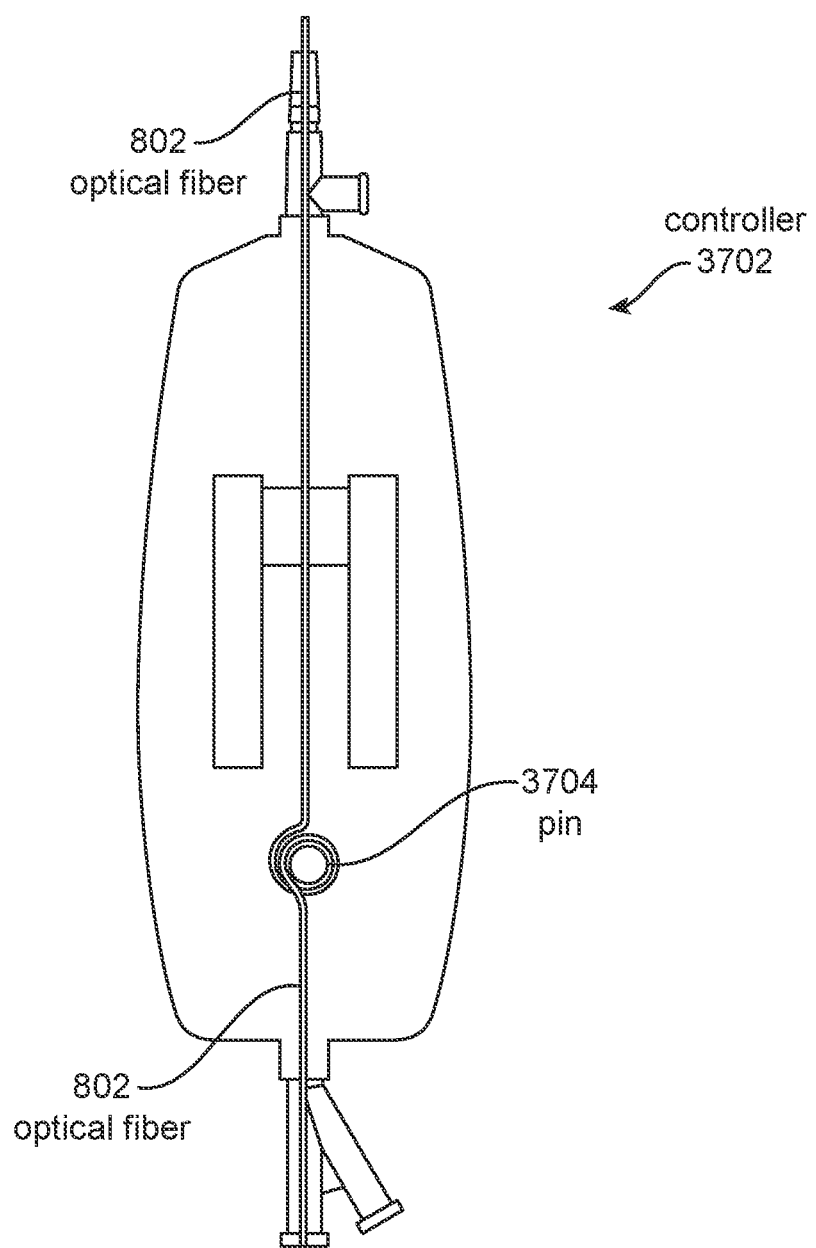

FIGS. 35, 36, and 37 illustrate possible examples of controllers that include mechanisms to passively manage slack that may occur in the optical fiber as it is moved longitudinally. Specifically, FIG. 35 illustrates a controller 3502 including a pin 3504. As shown in FIG. 35, the pin 3504 may lay longitudinally with respect to the controller 3502. In such examples, the optical fiber 802 winds around the pin 3504, such that any slack in the optical fiber 802 is taken by the pin 3504. Rotation of the pin 3504 may wind or unwind the optical fiber 802 to impart longitudinal movement on the optical fiber 802.

FIG. 36 illustrates a controller 3602 including a spring 3604. According to such examples, the spring 3604 may be extended or contracted through an actuator on the controller 3602 accessible by an operator. When the spring 3604 is extended or contracted, the optical fiber 802 may be similarly moved, thus imparting longitudinal movement on the optical fiber 802. In some examples, the spring 3604 is directly coupled to the optical fiber 802. In other examples, an intermediary material, such as a movable pin, is coupled to the spring 3604. In such examples, the optical fiber 802 may be wound about the pin (multiple times or a single time) in order to translate the movement of the spring 3604 to the optical fiber 802.

It is understood that, while only a single spring 3604 is illustrated in FIG. 36, multiple springs could be used, and these springs could additionally be separated across the housing of the controller to thereby take up further slack from the optical fiber 802.

Additionally, while a spring 3604 is specifically named, it is understood that equivalent mechanisms may be used to achieve the same results. These include but are not limited to conventional springs, braided shafts (either metallic or polymeric), elastic bands, nitinol bands, and nitinol stent-like structures.

FIG. 37 illustrates a controller 3702 including a pin 3704. Dissimilar to the pin 3504 of FIG. 35, this pin 3704 may lie vertically with respect to the controller 3702. The optical fiber 802 may wind around this pin 3704 in such a way that slack is introduced. When the optical fiber 802 is moved from proximal to distal, the slack will be reduced until the optical fiber 802 is eventually stopped from movement by the pin 3704.

Figure 38:
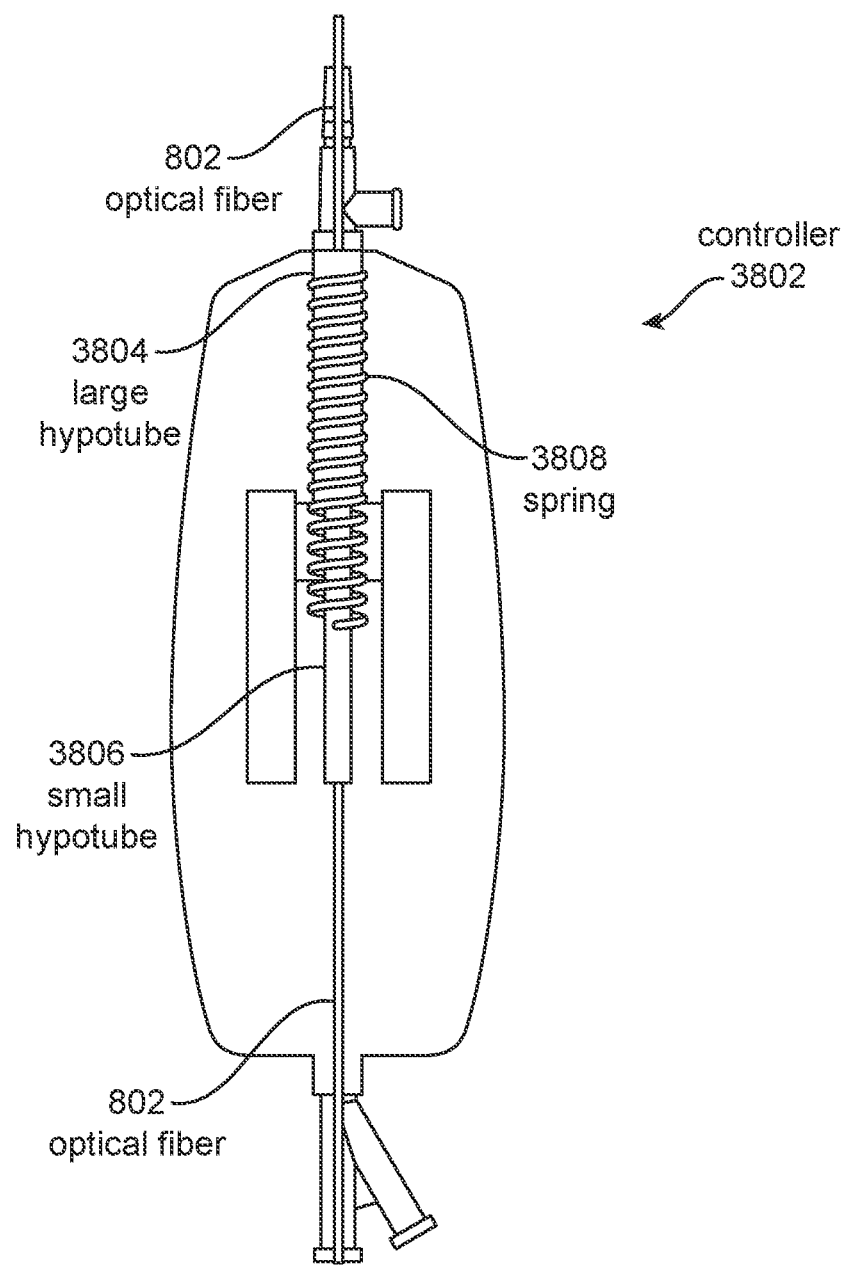

FIG. 38 illustrates a controller 3802 including another variation of a telescoping tube, similar to that shown in FIG. 34. In FIG. 38, a small hypotube 3806 is slidably coupled to a large hypotube 3804. Additionally, a spring 3808 may be coupled to each of the small hypotube 3806 and the large hypotube 3804. This spring 3808 may assist longitudinal movement of the small hypotube 3806. In some examples, the spring 3808 returns the small hypotube 3806 to its initial position. According to some examples, the optical fiber 802 is coupled to the small hypotube 3806, thereby imparting the longitudinal motion of the small hypotube 3806 to the optical fiber 802.

Additionally, while a spring 3808 is specifically named, it is understood that equivalent mechanisms may be used to achieve the same results. These include but are not limited to conventional springs, braided shafts (either metallic or polymeric), elastic bands, nitinol bands, and nitinol stent-like structures.

In any or all of the example controllers of FIGS. 34-38, locking mechanisms may be included in or on the controllers. For example, ball detent pins or housing notches may be included such that, once the optical fiber 802 has been longitudinally moved to the desired location, it is locked into that position until an operator wishes to move it.

Additionally, in FIGS. 34-38, the optical fiber 802 is named and numbered in more than one location. This is to facilitate understanding that this is the same component, as it is shown broken up by other features, and should not be construed as meaning that more than one optical fiber 802 needs to be present in this disclosure. That is not to say, however, that more than one optical fiber 802 could not be present if desired.

Included in the present disclosure is a device including an elongated body having a proximal end and a distal end opposite the proximal end, the elongated body extending along a central longitudinal axis. In some examples, the device includes a distal elongated body portion extending from the elongated body and distal to the elongated body along the central longitudinal axis, the distal elongated body portion located adjacent the distal end. According to some examples, the device includes an optical fiber spaced from the central longitudinal axis and extending from the proximal end to the distal elongated body portion, the optical fiber being configured to transmit laser energy into a fluid causing a cavitation bubble to propagate a pressure wave. The device may include a fiber positioner at least partially circumferentially surrounding the optical fiber and circumferentially surrounding the distal elongated body portion, the fiber positioner being translationally coupled to the distal elongated body portion such that the fiber positioner can move between a first position to a second position located distal the first position, and the fiber positioner being rotationally fixedly coupled to the distal elongated body portion such that the fiber positioner maintains a fixed angle respective to the distal elongated body portion.

In some examples, the optical fiber is fixedly coupled to the fiber positioner such that each of the optical fiber and the fiber positioner are translationally coupled and rotationally fixedly coupled to the distal elongated body portion. According to some examples, the distal elongated body portion comprises an oval-shaped cross-sectional profile.

The distal elongated body portion may include a longitudinal depression configured to rotationally fixedly couple the fiber positioner to the distal elongated body portion. In some examples, the fiber positioner comprises an indentation configured to correspond with the longitudinal depression, whereby the longitudinal depression receives the indentation. The indentation may partially surround the optical fiber. In some examples, the longitudinal depression partially surrounds the optical fiber. According to some examples, the fiber positioner comprises a protrusion at least partially circumferentially surrounding the optical fiber.

Also included in the present disclosure is a device, including an elongated body having a proximal end and a distal end opposite the proximal end, the elongated body extending along a central longitudinal axis. In some examples, the device includes a distal elongated body portion extending from the elongated body and distal to the elongated body along the central longitudinal axis, the distal elongated body portion located adjacent the distal end. According to some examples, the device includes an optical fiber spaced from the central longitudinal axis and extending from the proximal end to the distal elongated body portion, the optical fiber being configured to transmit laser energy into a fluid causing a cavitation bubble to propagate a pressure wave. The device may include a fiber positioner at least partially circumferentially surrounding the optical fiber and partially circumferentially surrounding the distal elongated body portion, the fiber positioner being translationally coupled to the distal elongated body portion such that the fiber positioner can move between a first position to a second position located distal the first position, and the fiber positioner being rotationally fixedly coupled to the distal elongated body portion such that the fiber positioner maintains a fixed angle respective to the distal elongated body portion.

In some examples, the distal elongated body portion comprises a longitudinal track. According to some examples, the fiber positioner comprises a top portion, a bottom portion opposite the top portion, and a middle portion therebetween, the top portion partially circumferentially surrounding the optical fiber. The middle portion may define a width that is less than each of a width of the top portion and a width of the bottom portion. In some examples, the longitudinal track comprises a proximal track end and a distal track end opposite the proximal track end, the proximal track end and the distal track end each configured to stop a movement of the fiber positioner.

According to some examples, the distal elongated body portion comprises a guidewire lumen and a fiber positioner lumen. The distal elongated body portion may include a slit configured to fluidly couple the fiber positioner lumen to an outer edge of the distal elongated body portion. In some examples, the fiber positioner includes a protrusion configured to protrude from the fiber positioner lumen beyond the outer edge of the distal elongated body portion through the slit, the protrusion at least partially circumferentially surrounding the optical fiber.

According to some examples, the fiber positioner lumen comprises a proximal fiber positioner lumen end beginning at the proximal end and a distal fiber positioner lumen end opposite the proximal fiber positioner lumen end, the distal fiber positioner lumen end proximal to the distal end of the elongated body, the distal fiber positioner lumen end configured to stop a movement of the fiber positioner.

Also included in the present disclosure is a device including an elongated body having a proximal end and a distal end opposite the proximal end, the elongated body extending along a central longitudinal axis. In some examples, the device includes a distal elongated body portion extending from the elongated body and distal to the elongated body along the central longitudinal axis, the distal elongated body portion located adjacent the distal end. According to some examples, the device includes a balloon positioned along the distal elongated body portion, the balloon having an interior balloon surface and an exterior balloon surface, the balloon being configured to receive an inflation fluid to inflate the balloon such that the exterior balloon surface contacts a calcified lesion within a vasculature of a patient. The device may include an optical fiber spaced from the central longitudinal axis and extending from the proximal end to the distal elongated body portion, the optical fiber being configured to transmit laser energy into the inflation fluid causing a cavitation bubble to propagate a pressure wave. In some examples, the device includes a fiber positioner at least partially circumferentially surrounding the optical fiber, the fiber positioner being translationally coupled to the distal elongated body portion such that the fiber positioner can move between a first position to a second position located distal the first position, and the fiber positioner being rotationally fixedly coupled to the distal elongated body portion such that the fiber positioner maintains a fixed angle respective to the distal elongated body portion.

According to some examples, the fiber positioner comprises a distal face and a proximal face opposite the distal face, the proximal face and the distal face of the fiber positioner longitudinally located within the balloon. The fiber positioner may include a distal face and a proximal face opposite the distal face, the proximal face of the fiber positioner distal to a proximal end of the balloon, and the distal face of the fiber positioner proximal to a distal end of the balloon.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

We claim:

1. A device, comprising:
    an elongated body having a proximal end and a distal end opposite the proximal end, the elongated body extending along a central longitudinal axis;
    a distal elongated body portion extending from the elongated body and distal to the elongated body along the central longitudinal axis, the distal elongated body portion located adjacent the distal end;
    an optical fiber spaced from the central longitudinal axis and extending from the proximal end to the distal elongated body portion, the optical fiber being configured to transmit laser energy into a fluid causing a cavitation bubble to propagate a pressure wave; and
    a fiber positioner at least partially circumferentially surrounding the optical fiber and at least partially circumferentially surrounding the distal elongated body portion, the fiber positioner spaced apart from and distal to the proximal end of the elongated body, the fiber positioner being translationally coupled to the distal elongated body portion such that the fiber positioner can move between a first position and a second position located distal to the first position, and the fiber positioner defining a shape that rotationally fixedly couples the fiber positioner to the distal elongated body portion such that the fiber positioner maintains a substantially fixed angle respective to the distal elongated body portion.

2. The device of claim 1, wherein the optical fiber is fixedly coupled to the fiber positioner such that each of the optical fiber and the fiber positioner are translationally coupled and rotationally fixedly coupled to the distal elongated body portion.

3. The device of claim 1, wherein the distal elongated body portion comprises an oval-shaped cross-sectional profile.

4. The device of claim 3, wherein the fiber positioner comprises a protrusion at least partially circumferentially surrounding the optical fiber.

5. The device of claim 1, wherein the distal elongated body portion comprises a longitudinal depression configured to rotationally fixedly couple the fiber positioner to the distal elongated body portion.

6. The device of claim 5, wherein the longitudinal depression partially surrounds the optical fiber.

7. The device of claim 6, wherein the longitudinal depression substantially prevents the optical fiber from rotating about the distal elongated body portion.

8. The device of claim 5, wherein the longitudinal depression extends along a portion of a length of the distal elongated body portion.

9. The device of claim 8, wherein the fiber positioner is configured to translate along the portion of the length of the distal elongated body portion along which the longitudinal depression extends.

10. The device of claim 5, wherein the longitudinal depression extends along an entire length of the distal elongated body portion.

11. The device of claim 5, wherein the fiber positioner comprises a protrusion at least partially circumferentially surrounding the optical fiber.

12. The device of claim 1, wherein the fiber positioner comprises a protrusion at least partially circumferentially surrounding the optical fiber.

13. The device of claim 1, further comprising a balloon positioned along the distal elongated body portion, the balloon having an interior balloon surface and an exterior balloon surface, the balloon being configured to receive an inflation fluid to inflate the balloon such that the exterior balloon surface contacts a calcified lesion within a vasculature of a patient.

14. The device of claim 13, wherein the fiber positioner comprises a distal face and a proximal face opposite the distal face, the proximal face and the distal face of the fiber positioner longitudinally located within the balloon.

15. The device of claim 13, wherein the fiber positioner comprises a distal face and a proximal face opposite the distal face, the proximal face of the fiber positioner distal to a proximal end of the balloon, and the distal face of the fiber positioner proximal to a distal end of the balloon.

16. The device of claim 1, wherein the fiber positioner fully circumferentially surrounds the optical fiber.

17. The device of claim 1, wherein the fiber positioner fully circumferentially surrounds the distal elongated body portion.

18. The device of claim 1, wherein the fiber positioner comprises a marker band configured to indicate a location of the fiber positioner within a vasculature of a patient.

19. The device of claim 1, further comprising:
    a marker band at least partially surrounding the distal elongated body portion; and
    a spring coupled to each of the marker band and the fiber positioner, the spring circumferentially surrounding the distal elongated body portion.

20. The device of claim 19, wherein the marker band is located at a position selected from the group consisting of proximal to the fiber positioner, distal to the fiber positioner, and combinations thereof.

* * * * *